United States Patent
Gavelle et al.

(10) Patent No.: US 11,339,120 B2
(45) Date of Patent: May 24, 2022

(54) PHENYL DERIVATIVES AS CANNABINOID RECEPTOR 2 AGONISTS

(71) Applicant: Hoffmann-La Roche Inc., Little Falls, NJ (US)

(72) Inventors: Olivier Gavelle, Basel (CH); Uwe Grether, Basel (CH); Matthias Nettekoven, Basel (CH); Stephan Roever, Basel (CH); Mark Rogers-Evans, Basel (CH); Didier Rombach, Basel (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 16/930,013

(22) Filed: Jul. 15, 2020

(65) Prior Publication Data

US 2021/0171441 A1    Jun. 10, 2021

Related U.S. Application Data

(63) Continuation of application No. 16/003,385, filed on Jun. 8, 2018, now abandoned, which is a continuation of application No. PCT/EP2016/079825, filed on Dec. 6, 2016.

(30) Foreign Application Priority Data

Dec. 9, 2015 (EP) ................... 15198733

(51) Int. Cl.
| | | |
|---|---|---|
| C07D 207/16 | (2006.01) |
| C07D 231/12 | (2006.01) |
| C07D 401/10 | (2006.01) |
| C07D 403/10 | (2006.01) |
| C07D 413/06 | (2006.01) |
| C07D 413/10 | (2006.01) |
| C07D 413/12 | (2006.01) |
| C07D 205/04 | (2006.01) |
| C07C 235/52 | (2006.01) |
| C07D 331/04 | (2006.01) |
| C07D 271/06 | (2006.01) |
| C07D 213/61 | (2006.01) |
| C07D 209/54 | (2006.01) |
| C07D 305/06 | (2006.01) |
| C07D 207/14 | (2006.01) |
| C07D 277/30 | (2006.01) |
| C07C 235/48 | (2006.01) |
| C07C 237/22 | (2006.01) |
| C07C 231/02 | (2006.01) |
| C07D 207/10 | (2006.01) |
| C07D 277/28 | (2006.01) |
| C07D 305/08 | (2006.01) |

(52) U.S. Cl.
CPC .......... *C07C 235/52* (2013.01); *C07C 231/02* (2013.01); *C07C 235/48* (2013.01); *C07C 237/22* (2013.01); *C07D 205/04* (2013.01); *C07D 207/10* (2013.01); *C07D 207/14* (2013.01); *C07D 207/16* (2013.01); *C07D 209/54* (2013.01); *C07D 213/61* (2013.01); *C07D 231/12* (2013.01); *C07D 271/06* (2013.01); *C07D 277/28* (2013.01); *C07D 277/30* (2013.01); *C07D 305/06* (2013.01); *C07D 305/08* (2013.01); *C07D 331/04* (2013.01); *C07D 401/10* (2013.01); *C07D 403/10* (2013.01); *C07D 413/06* (2013.01); *C07D 413/10* (2013.01); *C07D 413/12* (2013.01); *C07B 2200/07* (2013.01); *C07C 2601/02* (2017.05)

(58) Field of Classification Search
CPC .. C07D 207/16; C07D 231/12; C07D 401/10; C07D 403/10; C07D 413/06; C07D 413/10; C07D 413/12; C07D 205/04; C07C 2601/02
See application file for complete search history.

(56) References Cited

U.S. PATENT DOCUMENTS

| | | |
|---|---|---|
| 7,678,820 B2 | 3/2010 | Harada et al. |
| 7,951,825 B2 | 5/2011 | Harada et al. |
| 9,303,012 B2 | 4/2016 | Bendels et al. |

(Continued)

FOREIGN PATENT DOCUMENTS

| | | |
|---|---|---|
| WO | 02/057236 A1 | 7/2002 |
| WO | 2012/168350 A1 | 12/2012 |

(Continued)

OTHER PUBLICATIONS

International Search Report and Written Opinion for International Patent Application No. PCT/EP2016/079825 completed on Jan. 11, 2017.

(Continued)

*Primary Examiner* — Matthew P Coughlin
(74) *Attorney, Agent, or Firm* — Zong-Qiang Bill Tian

(57) ABSTRACT

The invention relates to a compound of formula (I)

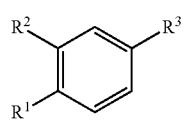

wherein $R^1$ to $R^3$ are defined as in the description and in the claims. The compound of formula (I) can be used as a medicament.

20 Claims, No Drawings

(56) References Cited

U.S. PATENT DOCUMENTS

| | | | |
|---|---|---|---|
| 9,321,727 B2 | 4/2016 | Bissantz et al. | |
| 9,403,808 B2 | 8/2016 | Bissantz et al. | |
| 9,409,866 B2 | 8/2016 | Grether et al. | |
| 9,512,141 B2 | 12/2016 | Dhurwasulu et al. | |
| 9,522,886 B2 | 12/2016 | Frei et al. | |
| 10,308,659 B2 | 6/2019 | Gavelle et al. | |
| 2012/0316147 A1* | 12/2012 | Bissantz | C07D 417/12 514/210.02 |
| 2013/0109665 A1 | 5/2013 | Bissantz et al. | |
| 2016/0137606 A1 | 5/2016 | Bissantz et al. | |
| 2016/0376237 A1 | 12/2016 | Gobbi et al. | |
| 2016/0376262 A1 | 12/2016 | Gobbi et al. | |
| 2018/0327360 A1 | 11/2018 | Gobbi et al. | |
| 2018/0327396 A1 | 11/2018 | Gobbi et al. | |

FOREIGN PATENT DOCUMENTS

| | | |
|---|---|---|
| WO | 2013/060751 A1 | 5/2013 |
| WO | 2014/086705 A1 | 6/2014 |
| WO | 2014/086805 A1 | 6/2014 |
| WO | 2014/086806 A1 | 6/2014 |
| WO | 2014/086807 A1 | 6/2014 |
| WO | 2014/154612 A1 | 10/2014 |
| WO | 2015/150438 A1 | 10/2015 |
| WO | 2015/150440 A1 | 10/2015 |

OTHER PUBLICATIONS

Ex parte Cao, Decision rendered by the Board of Patent Appeals and Interferences in U.S. Appl. No. 10/696,862, filed Sep. 21, 2011 (year: 2011).

Lucchesi et al., "1-2-Dihydro-2-oxopyridine-3-carboxamides: The C-5 Substituent is Responsible for Functionality Switch at CB2 Cannabinoid Receptor" Eur J Med Chem. 74:524-532 (Mar. 3, 2014).

Patani et al., "Bioisoterism: A Rational Approach in Drug Design" Chem. Rev. 96:3147-3176.

Sheridan et al., "The Most Common Chemical Replacements in Drug-Like Compounds" J. Chem. Inf. Comput. Sci. 42(1):103-108 (2002).

* cited by examiner

PHENYL DERIVATIVES AS CANNABINOID RECEPTOR 2 AGONISTS

CROSS-REFERENCE TO RELATED APPLICATIONS

This application is a continuation of U.S. application Ser. No. 16/003,385, filed 8 Jun. 2018 (now abandoned), which is a continuation of International Patent Application No. PCT/EP2016/079825, filed 6 Dec. 2016, which claims the benefit of priority to European Patent Application No. 15198733.6, filed 9 Dec. 2015, the contents of which applications are hereby incorporated by reference in their entirety.

The present invention relates to organic compounds useful for therapy and/or prophylaxis in a mammal, and in particular to compounds that are preferential agonists of the Cannabinoid Receptor 2.

The invention relates in particular to a compound of formula (I)

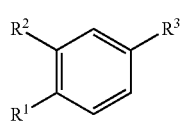

wherein
$R^1$ is cyclopropyl, alkyl or haloazetidinyl;
$R^2$ is cyclopropylmethoxy, alkoxy, haloalkoxy, halopyridinyl, alkylpyrazolyl or halopyrrolidinyl;
provided that at least one of $R^1$ and $R^2$ is cyclopropyl or cyclopropylmethoxy;
$R^3$ is —C(O)—NH—C($R^4R^5$)—$R^6$, —C(O)—$R^7$ or $R^1$;
$R^4$ and $R^5$ are independently selected from hydrogen, alkyl, cycloalkyl, cycloalkylalkyl, alkylsulfonylalkyl and alkyloxetanyl;
or $R^4$ and $R^5$ together with the carbon atom to which they are attached form oxetanyl or dioxothiethanyl;
$R^6$ is aminocarbonyl, 5-methyl-1,2,4-oxadiazol-3-yl, hydroxyalkyl, thiazolyl, alkoxycarbonyl, carboxy, difluoroazetidinylcarbonyl, 5-amino-1,2,4-oxadiazol-3-yl, alkylaminocarbonyl or aminocarbonylalkyl;
$R^7$ is (aminocarbonyl)(difluoro)pyrrolidinyl or (aminocarbonyl)azaspiro[2.4]heptyl; and
$R^8$ is 3-alkyl-1,2,4-oxadiazol-5-yl or 5-alkyl-1,2,4-oxadiazol-3-yl;
or a pharmaceutically acceptable salt or ester thereof.

The compound of formula (I) is particularly useful in the treatment or prophylaxis of e.g. pain, atherosclerosis, age-related macular degeneration, diabetic retinopathy, glaucoma, retinal vein occlusion, retinopathy of prematurity, ocular ischemic syndrome, geographic atrophy, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, neurodegeneration, amyotrophic lateral sclerosis, stroke, transient ischemic attack or uveitis.

The compound of formula (I) is in particular useful in the treatment or prophylaxis of diabetic retinopathy, retinal vein occlusion or uveitis.

The cannabinoid receptors are a class of cell membrane receptors belonging to the G protein-coupled receptor superfamily. There are currently two known subtypes, termed Cannabinoid Receptor 1 (CB1) and Cannabinoid Receptor 2 (CB2). The CB1 receptor is mainly expressed in the central nervous (i.e. amygdala cerebellum, hippocampus) system and to a lesser amount in the periphery. CB2, which is encoded by the CNR2 gene, is mostly expressed peripherally, on cells of the immune system, such as macrophages and T-cells (Ashton, J. C. et al. Curr Neuropharmacol 2007, 5(2), 73-80; Miller, A. M. et al. Br J Pharmacol 2008, 153(2), 299-308; Centonze, D., et al. Curr Pharm Des 2008, 14(23), 2370-42), and in the gastrointestinal system (Wright, K. L. et al. Br J Pharmacol 2008, 153(2), 263-70). The CB2 receptor is also widely distributed in the brain where it is found primarily on microglia and not neurons (Cabral, G. A. et al. Br J Pharmacol 2008, 153(2): 240-51).

The interest in CB2 receptor agonists has been steadily on the rise during the last decade (currently 30-40 patent applications/year) due to the fact that several of the early compounds have been shown to have beneficial effects in pre-clinical models for a number of human diseases including chronic pain (Beltramo, M. Mini Rev Med Chem 2009, 9(1), 11-25), atherosclerosis (Mach, F. et al. J Neuroendocrinol 2008, 20 Suppl 1, 53-7), regulation of bone mass (Bab, I. et al. Br J Pharmacol 2008, 153(2), 182-8), neuroinflammation (Cabral, G. A. et al. J Leukoc Biol 2005, 78(6), 1192-7), ischemia/reperfusion injury (Pacher, P. et al. Br J Pharmacol 2008, 153(2), 252-62), systemic fibrosis (Akhmetshina, A. et al. Arthritis Rheum 2009, 60(4), 1129-36; Garcia-Gonzalez, E. et al. Rheumatology (Oxford) 2009, 48(9), 1050-6), liver fibrosis (Julien, B. et al. Gastroenterology 2005, 128(3), 742-55; Munoz-Luque, J. et al. J Pharmacol Exp Ther 2008, 324(2), 475-83).

Ischemia/reperfusion (I/R) injury is the principal cause of tissue damage occurring in conditions such as stroke, myocardial infarction, cardiopulmonary bypass and other vascular surgeries, and organ transplantation, as well as a major mechanism of end-organ damage complicating the course of circulatory shock of various etiologies. All these conditions are characterized by a disruption of normal blood supply resulting in an insufficient tissue oxygenation. Re-oxygenation e.g., reperfusion is the ultimate treatment to restore normal tissue oxygenation. However the absence of oxygen and nutrients from blood creates a condition in which the restoration of circulation results in further tissue damage. The damage of reperfusion injury is due in part to the inflammatory response of damaged tissues. White blood cells, carried to the area by the newly returning blood, release a host of inflammatory factors such as interleukins as well as free radicals in response to tissue damage. The restored blood flow reintroduces oxygen within cells that damages cellular proteins, DNA, and the plasma membrane.

Remote ischemic preconditioning (RIPC) represents a strategy for harnessing the body's endogenous protective capabilities against the injury incurred by ischemia and reperfusion. It describes the intriguing phenomenon in which transient non-lethal ischemia and reperfusion of one organ or tissue confers resistance to a subsequent episode of "lethal" ischemia reperfusion injury in a remote organ or tissue. The actual mechanism through which transient ischemia and reperfusion of an organ or tissue confers protection is currently unknown although several hypotheses have been proposed.

The humoral hypothesis proposes that the endogenous substance (such as adenosine, bradykinin, opioids, CGRP, endocannabinoids, Angiotensin I or some other as yet unidentified humoral factor) generated in the remote organ or tissue enters the blood stream and activates its respective receptor in the target tissue and thereby recruiting the various intracellular pathways of cardioprotection implicated in ischemic preconditioning.

Recent data indicates that endocannabinnoids and their receptors, in particular CB2 might be involved in preconditioning and contribute to prevent reperfusion injury by downregulation of the inflammatory response (Pacher, P. et al. Br J Pharmacol 2008, 153(2), 252-62). Specifically, recent studies using CB2 tool agonists demonstrated the efficacy of this concept for reducing the I/R injury in the heart (Defer, N. et al. Faseb J 2009, 23(7), 2120-30), the brain (Zhang, M. et al. J Cereb Blood Flow Metab 2007, 27(7), 1387-96), the liver (Batkai, S. et al. Faseb J 2007, 21(8), 1788-800) and the kidney (Feizi, A. et al. Exp Toxicol Pathol 2008, 60(4-5), 405-10).

Moreover, over the last few years, a growing body of literature indicates that CB2 can also be of interest in sub-chronic and chronic setting. Specific upregulation of CB1 and CB2 has been shown to be associated in animal models of chronic diseases associated with fibrosis (Garcia-Gonzalez, E. et al. Rheumatology (Oxford) 2009, 48(9), 1050-6; Yang, Y. Y. et al. Liver Int 2009, 29(5), 678-85) with a relevant expression of CB2 in myofibroblasts, the cells responsible for fibrosis progression.

Activation of CB2 receptor by selective CB2 agonist has in fact been shown to exert anti-fibrotic effect in diffuse systemic sclerosis (Garcia-Gonzalez, E. et al. Rheumatology (Oxford) 2009, 48(9), 1050-6) and CB2 receptor has emerged as a critical target in experimental dermal fibrosis (Akhmetshina, A. et al. Arthritis Rheum 2009, 60(4), 1129-36) and in in liver pathophysiology, including fibrogenesis associated with chronic liver diseases (Lotersztajn, S. et al. Gastroenterol Clin Biol 2007, 31(3), 255-8; Mallat, A. et al. Expert Opin Ther Targets 2007, 11(3), 403-9; Lotersztajn, S. et al. Br J Pharmacol 2008, 153(2), 286-9).

The compounds of the invention bind to and modulate the CB2 receptor and have lower CB1 receptor activity.

In the present description the term "alkyl", alone or in combination, signifies a straight-chain or branched-chain alkyl group with 1 to 8 carbon atoms, particularly a straight or branched-chain alkyl group with 1 to 6 carbon atoms and more particularly a straight or branched-chain alkyl group with 1 to 4 carbon atoms. Examples of straight-chain and branched-chain $C_1$-$C_8$ alkyl groups are methyl, ethyl, propyl, isopropyl, butyl, isobutyl, tert.-butyl, the isomeric pentyls, the isomeric hexyls, the isomeric heptyls and the isomeric octyls, particularly methyl, ethyl, propyl, butyl and pentyl more particularly methyl, ethyl, propyl, isopropyl, isobutyl, tert.-butyl and isopentyl. Particular examples of alkyl are methyl, ethyl, propyl, isopropyl, butyl and tert.-butyl.

The term "cycloalkyl", alone or in combination, signifies a cycloalkyl ring with 3 to 8 carbon atoms and particularly a cycloalkyl ring with 3 to 6 carbon atoms. Examples of cycloalkyl are cyclopropyl, cyclobutyl, cyclopentyl and cyclohexyl, cycloheptyl and cyclooctyl. A particular example of "cycloalkyl" is cyclopropyl.

The term "alkoxy", alone or in combination, signifies a group of the formula alkyl-O— in which the term "alkyl" has the previously given significance, such as methoxy, ethoxy, n-propoxy, isopropoxy, n-butoxy, isobutoxy, sec-butoxy and tert-butoxy. Particular "alkoxy" are methoxy, ethoxy and isopropoxy.

The term "oxy", alone or in combination, signifies the —O— group.

The terms "halogen" or "halo", alone or in combination, signifies fluorine, chlorine, bromine or iodine and particularly fluorine, chlorine or bromine, more particularly fluorine and chlorine. The term "halo", in combination with another group, denotes the substitution of said group with at least one halogen, particularly substituted with one to five halogens, particularly one to four halogens, i.e. one, two, three or four halogens. A particular "halogen" is fluorine in $R^1$ to $R^3$.

The term "haloalkoxy", alone or in combination, denotes an alkoxy group substituted with at least one halogen, particularly substituted with one to five halogens, particularly one to three halogens, particularly one to three fluorine. Particular "haloalkoxy" are fluoroethyloxy, difluoroehtyloxy and trifluoroethyloxy.

The terms "hydroxyl" and "hydroxy", alone or in combination, signify the —OH group.

The term "carbonyl", alone or in combination, signifies the —C(O)— group.

The term "amino", alone or in combination, signifies the primary amino group (—$NH_2$), the secondary amino group (—NH—), or the tertiary amino group (—N—).

The term "sulfonyl", alone or in combination, signifies the —$SO_2$— group.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid, particularly hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein. In addition these salts may be prepared form addition of an inorganic base or an organic base to the free acid. Salts derived from an inorganic base include, but are not limited to, the sodium, potassium, lithium, ammonium, calcium, magnesium salts. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins. The compound of formula (I) can also be present in the form of zwitterions. Particularly preferred pharmaceutically acceptable salts of compounds of formula (I) are the salts of hydrochloric acid, hydrobromic acid, sulfuric acid, phosphoric acid and methanesulfonic acid.

"Pharmaceutically acceptable esters" means that the compound of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compound of general formula (I), similar to the metabolically labile esters, which are capable of producing the parent compound of general formula (I) in vivo, are within the scope of this invention.

If one of the starting materials or compounds of formula (I) contain one or more functional groups which are not stable or are reactive under the reaction conditions of one or more reaction steps, appropriate protecting groups (as described e.g. in "Protective Groups in Organic Chemistry" by T. W. Greene and P. G. M. Wuts, 3$^{rd}$ Ed., 1999, Wiley, New York) can be introduced before the critical step applying methods well known in the art. Such protecting groups can be removed at a later stage of the synthesis using standard methods described in the literature. Examples of protecting groups are tert-butoxycarbonyl (Boc), 9-fluorenylmethyl carbamate (Fmoc), 2-trimethylsilylethyl carbamate (Teoc), carbobenzyloxy (Cbz) and p-methoxybenzyloxycarbonyl (Moz).

The compound of formula (I) can contain several asymmetric centers and can be present in the form of optically pure enantiomers, mixtures of enantiomers such as, for example, racemates, mixtures of diastereoisomers, diastereoisomeric racemates or mixtures of diastereoisomeric racemates.

The term "asymmetric carbon atom" means a carbon atom with four different substituents. According to the Cahn-Ingold-Prelog Convention an asymmetric carbon atom can be of the "R" or "S" configuration.

The invention thus relates in particular to:

A compound of formula (I) wherein $R^1$ is cyclopropyl;

A compound of formula (I) wherein $R^2$ is cyclopropylmethoxy, alkoxy, haloalkoxy or halopyrrolidinyl;

A compound of formula (I) wherein $R^2$ is cyclopropylmethoxy, propyloxy, fluoroethoxy, trifluoroethoxy or difluoropyrrolidinyl;

A compound of formula (I) wherein $R^4$ and $R^5$ are independently selected from hydrogen, alkyl, cycloalkyl and cycloalkylalkyl;

A compound of formula (I) wherein $R^4$ and $R^5$ are independently selected from hydrogen, methyl, butyl, cyclopropyl and cyclopropylmethyl;

A compound of formula (I) wherein $R^6$ is aminocarbonyl, 5-methyl-1,2,4-oxadiazol-3-yl, hydroxyalkyl or alkylaminocarbonyl;

A compound of formula (I) wherein $R^6$ is aminocarbonyl, 5-methyl-1,2,4-oxadiazol-3-yl, hydroxymethyl or methylaminocarbonyl;

A compound of formula (I) wherein $R^7$ is (aminocarbonyl)(difluoro)pyrrolidinyl; and A compound of formula (I) wherein $R^8$ is 3-tert.butyl-1,2,4-oxadiazol-5-yl, 5-tert.butyl-1,2,4-oxadiazol-3-yl or 5-methyl-1,2,4-oxadiazol-3-yl.

The invention further relates to a compound of formula (I) selected from (R)—N-(1-amino-4-methyl-1-oxopentan-2-yl)-3-(cyclopropylmethoxy)-4-methylbenzamide;

3-(cyclopropylmethoxy)-4-methyl-N-[2-(5-methyl-1,2,4-oxadiazol-3-yl)propan-2-yl]benzamide;

4-cyclopropyl-3-(cyclopropylmethoxy)-N-[2-(5-methyl-1,2,4-oxadiazol-3-yl)propan-2-yl]benzamide;

N2-[4-cyclopropyl-3-(cyclopropylmethoxy)benzoyl]-L-leucinamide;

4-cyclopropyl-3-(cyclopropylmethoxy)-N-(1-hydroxy-2-methylpropan-2-yl)benzamide;

4-cyclopropyl-3-(cyclopropylmethoxy)-N-[2-(1,3-thiazol-2-yl)propan-2-yl]benzamide;

ethyl 2-[4-cyclopropyl-3-(cyclopropylmethoxy)benzamido]-2-ethylbutanoate;

2-[4-cyclopropyl-3-(cyclopropylmethoxy)benzamido]-2-ethylbutanoic acid;

4-cyclopropyl-3-(cyclopropylmethoxy)-N-[3-(3,3-difluoroazetidine-1-carbonyl)pentan-3-yl]benzamide;

3-(cyclopropylmethoxy)-4-(3,3-difluoroazetidin-1-yl)-N-[2-(5-methyl-1,2,4-oxadiazol-3-yl)propan-2-yl]benzamide;

N-[2-(5-amino-1,2,4-oxadiazol-3-yl)propan-2-yl]-3-(cyclopropylmethoxy)-4-(3,3-difluoroazetidin-1-yl)benzamide;

N2-[3-(cyclopropylmethoxy)-4-(3,3-difluoroazetidin-1-yl)benzoyl]-N-methyl-L-leucinamide;

3-(cyclopropylmethoxy)-4-(3,3-difluoroazetidin-1-yl)-N-[(2S)-1-hydroxy-4-methylpentan-2-yl]benzamide;

3-tert-butyl-5-[4-cyclopropyl-3-(cyclopropylmethoxy)phenyl]-1,2,4-oxadiazole;

N-[3-(2-amino-2-oxoethyl)oxetan-3-yl]-4-cyclopropyl-3-(cyclopropylmethoxy)benzamide;

N-[3-(2-amino-2-oxoethyl)-1,1-dioxothietan-3-yl]-4-cyclopropyl-3-(cyclopropylmethoxy)benzamide;

1-[4-cyclopropyl-3-(cyclopropylmethoxy)benzoyl]-4,4-difluoro-L-prolinamide;

N-(3-carbamoylpentan-3-yl)-4-cyclopropyl-3-(cyclopropylmethoxy)benzamide;

N2-[4-cyclopropyl-3-(cyclopropylmethoxy)benzoyl]-N-methyl-L-leucinamide;

4-cyclopropyl-3-(cyclopropylmethoxy)-N-[(2S)-1-(methanesulfonyl)-2-(5-methyl-1,2,4-oxadiazol-3-yl)propan-2-yl]benzamide;

4-cyclopropyl-3-(cyclopropylmethoxy)-N-[(2R)-1-(methanesulfonyl)-2-(5-methyl-1,2,4-oxadiazol-3-yl)propan-2-yl]benzamide;

5-[4-cyclopropyl-3-(cyclopropylmethoxy)benzoyl]-5-azaspiro[2.4]heptane-6-carboxamide;

5-tert-butyl-3-[4-cyclopropyl-3-(2,2,2-trifluoroethoxy)phenyl]-1,2,4-oxadiazole;

5-tert-butyl-3-[4-cyclopropyl-3-(2,2-difluoroethoxy)phenyl]-1,2,4-oxadiazole;

4-cyclopropyl-N-[(2R)-1-cyclopropyl-2-(5-methyl-1,2,4-oxadiazol-3-yl)propan-2-yl]-3-(2,2,2-trifluoroethoxy)benzamide;

4-cyclopropyl-N-[(2S)-1-cyclopropyl-2-(5-methyl-1,2,4-oxadiazol-3-yl)propan-2-yl]-3-(2,2,2-trifluoroethoxy)benzamide;

N-[3-(2-amino-2-oxoethyl)-1,1-dioxo-thietan-3-yl]-4-cyclopropyl-3-(2,2,2-trifluoroethoxy)benzamide;

4-cyclopropyl-N-[(2R)-1-(methanesulfonyl)-2-(5-methyl-1,2,4-oxadiazol-3-yl)propan-2-yl]-3-(2,2,2-trifluoroethoxy)benzamide;

4-cyclopropyl-N-[(2S)-1-(methanesulfonyl)-2-(5-methyl-1,2,4-oxadiazol-3-yl)propan-2-yl]-3-(2,2,2-trifluoroethoxy)benzamide;

5-tert-butyl-3-[4-cyclopropyl-3-(2-fluoroethoxy)phenyl]-1,2,4-oxadiazole;

4-cyclopropyl-N-[(2R)-1-cyclopropyl-2-(5-methyl-1,2,4-oxadiazol-3-yl)propan-2-yl]-3-(2,2-difluoroethoxy)benzamide;

4-cyclopropyl-N-[(2S)-1-cyclopropyl-2-(5-methyl-1,2,4-oxadiazol-3-yl)propan-2-yl]-3-(2,2-difluoroethoxy)benzamide;

4-cyclopropyl-N-[(2R)-1-cyclopropyl-2-(5-methyl-1,2,4-oxadiazol-3-yl)propan-2-yl]-3-(2-fluoroethoxy)benzamide;

4-cyclopropyl-N-[(2S)-1-cyclopropyl-2-(5-methyl-1,2,4-oxadiazol-3-yl)propan-2-yl]-3-(2-fluoroethoxy)benzamide;

N-[(2S)-4-amino-2-cyclopropyl-4-oxobutan-2-yl]-4-cyclopropyl-3-(2,2,2-trifluoroethoxy)benzamide;

N-[(2R)-4-amino-2-cyclopropyl-4-oxobutan-2-yl]-4-cyclopropyl-3-(2,2,2-trifluoroethoxy)benzamide;
4-cyclopropyl-N-[(2S)-3,3-dimethyl-1-(methylamino)-1-oxobutan-2-yl]-3-[(propan-2-yl)oxy]benzamide;
4-cyclopropyl-N-[(2S)-1-cyclopropyl-2-(5-methyl-1,2,4-oxadiazol-3-yl)propan-2-yl]-3-[(propan-2-yl)oxy]benzamide;
4-cyclopropyl-N-[(2S)-3,3-dimethyl-1-(methylamino)-1-oxobutan-2-yl]-3-(2-fluoroethoxy)benzamide;
1-[4-cyclopropyl-3-(2-fluoroethoxy)benzoyl]-4,4-difluoro-L-prolinamide;
4-cyclopropyl-N-[(2S)-3,3-dimethyl-1-(methylamino)-1-oxobutan-2-yl]-3-(2,2,2-trifluoroethoxy)benzamide;
1-[4-cyclopropyl-3-(2,2,2-trifluoroethoxy)benzoyl]-4,4-difluoro-L-prolinamide;
N-[(2S)-4-amino-2-cyclopropyl-4-oxobutan-2-yl]-4-cyclopropyl-3-[(propan-2-yl)oxy]benzamide;
N-[(2R)-4-amino-2-cyclopropyl-4-oxobutan-2-yl]-4-cyclopropyl-3-[(propan-2-yl)oxy]benzamide;
N-[(2R)-4-amino-2-cyclopropyl-4-oxobutan-2-yl]-4-cyclopropyl-3-(2-fluoroethoxy)benzamide;
3-tert-butyl-5-{4-cyclopropyl-3-[(propan-2-yl)oxy]phenyl}-1,2,4-oxadiazole;
3-tert-butyl-5-[4-cyclopropyl-3-(3,3-difluoropyrrolidin-1-yl)phenyl]-1,2,4-oxadiazole;
1-{4-cyclopropyl-3-[(propan-2-yl)oxy]benzoyl}-4,4-difluoro-L-prolinamide;
4-cyclopropyl-N-[(2R)-1-cyclopropyl-2-(5-methyl-1,2,4-oxadiazol-3-yl)propan-2-yl]-3-[(propan-2-yl)oxy]benzamide;
4-cyclopropyl-N-[(2R)-1-cyclopropyl-2-(5-methyl-1,2,4-oxadiazol-3-yl)propan-2-yl]-3-(6-fluoropyridin-3-yl)benzamide;
N-[(2S)-4-amino-2-cyclopropyl-4-oxobutan-2-yl]-4-cyclopropyl-3-(2,2,2-trifluoroethoxy)benzamide;
N-[(2R)-4-amino-2-cyclopropyl-4-oxobutan-2-yl]-4-cyclopropyl-3-(6-fluoropyridin-3-yl)benzamide;
N-[(2S)-4-amino-2-cyclopropyl-4-oxobutan-2-yl]-4-cyclopropyl-3-(6-fluoropyridin-3-yl)benzamide;
N-[(2S)-4-amino-2-cyclopropyl-4-oxobutan-2-yl]-4-cyclopropyl-3-(2-fluoroethoxy)benzamide;
1-[4-cyclopropyl-3-(1-methyl-1H-pyrazol-5-yl)benzoyl]-4,4-difluoro-L-prolinamide;
4-cyclopropyl-N-[(2S)-3,3-dimethyl-1-(methylamino)-1-oxobutan-2-yl]-3-(1-methyl-1H-pyrazol-5-yl)benzamide;
1-[4-cyclopropyl-3-(6-fluoropyridin-3-yl)benzoyl]-4,4-difluoro-L-prolinamide;
4-cyclopropyl-N-[(2S)-3,3-dimethyl-1-(methylamino)-1-oxobutan-2-yl]-3-(6-fluoropyridin-3-yl)benzamide;
4-cyclopropyl-N-[(2S)-1-cyclopropyl-2-(5-methyl-1,2,4-oxadiazol-3-yl)propan-2-yl]-3-(1-methyl-1H-pyrazol-5-yl)benzamide;
4-cyclopropyl-N-[(2S)-1-cyclopropyl-2-(5-methyl-1,2,4-oxadiazol-3-yl)propan-2-yl]-3-(6-fluoropyridin-3-yl)benzamide;
N-[(2R)-4-amino-2-cyclopropyl-4-oxobutan-2-yl]-4-cyclopropyl-3-(3,3-difluoropyrrolidin-1-yl)benzamide;
N-[(2S)-4-amino-2-cyclopropyl-4-oxobutan-2-yl]-4-cyclopropyl-3-(3,3-difluoropyrrolidin-1-yl)benzamide;
4-cyclopropyl-N-[(2R)-1-cyclopropyl-2-(5-methyl-1,2,4-oxadiazol-3-yl)propan-2-yl]-3-(3,3-difluoropyrrolidin-1-yl)benzamide;
4-cyclopropyl-N-[(2S)-1-cyclopropyl-2-(5-methyl-1,2,4-oxadiazol-3-yl)propan-2-yl]-3-(3,3-difluoropyrrolidin-1-yl)benzamide;
1-[4-cyclopropyl-3-(3,3-difluoropyrrolidin-1-yl)benzoyl]-4,4-difluoro-L-prolinamide;
4-cyclopropyl-3-(3,3-difluoropyrrolidin-1-yl)-N-[(2S)-3,3-dimethyl-1-(methylamino)-1-oxobutan-2-yl]benzamide;
4-cyclopropyl-N-[(5-methyl-1,2,4-oxadiazol-3-yl)(3-methyloxetan-3-yl)methyl]-3-(2,2,2-trifluoroethoxy)benzamide;
4-cyclopropyl-N-[(5-methyl-1,2,4-oxadiazol-3-yl)(3-methyloxetan-3-yl)methyl]-3-[(propan-2-yl)oxy]benzamide;
N-[3-amino-1-(3-methyloxetan-3-yl)-3-oxopropyl]-4-cyclopropyl-3-(2,2,2-trifluoroethoxy)benzamide; and
4-cyclopropyl-3-(2-fluoroethoxy)-N-[(5-methyl-1,2,4-oxadiazol-3-yl)(3-methyloxetan-3-yl)methyl]benzamide.

The invention also relates to a compound of formula (I) selected from
N2-[4-cyclopropyl-3-(cyclopropylmethoxy)benzoyl]-L-leucinamide;
4-cyclopropyl-3-(cyclopropylmethoxy)-N-(1-hydroxy-2-methylpropan-2-yl)benzamide;
3-tert-butyl-5-[4-cyclopropyl-3-(cyclopropylmethoxy)phenyl]-1,2,4-oxadiazole;
N-[3-(2-amino-2-oxoethyl)oxetan-3-yl]-4-cyclopropyl-3-(cyclopropylmethoxy)benzamide;
N-[3-(2-amino-2-oxoethyl)-1,1-dioxothietan-3-yl]-4-cyclopropyl-3-(cyclopropylmethoxy)benzamide;
1-[4-cyclopropyl-3-(cyclopropylmethoxy)benzoyl]-4,4-difluoro-L-prolinamide;
5-tert-butyl-3-[4-cyclopropyl-3-(2-fluoroethoxy)phenyl]-1,2,4-oxadiazole;
N-[(2S)-4-amino-2-cyclopropyl-4-oxobutan-2-yl]-4-cyclopropyl-3-(2,2,2-trifluoroethoxy)benzamide;
4-cyclopropyl-N-[(2S)-3,3-dimethyl-1-(methylamino)-1-oxobutan-2-yl]-3-[(propan-2-yl)oxy]benzamide;
4-cyclopropyl-N-[(2S)-1-cyclopropyl-2-(5-methyl-1,2,4-oxadiazol-3-yl)propan-2-yl]-3-[(propan-2-yl)oxy]benzamide; and
N-[(2R)-4-amino-2-cyclopropyl-4-oxobutan-2-yl]-4-cyclopropyl-3-[(propan-2-yl)oxy]benzamide.

The preparation of the compound of formula (I) of the present invention may be carried out in sequential or convergent synthetic routes. Syntheses of the compounds of the invention are shown in the following schemes. The skills required for carrying out the reactions and purifications of the resulting products are known to those skilled in the art. The substituents and indices used in the following description of the processes have the significance given herein before unless indicated to the contrary. In more detail, the compounds of formula (I) can be manufactured by the methods given below, by the methods given in the examples or by analogous methods. Appropriate reaction conditions for the individual reaction steps are known to a person skilled in the art. Also, for reaction conditions described in literature affecting the described reactions see for example: *Comprehensive Organic Transformations: A Guide to Functional Group Preparations*, 2nd Edition, Richard C. Larock. John Wiley & Sons, New York, N.Y. 1999). We find it convenient to carry out the reactions in the presence or absence of a solvent. There is no particular restriction on the nature of the solvent to be employed, provided that it has no adverse effect on the reaction or the reagents involved and that it can dissolve the reagents, at least to some extent. The described reactions can take place over a wide range of temperatures, and the precise reaction temperature is not critical to the invention. It is convenient to carry out the described reactions in a temperature range between −78° C. to reflux. The time required for the reaction may also vary widely, depending on many factors, notably the reaction temperature and the nature of the reagents. However, a period of from 0.5 h to several days will usually suffice to yield the described intermediates and compounds. The reaction sequence is not limited to the one displayed in the schemes, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

The compounds of the present invention can be prepared, for example, by the general synthetic procedures described below.

In the following description and schemes, $R^1$-$R^8$ have the meaning as defined above unless indicated otherwise.

Following the procedure according to scheme 1, compound AA can be used as starting material (R=H, methyl, ethyl, isopropyl, tert-butyl or another suitable protecting group described for example in T. W. Greene et al., Protective Groups in Organic Chemistry, John Wiley and Sons Inc. New York 1999, $3^{rd}$ edition). AA is either commercially available, described in the literature, can be synthesized by a person skilled in the art or as described in the experimental part.

($R^4R^5$)—$R^6$ or H—$R^7$) by suitable amide bond forming reactions (step c). These reactions are known in the art. For example coupling reagents like N,N'-carbonyl-diimidazole (CDI), N,N'-dicyclohexylcarbodiimide (DCC), 1-(3-dimethylaminopropyl)-3-ethylcarbodiimide hydrochloride (EDCI), 1-[bis(dimethylamino)-methylene]-H-1,2,3-triazolo[4,5-b] pyridinium-3-oxide hexafluorophosphate (HATU), 1-hydroxy-1,2,3-benzotriazole (HOBT), O-benzotriazol-1-yl-N,N,N',N'-tetramethyluronium tetrafluoroborate (TBTU), and O-benzotriazole-N,N,N',N'-tetramethyl-uronium-hexafluoro-phosphate (HBTU) can be employed to affect such transformation. A convenient method is to use for example HBTU and a base, for example N-methylmorpholine in an inert solvent such as for example dimethylformamide at room temperature. Amines AE are either commercially available, described in the literature, can be synthesized by a person skilled in the art or as described in the experimental part.

Alternatively, compound AF can be used as starting material (R=H, methyl, ethyl, isopropyl, tert-butyl or another suitable protecting group described for example in T. W. Greene et al., Protective Groups in Organic Chemistry, John Wiley and Sons Inc. New York 1999, $3^{rd}$ edition). AF

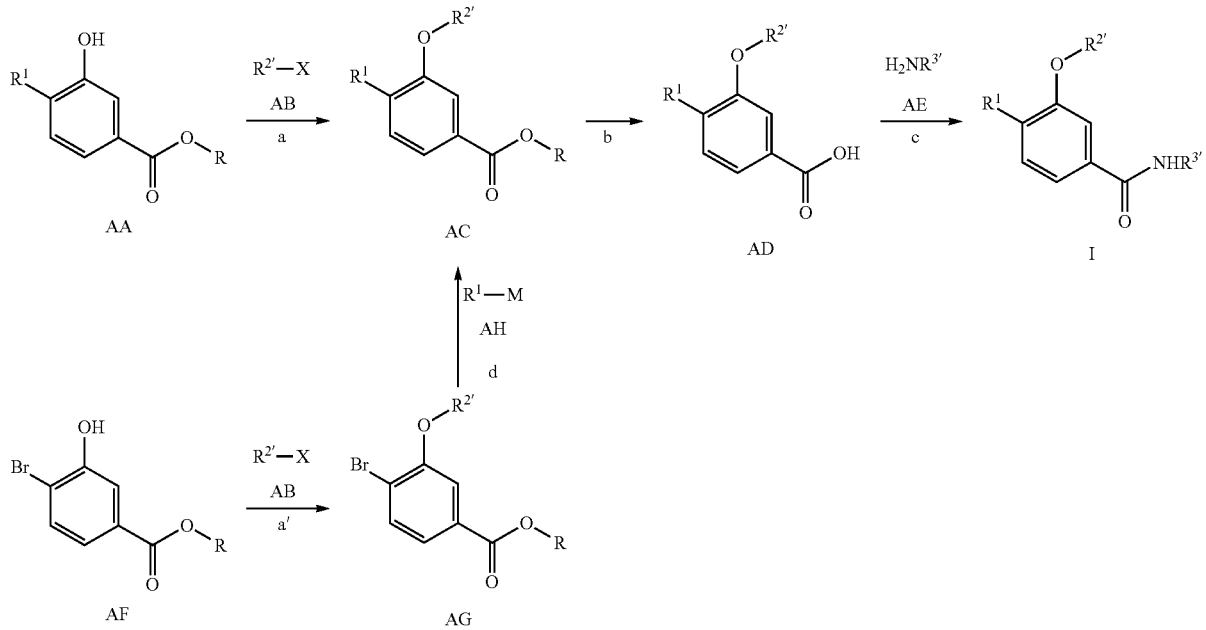

Scheme 1

Compound AC can be prepared from AA by reaction with a suitably substituted alkoxy or haloalkoxy derivative $R^{2'}$—X AB ($R^{2'}$=cyclopropylmethyl, alkyl, haloalkyl; X=Cl, Br or another suitable leaving group) in the presence of a base, for example potassium carbonate, in a solvent such as DMF, at temperatures ranging preferably ranging from room temperature to 50° C. (step a).

The saponification of the ester of general formula AC (R≠H) by methods well known to the ones skilled in the art—using e.g. aqueous LiOH, NaOH or KOH in tetrahydrofuran/ethanol or another suitable solvent at temperatures between 0° C. and the reflux temperature of the solvent employed—leads to an acid of general formula AD (step b).

Compound I can be prepared from acid AD and the corresponding amine $NH_2$—$R^{3'}$ AE ($NH_2$—$R^{3'}$ is $NH_2$—C is either commercially available, described in the literature, can be synthesized by a person skilled in the art or as described in the experimental part.

Compound AG can be prepared from AF by reaction with a suitably substituted alkoxy or haloalkoxy derivative $R^{2'}$—X AB ($R^{2'}$=cyclopropylmethyl, alkyl, haloalkyl; X=Cl, Br or another suitable leaving group) in the presence of a base, for example potassium carbonate, in a solvent such as DMF, at temperatures ranging preferably ranging from room temperature to 50° C. (step a').

Conversion of compound AG to compound AC can be prepared by coupling a suitably substituted cycloalkyl metal species $R^1$—M AH (e.g. a trifluoroborate $[BF_3]^-K^+$, a boronic acid $B(OH)_2$ or a boronic acid pinacol ester) in the presence of a suitable catalyst, in particular a palladium catalyst and more particularly palladium(II)acetate/triphenylphosphine or butyl-1-adamantylphosphin mixtures and a base such as cesium carbonate in in an inert solvent mixture like toluene/water preferably at the reflux temperature of the solvent mixture (step d). Alternatively, compound AG can be converted to amino derivatives AC by treatment with an amine R$^1$—M AH (M is H) applying methods well known in the art (step d), for example using a palladium promoted amination reaction with palladium(II)acetate/2-(dicyclohexylphosphino)biphenyl as the catalyst system in the presence of a base such as potassium carbonate in dioxane under reflux conditions.

If one of the starting materials, compounds of formulae AA, AB, AE, AF or AH, contains one or more functional groups which are not stable or are reactive under the reaction conditions of one or more reaction steps, appropriate protecting groups (P) (as described e.g. in T. W. Greene et al., Protective Groups in Organic Chemistry, John Wiley and Sons Inc. New York 1999, 3$^{rd}$ edition) can be introduced before the critical step applying methods well known in the art. Such protecting groups can be removed at a later stage of the synthesis using standard methods known in the art.

If one or more compounds of formulae AA to AH contain chiral centers, phenyls of formula I can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization or by separation of the antipodes by specific chromatographic methods using either a chiral adsorbent or a chiral eluent.

Following the procedure according to scheme 2, compound BA can be used as starting material (Y=Br, I; R=H, methyl, ethyl, isopropyl, tert-butyl or another suitable protecting group described for example in T. W. Greene et al., Protective Groups in Organic Chemistry, John Wiley and Sons Inc. New York 1999, 3$^{rd}$ edition). BA is either commercially available, described in the literature, can be synthesized by a person skilled in the art or as described in the experimental part.

Conversion of compound BA to compound BB can be prepared by coupling a suitably substituted cycloalkyl metal species R$^1$—M AH (e.g. a trifluoroborate [BF$_3$]$^-$K$^+$, a boronic acid B(OH)$_2$ or a boronic acid pinacol ester) or an amine R$^1$—M AH (M=H) as described in step d of scheme 1 (step a).

Bromination of phenyl BB following procedures well know to a person skilled in the art, e.g. by treatment with N-bromosuccinimide in the presence of trifluoroacetic acid at temperatures around 50° C., provides bromine BC (step b).

Compound BE can be prepared from BC by coupling a suitably substituted aryl or heteroaryl metal species R$^2$—M of formula BD (step c), e.g. an organotrifluoroborate potassium salt in the presence of a palladium catalyst such as palladium(II)acetate/butyl-1-adamantylphosphine and a base such as cesium carbonate in an inert solvent such as toluene at temperatures between 50° C. and the boiling temperature of the solvent, or an arylboronic acid or arylboronic acid ester in the presence of a suitable catalyst, in particular a palladium catalyst and more particularly palladium(II)acetate/triphenylphosphine mixtures or palladium (II)chloride-dppf (1,1'-bis(diphenylphosphino)ferrocene) complexes and abase such as triethylamine, sodium carbonate or potassium phosphate in an inert solvent such as dimethylformamide, toluene, tetrahydrofuran, acetonitrile or dimethoxyethane. Optionally, compound BD (M=H) can also be an amine which is coupled to BC by methods well known to a person skilled in the art (step c), e.g. using a palladium catalyst such as tris(dibenzylideneacetone)dipalladium/dimethylbisdiphenyl-phosphinoxanthene and a base such as cesium carbonate in a solvent such as 1,4-dioxane, preferentially at the boiling point of the solvent.

The saponification of the ester of general formula BE (R≠H) by methods well known to the ones skilled in the art—using e.g. aqueous LiOH, NaOH or KOH in tetrahydrofuran/ethanol or another suitable solvent at temperatures between 0° C. and the reflux temperature of the solvent employed—leads to an acid of general formula BF (step d).

Scheme 2

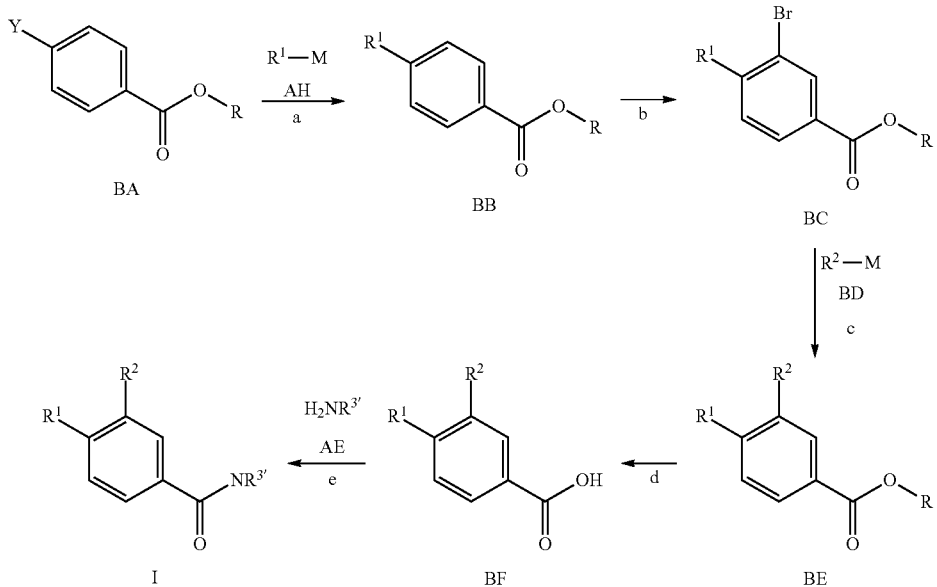

Compound I can be prepared from acid BF and the corresponding amine $NH_2$—$R^{3'}$ AE ($NH_2$—$R^{3'}$ is $NH_2$—C($R^4R^5$)—$R^6$ or H—$R^7$) by suitable amide bond forming reactions (step e). These reactions are known in the art. For example coupling reagents like N,N'-carbonyl-diimidazole (CDI), N,N'-dicyclohexylcarbodiimide (DCC), 1-(3-dimethylaminopropyl)-3-ethylcarbodiimide hydrochloride (EDCI), 1-[bis(dimethylamino)-methylene]-H-1,2,3-triazolo[4,5-b]pyridinium-3-oxide hexafluorophosphate (HATU), 1-hydroxy-1,2,3-benzotriazole (HOBT), O-benzotriazol-1-yl-N,N,N',N'-tetramethyluronium tetrafluoroborate (TBTU), and O-benzotriazole-N,N,N',N'-tetramethyl-uronium-hexafluoro-phosphate (HBTU) can be employed to affect such transformation. A convenient method is to use for example HBTU and a base, for example N-methylmorpholine in an inert solvent such as for example dimethylformamide at room temperature. Amines AE are either commercially available, described in the literature, can be synthesized by a person skilled in the art or as described in the experimental part.

If one of the starting materials, compounds of formulae BA, AH, BD or AE contains one or more functional groups which are not stable or are reactive under the reaction conditions of one or more reaction steps, appropriate protecting groups (P) (as described e.g. in T. W. Greene et al., Protective Groups in Organic Chemistry, John Wiley and Sons Inc. New York 1999, 3$^{rd}$ edition) can be introduced before the critical step applying methods well known in the art. Such protecting groups can be removed at a later stage of the synthesis using standard methods known in the art.

If one or more compounds of formulae BA to BF, AH or AE contain chiral centers, phenyls of formula I can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization or by separation of the antipodes by specific chromatographic methods using either a chiral adsorbent or a chiral eluent.

Following the procedure according to scheme 3, compound CA ($R^{8'}$=alkyl) can be used as starting material. CA is either commercially available, described in the literature, can be synthesized by a person skilled in the art or as described in the experimental part.

Scheme 3

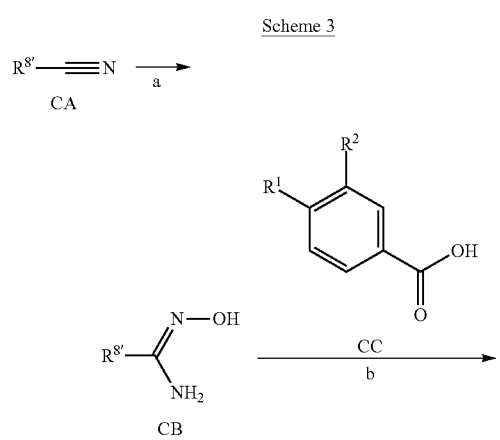

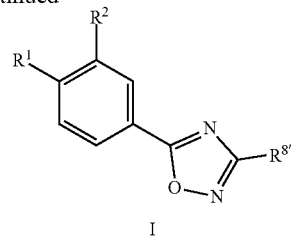

Compound CB can be obtained by reacting nitrile CA with hydroxylamine applying methods well know to a person skilled in the art (step a), e.g. via reaction with hydroxylamine hydrochloride in the presence of a base such as potassium carbonate in a solvent such as ethanol at temperatures between 0° C. and the reflux temperature of the solvent, preferentially at ambient temperature.

Condensation of acid CB (identical to compound AD in scheme 1 or compound BF in scheme 2) with hydroxyimide amide CB e.g. in the presence of carbonyldiimidazole in a solvent such as N,N-dimethylformamide at temperatures around 100° C. provides compound I (step b).

If the starting materials, compound of formulae CC contains one or more functional groups which are not stable or are reactive under the reaction conditions of one or more reaction steps, appropriate protecting groups (P) (as described e.g. in T. W. Greene et al., Protective Groups in Organic Chemistry, John Wiley and Sons Inc. New York 1999, 3$^{rd}$ edition) can be introduced before the critical step applying methods well known in the art. Such protecting groups can be removed at a later stage of the synthesis using standard methods known in the art.

If one or more compounds of formulae CA to CC contain chiral centers, phenyls of formula I can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization or by separation of the antipodes by specific chromatographic methods using either a chiral adsorbent or a chiral eluent.

Following the procedure according to scheme 4, compound DA can be used as starting material (R=methyl or another suitable protecting group described for example in T. W. Greene et al., Protective Groups in Organic Chemistry, John Wiley and Sons Inc. New York 1999, 3$^{rd}$ edition). DA is either commercially available, described in the literature, can be synthesized by a person skilled in the art or as described in the experimental part.

Scheme 4

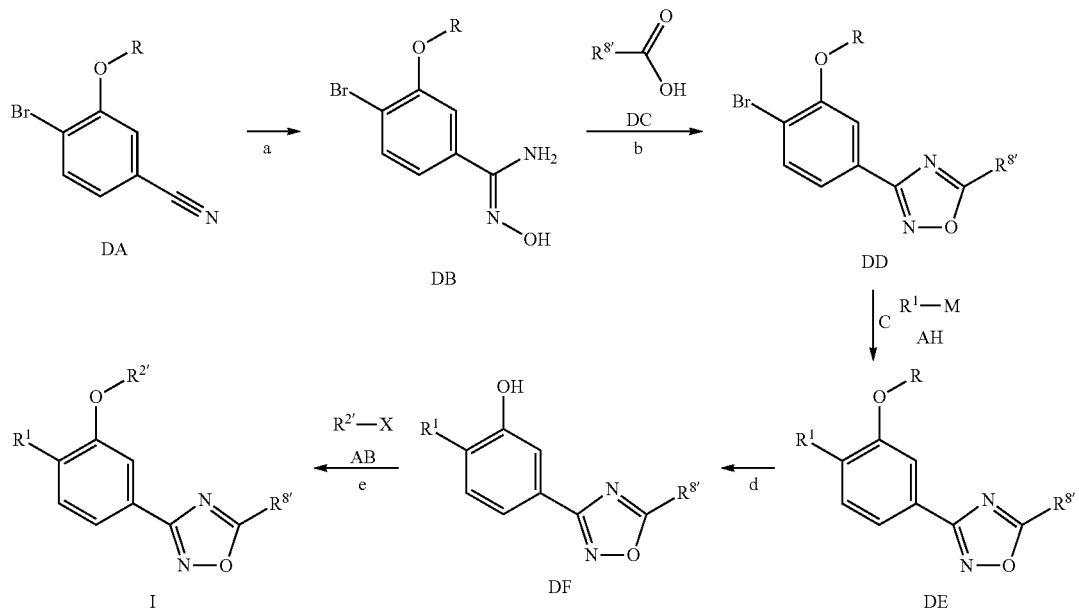

Compound DB can be prepared from DA by treatment with hydroxylamine hydrochloride in the presence of base such as triethylamine in a solvent such as ethanol similarly to the procedure described in step a of scheme 3 (step a).

Cyclisation of compound DB to compound DD can be performed by amide coupling methods known to a person skilled in the art, with the suitably substituted commercially available carboxylic acid DC($R^{8'}$=alkyl), followed by heating to cyclise to the oxadiazole ring in a high boiling point solvent such as DMF e.g. in analogy to the procedure described in step b of scheme 3 (step b).

Conversion of compound DD to compound DE can be prepared by coupling a suitably substituted cycloalkyl metal species $R^1$—M AH (e.g. a trifluoroborate $[BF_3]^-K^+$, a boronic acid $B(OH)_2$ or a boronic acid pinacol ester) in the presence of a suitable catalyst, in particular a palladium catalyst and more particularly palladium(II)acetate/triphenylphosphine or butyl-1-adamantylphosphin mixtures and a base such as cesium carbonate in in an inert solvent mixture like toluene/water preferably at the reflux temperature of the solvent mixture (step c). Alternatively, compound DD can be converted to amino derivatives DE by treatment with an amine $R^1$—M AH (M is H) applying methods well known in the art (step c), for example using a palladium promoted amination reaction with palladium(II)acetate/2-(dicyclohexylphosphino)biphenyl as the catalyst system in the presence of a base such as potassium carbonate in dioxane under reflux conditions.

Compound DE can be converted to the corresponding phenol compound DF applying deprotection methods known to a person skilled in the art, such as strong Lewis acids (e.g. $BBr_3$) in a suitable solvent like dichloromethane at room temperature for R equal to methyl (step d).

Compound I can be prepared from DF by reaction with a suitably substituted alkoxy or haloalkoxy derivative $R^{2'}$—X AB ($R^{2'}$=cyclopropylmethyl, alkyl, haloalkyl; X=Cl, Br or another suitable leaving group) in the presence of a base, for example potassium carbonate, in a solvent such as DMF, at temperatures ranging preferably from room temperature to 50° C. (step a).

If one of the starting materials, compounds of formulae DC, AH or AB contains one or more functional groups which are not stable or are reactive under the reaction conditions of one or more reaction steps, appropriate protecting groups (P) (as described e.g. in T. W. Greene et al., Protective Groups in Organic Chemistry, John Wiley and Sons Inc. New York 1999, 3$^{rd}$ edition) can be introduced before the critical step applying methods well known in the art. Such protecting groups can be removed at a later stage of the synthesis using standard methods known in the art.

If one or more compounds of formulae DC to DF, AH or AB contain chiral centers, phenyls of formula I can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization or by separation of the antipodes by specific chromatographic methods using either a chiral adsorbent or a chiral eluent.

The invention thus also relates to a process for the preparation of a compound of formula (I), comprising one of the following steps:

(a) The reaction of a compound of formula (A)

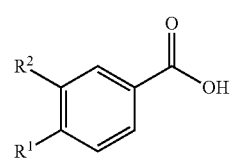

(A)

in the presence of $H_2N$—$C(R^4R^5)$—$R^6$, a coupling agent and a base, wherein $R^2$ is cyclopropylmethoxy, alkoxy or haloalkoxy;

(b) The reaction of a compound of formula (A) as defined above in the presence of H—$R^7$, a coupling agent and a base, wherein $R^2$ is cyclopropylmethoxy, alkoxy or haloalkoxy;

(c) The reaction of a compound of formula (A) as defined above in the presence of a compound of formula (B)

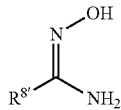
(B)

and carbonyldiimidazole, wherein $R^{8'}$ is methyl or tert.-butyl; or (d) The reaction of a compound of formula (C)

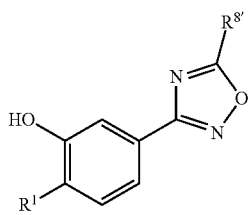
(C)

in the presence of $R^{2'}$—X, wherein $R^{2'}$ is cyclopropylmethyl, alkyl or haloalkyl, $R^{8'}$ is methyl or tert.-butyl and X is a leaving group.

In steps (a) and (b), the coupling agent is for example N,N'-carbonyl-diimidazole (CDI), N,N'-dicyclohexylcarbodiimide (DCC), 1-(3-dimethylaminopropyl)-3-ethylcarbodiimide hydrochloride (EDCI), 1-[bis(dimethylamino)-methylene]-H-1,2,3-triazolo[4,5-b]pyridinium-3-oxide hexafluorophosphate (HATU), 1-hydroxy-1,2,3-benzotriazole (HOBT), O-benzotriazol-1-yl-N,N,N',N'-tetramethyl-uronium tetrafluoroborate (TBTU) or O-benzotriazole-N,N,N',N'-tetramethyl-uronium-hexafluoro-phosphate (HBTU). The base is for example N-methylmorpholine. A convenient method is to use for example HBTU and a base, for example N-methylmorpholine in an inert solvent such as for example dimethylformamide at room temperature.

In step (d), the leaving group is for example chlorine or bromine.

The invention also relates to a compound of formula (I) when manufactured according to a process of the invention.

The invention also relates in particular to:

A compound of formula (I) for use as therapeutically active substance;

A pharmaceutical composition comprising a compound of formula (I) and a therapeutically inert carrier;

The use of a compound of formula (I) for the treatment or prophylaxis of pain, atherosclerosis, age-related macular degeneration, diabetic retinopathy, glaucoma, retinal vein occlusion, retinopathy of prematurity, ocular ischemic syndrome, geographic atrophy, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, neurodegeneration, amyotrophic lateral sclerosis, stroke, transient ischemic attack or uveitis;

The use of a compound according of formula (I) for the preparation of a medicament for the treatment or prophylaxis of pain, atherosclerosis, age-related macular degeneration, diabetic retinopathy, glaucoma, retinal vein occlusion, retinopathy of prematurity, ocular ischemic syndrome, geographic atrophy, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, neurodegeneration, amyotrophic lateral sclerosis, stroke, transient ischemic attack or uveitis;

A compound of formula (I) for use in the treatment or prophylaxis of pain, atherosclerosis, age-related macular degeneration, diabetic retinopathy, glaucoma, retinal vein occlusion, retinopathy of prematurity, ocular ischemic syndrome, geographic atrophy, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, neurodegeneration, amyotrophic lateral sclerosis, stroke, transient ischemic attack or uveitis; and A method for the treatment or prophylaxis of pain, atherosclerosis, age-related macular degeneration, diabetic retinopathy, glaucoma, retinal vein occlusion, retinopathy of prematurity, ocular ischemic syndrome, geographic atrophy, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, neurodegeneration, amyotrophic lateral sclerosis, stroke, transient ischemic attack or uveitis, which method comprises administering an effective amount of a compound of formula (I) to a patient in need thereof.

The invention particularly relates to a compound of formula (I) for the treatment or prophylaxis of ischemia, reperfusion injury, liver fibrosis or kidney fibrosis, in particular ischemia or reperfusion injury.

The invention further particularly relates to a compound of formula (I) for the treatment or prophylaxis of diabetic retinopathy, retinal vein occlusion or uveitis.

The invention is further directed to a compound of formula (I), when manufactured according to a process according to the invention.

Another embodiment of the invention provides a pharmaceutical composition or medicament containing a compound of the invention and a therapeutically inert carrier, diluent or excipient, as well as a method of using the compounds of the invention to prepare such composition and medicament. In one example, the compound of formula (I) may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula (I) is formulated in an acetate buffer, at pH 5. In another embodiment, the compound of formula (I) is sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration. The compounds of the invention may be administered in particular by intravitreal administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

The invention will now be illustrated by the following examples which have no limiting character.

EXAMPLES

Abbreviations

MS=mass spectrometry; EI=electron ionization; ESI=electrospray; CAN=CAS Registry Number; CDI=1,1'-carbonyl diimidazole; DCM=dichloromethane; DIEA=N-ethyl-N-isopropylpropan-2-amine; DBU=1,8-Diazabicyclo[5.4.0]undec-7-ene; DMF=dimethylformamide; DMSO=dimethyl-sulfoxide; EtOAc=ethyl acetate; HPLC=LC=high performance liquid chromatography; iPrOAc=isopropyl acetate; TBME=methyl tert-butylether; TBTU=O-(benzotriazol-1-yl)-N,N,N',N'-tetramethyl-uronium-tetrafluoroborate; THF=tetrahydrofuran; tlc=thin layer chromatography.

Example 1

N-[(2S)-1-amino-4-methyl-1-oxopentan-2-yl]-3-(cyclopropylmethoxy)-4-methylbenzamide

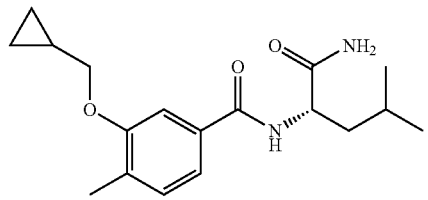 [SMILES: Cc1ccc(C(=O)N[C@@H](CC(C)C)C(N)=O)cc1OCC1CC1]

a) Methyl 3-(cyclopropylmethoxy)-4-methylbenzoate

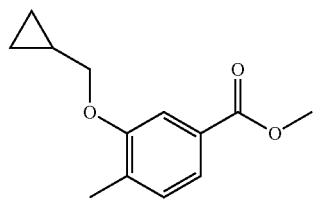 [SMILES: COC(=O)c1ccc(C)c(OCC2CC2)c1]

Methyl 3-hydroxy-4-methylbenzoate (CAN 3556-86-3; 1 g, 6.02 mmol) was dissolved in DMF (10 mL). (Bromomethyl)cyclopropane (CAN 7051-34-5, 894 mg, 579 μL, 6.62 mmol) and potassium carbonate (1.66 g, 12.0 mmol) were added. The reaction mixture was stirred for 20 h, poured into 25 mL 1 M HCl and extracted with iPrOAc (2×25 mL). The organic layers were washed with ice/brine (2×20 mL), dried over Na$_2$SO$_4$ and concentrated in vacuo to give 1.1 g of a light yellow oil. The crude material was purified by flash chromatography (20 g silica gel, 0 to 10% heptane/iPrOAc) to give 880 mg (3.99 mmol, 66%) of the title compound as colorless oil. MS: m/e=221.3 [M+H]$^+$.

b) 3-(Cyclopropylmethoxy)-4-methylbenzoic acid

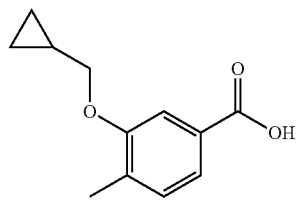

Methyl 3-(cyclopropylmethoxy)-4-methylbenzoate (880 mg, 4 mmol) was dissolved in THF (8.8 mL) and water (4.4 mL). Lithium hydroxide monohydrate (201 mg, 4.79 mmol) was added. The reaction mixture was stirred for 60 h at ambient temperature, poured into 1 M HCl (100 mL) and extracted with i/ProAc) (200 mL). The organic layer was washed with ice/water/sat. NaCl (3×100 mL), dried over Na$_2$SO$_4$ and concentrated in vacuo to give 830 mg (4 mmol, quant.) of the title compound as colorless solid. MS:=204.9 [M−H]$^-$.

c) N-[(2S)-1-amino-4-methyl-1-oxopentan-2-yl]-3-(cyclopropylmethoxy)-4-methylbenzamide A mixture of 3-(cyclopropylmethoxy)-4-methylbenzoic acid (20 mg, 97.0 μmol), (R)-2-amino-4-methylpentanamide hydrochloride (CAN 80970-09-8; 17.8 mg, 107 μmol), 2-(3H-[1,2,3]triazolo[4,5-b]pyridin-3-yl)-1,1,3,3-tetramethylisouronium hexafluorophosphate(V) (73.7 mg, 194 μmol) and N-ethyl-N-isopropylpropan-2-amine (37.6 mg, 50.8 μL, 291 μmol) in DMF (235 μL) was stirred for 18 h at ambient temperature. The reaction mixture was poured onto 1 M HCl/ice/water (1×20 mL), extracted with iPrOAc (2×25 mL) and washed with ice/water (2×25 mL) to pH 6. The organic layers were dried over Na$_2$SO$_4$ and evaporated under reduced pressure. The crude material was purified by preparative TLC (silica gel, 2.0 mm, heptane/iPrOAc 1:2), eluted with iPrOAc, filtered out and evaporated to give 21 mg of the title compound. MS: 319.1 [M+H]$^+$.

Example 2

3-(Cyclopropylmethoxy)-4-methyl-N-[2-(5-methyl-1,2,4-oxadiazol-3-yl)propan-2-yl]benzamide

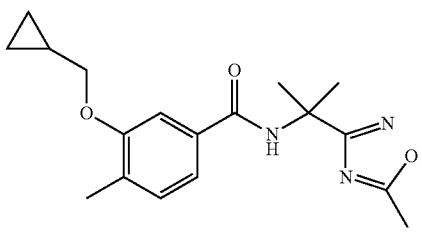 [SMILES: C/C(O)=N/C(=N)C(C)(C)NC(=O)c1ccc(C)c(OCC2CC2)c1]

A mixture of 3-(cyclopropylmethoxy)-4-methylbenzoic acid (Example 1b; 20 mg, 97.0 μmol), 2-(5-methyl-1,2,4-oxadiazol-3-yl)propan-2-amine hydrochloride (CAN 1240526-27-5; 17.2 mg, 97.0 μmol), TBTU (46.7 mg, 145 μmol) and N,N-diisopropylethylamine (62.7 mg, 83.0 μL, 485 μmol) in DMF (647 μL) was stirred under argon for 18 h at ambient temperature. The reaction mixture was poured in 30 mL ice/water, extracted with iPrOAc (2×40 mL) and washed with 30 mL icewater/brine. The organic layers were combined, dried over Na$_2$SO$_4$ and concentrated in vacuo to give 45 mg of a light brown oil. The crude material was purified by preparative TLC (silica gel, 2.0 mm, iPrOAc) and eluted with iPrOAc/DCM 1:1 to give 28 mg of the title compound as a white solid. MS: 330.1 [M+H]$^+$.

Example 3

4-Cyclopropyl-3-(cyclopropylmethoxy)-N-[2-(5-methyl-1,2,4-oxadiazol-3-yl)propan-2-yl]benzamide

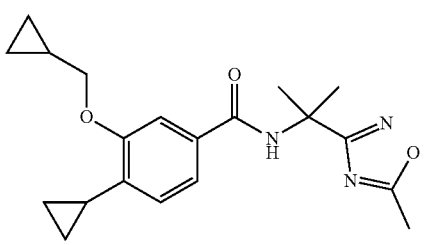 [SMILES: C/C(O)=N/C(=N)C(C)(C)NC(=O)c1ccc(C2CC2)c(OCC2CC2)c1]

a) 4-Bromo-3-cyclopropylmethoxy-benzoic acid ethyl ester

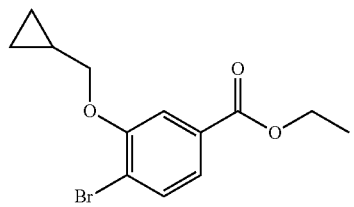 [SMILES: CCOC(=O)c1ccc(Br)c(OCC2CC2)c1]

A mixture of ethyl 4-bromo-3-hydroxybenzoate (CAN 33141-66-1; 4.85 g, 19.8 mmol) (bromomethyl)cyclopropane (CAN 7051-34-5, 3.21 g, 2.27 mL, 23.7 mmol) and potassium carbonate (6.56 g, 47.5 mmol) in N,N-dimethylformamide (50 mL) was heated to 50° C. for 19 h. The reaction mixture was poured into H$_2$O (200 mL) and extracted with iPrOAc (2×200 mL). The organic layers were washed with ice/sat. NaCl (2×150 mL), dried over Na$_2$SO$_4$ and concentrated in vacuo to give 6.35 g of a light yellow liquid. 500 mg were purified by flash chromatography to give 293 mg of the title compound as colorless liquid. MS: 301.0 [M+H]$^+$.

b) Ethyl 4-cyclopropyl-3-(cyclopropylmethoxy)benzoate

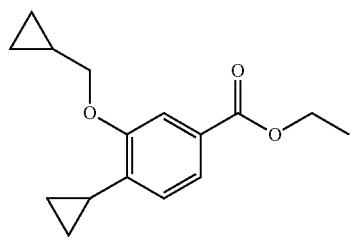 [SMILES: CCOC(=O)c1ccc(C2CC2)c(OCC2CC2)c1]

Palladium(II) acetate (7.5 mg, 33.4 μmol), butyl-1-adamantylphosphin (18.0 mg, 50.1 μmol), potassium cyclopropyltrifluoroborate (CAN 1065010-87-8; 250 mg, 1.69 mmol) and cesium carbonate (1.63 g, 5.01 mmol) were combined to give a white solid. To this solid a solution of 4-bromo-3-cyclopropylmethoxy-benzoic acid ethyl ester (500 mg, 1.67 mmol) in toluene (12.6 mL) and water (1.4 mL) (evacuated and flushed with argon) was added through a septum cap. The reaction mixture was heated to 120° C. for 20 h. After cooling to ambient temperature the crude was diluted with H$_2$O (10 mL). The reaction mixture was poured onto 100 mL ice/brine and extracted with iPrOAc (2×200 mL). The combined organic layers were washed with ice/brine (100 mL), dried over Na$_2$SO$_4$ and concentrated in vacuo. The crude product was purified by flash-chromatography with a heptan/iPrOAc gradient to give 283 mg of the title compound. MS: m/e=261.3 [M+H]$^+$.

c) 4-Cyclopropyl-3-(cyclopropylmethoxy)benzoic acid

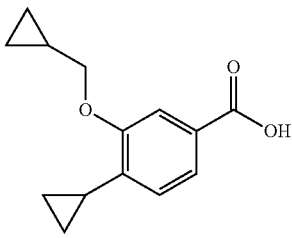 [SMILES: O=C(O)c1ccc(C2CC2)c(OCC2CC2)c1]

Ethyl 4-cyclopropyl-3-(cyclopropylmethoxy)benzoate (311 mg, 1.19 mmol) and lithium hydroxide hydrate (60.2 mg, 1.43 mmol) were combined with THF (2.5 mL) and water (625 µL) to give a yellow solution which was stirred for 24 h at ambient temperature. Lithium hydroxide hydrate (60.2 mg, 1.43 mmol) was added and stirring was continued for 24 h. The reaction mixture was poured onto ice/water/1N NaOH (20 mL) and extracted with TBME (2×30 mL). The combined extracts were washed with ice/water (20 mL), dried over $Na_2SO_4$ and concentrated in vacuo to give 49 mg of a yellow oil. The aqueous layer was acidified with 1N HCl (3 mL). A precipitate formed which was filtered off to give 166 mg of a light brown solid. The aqueous layer was back extracted with EtOAc (2×30 mL). The organic layers were washed with ice/water (20 mL), combined, dried over $Na_2SO_4$ and concentrated in vacuo to give 20 mg of the title compound as a yellow solid. MS(ESI): m/e=231.3 [M−H]⁻.

d) 4-Cyclopropyl-3-(cyclopropylmethoxy)-N-[2-(5-methyl-1,2,4-oxadiazol-3-yl)propan-2-yl]benzamide A mixture of 4-cyclopropyl-3-(cyclopropylmethoxy)benzoic acid (10 mg, 43.1 µmol), 2-(5-methyl-1,2,4-oxadiazol-3-yl)propan-2-amine hydrochloride (CAN 1240526-27-5; 8.41 mg, 47.4 µmol), TBTU (20.7 mg, 64.6 µmol) and N,N-diisopropylethylamine (27.8 mg, 36.8 µL, 215 µmol) in DMF (287 µL) was stirred under argon for 18 h at ambient temperature. The reaction mixture was poured in 30 mL ice/water and extracted with iPrOAc (2×40 mL). The combined extracts were washed with 30 mL ice/water/brine, dried over $Na_2SO_4$ and concentrated in vacuo to give 45 mg of a brown oil. The crude material was purified by prep. TLC (silica gel, 2 mm, iPrOAc) and eluted in DCM/iPrOAc 1:1 to give 6 mg of the title compound as light yellow solid. MS: 356.1 [M+H]⁺.

Example 4

N²-[4-Cyclopropyl-3-(cyclopropylmethoxy)benzoyl]-L-leucinamide

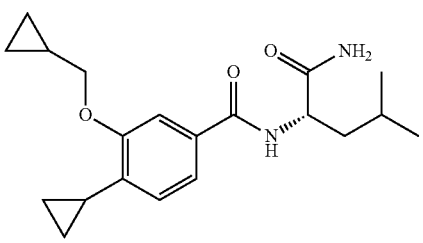 [SMILES: CC(C)C[C@H](NC(=O)c1ccc(C2CC2)c(OCC2CC2)c1)C(N)=O]

The title compound was synthesized in analogy to Example 3d, using 4-cyclopropyl-3-(cyclopropylmethoxy)benzoic acid and (S)-2-amino-4-methylpentanamide hydrochloride (CAN 10466-61-2) as starting materials, and directly purified by preparative HPLC without any work-up. MS (ESI, m/z): 345.1 [M+H]⁺.

Example 5

4-Cyclopropyl-3-(cyclopropylmethoxy)-N-(1-hydroxy-2-methylpropan-2-yl)benzamide

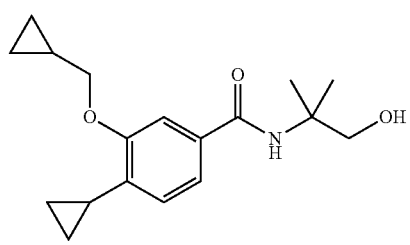 [SMILES: CC(C)(CO)NC(=O)c1ccc(C2CC2)c(OCC2CC2)c1]

The title compound was synthesized in analogy to Example 3d, using 4-cyclopropyl-3-(cyclopropylmethoxy)benzoic acid and 2-amino-2-methylpropan-1-ol (CAN 124-68-5) as starting materials, and directly purified by preparative HPLC without any work-up. MS (ESI, m/z): 304.1 [M+H]⁺.

Example 6

4-Cyclopropyl-3-(cyclopropylmethoxy)-N-[2-(1,3-thiazol-2-yl)propan-2-yl]benzamide

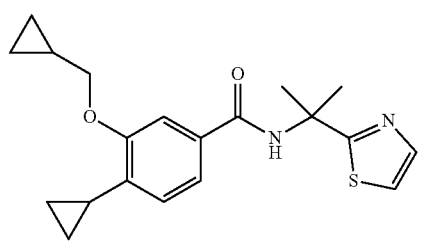 [SMILES: CC(C)(NC(=O)c1ccc(C2CC2)c(OCC2CC2)c1)c1nccs1]

The title compound was synthesized in analogy to Example 3d, using 4-cyclopropyl-3-(cyclopropylmethoxy)benzoic acid and 2-(thiazol-2-yl)propan-2-amine (CAN 1082393-38-1) as starting materials. The reaction mixture was poured into 20 mL ice/water, extracted with iPrOAc (2×30 ml) and washed with 20 mL ice/water/brine. The organic layers were combined, dried over $Na_2SO_4$ and concentrated in vacuo to give 29 mg of a light yellow solid. The crude material was purified by prep. TLC (silica gel, 2 mm, heptane/iPrOAc, 1:1) and eluted in DCM/iPrOAc 1:1 to afford 15 mg of the title compound as a white solid. MS (ESI, m/z): 357.1 [M+H]⁺.

Example 7

Ethyl 2-[4-cyclopropyl-3-(cyclopropylmethoxy)benzamido]-2-ethylbutanoate

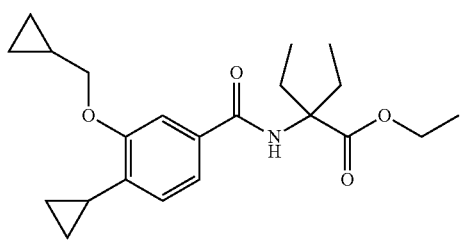 [SMILES: CCOC(=O)C(CC)(CC)NC(=O)c1ccc(C2CC2)c(OCC2CC2)c1]

The title compound was synthesized in analogy to Example 3d, using 4-cyclopropyl-3-(cyclopropylmethoxy) benzoic acid and ethyl 2-amino-2-ethylbutanoate hydrochloride (CAN 1135219-29-2) as starting materials. The reaction mixture was stirred for 4 days at ambient temperature, poured onto 1 M HCl/ice/water/brine (25 mL) and extracted with EtOAc (2×30 mL). The organic layers were combined and washed with ice/water/brine (25 mL), dried over Na$_2$SO$_4$ and concentrated in vacuo to give 122 mg of a yellow solid. The crude material was purified by prep. TLC (silica gel, 2×2.0 mm, heptane/EtOAc 4:1) and eluted in DCM/EtOAc 1:1 to give 30 mg of the title compound as a white solid. MS: 374.3 [M+H]$^+$.

Example 8

2-[4-Cyclopropyl-3-(cyclopropylmethoxy)benzamido]-2-ethylbutanoic acid

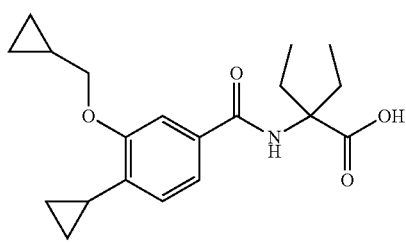 [SMILES: CCC(CC)(NC(=O)c1ccc(C2CC2)c(OCC2CC2)c1)C(=O)O]

A mixture of ethyl 2-[4-cyclopropyl-3-(cyclopropylmethoxy)benzamido]-2-ethylbutanoate (Example 7; 25 mg, 66.9 µmol) and sodium hydroxide (268 µL, 268 µmol) in THF (266 µL) and MeOH (266 µL) was stirred at 100° C. for 40 h. The reaction mixture was poured onto ice/water/brine/1N HCl (25 mL) and extracted with EtOAc (2×30 mL). The combined extracts were washed with ice/water/brine (25 mL), dried over Na$_2$SO$_4$ and concentrated in vacuo to give 22 mg of the title compound as a light yellow solid. MS: 344.3 [M−H]$^−$.

Example 9

4-Cyclopropyl-3-(cyclopropylmethoxy)-N-[3-(3,3-difluoroazetidine-1-carbonyl)pentan-3-yl]benzamide

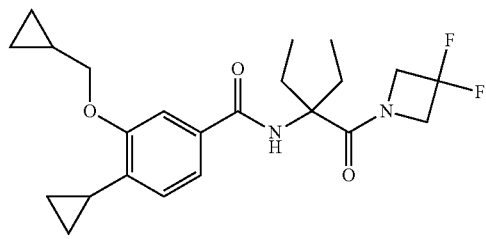 [SMILES: CCC(CC)(NC(=O)c1ccc(C2CC2)c(OCC2CC2)c1)C(=O)N1CC(F)(F)C1]

A mixture of 2-(4-cyclopropyl-3-(cyclopropylmethoxy)benzamido)-2-ethylbutanoic acid (Example 8; 12 mg, 34.7 µmol), 3,3-difluoroazetidine hydrochloride (CAN 288315-03-7; 5.4 mg, 41.7 µmol), 1-hydroxybenzotriazole hydrate (10.6 mg, 69.5 µmol) and DIEA (18 mg, 23.8 µL, 139 µmol) in DMF (120 µL) was stirred for 20 h at ambient temperature. The reaction mixture was poured onto icewater/brine/1 mL 1 N HCl (20 mL) and extracted with EtOAc (2×30 mL). The combined extracts were washed with ice/water/brine (20 mL), dried over Na$_2$SO$_4$ and concentrated in vacuo to give 22 mg of a light yellow solid. The crude material was purified by prep. TLC (silica gel, 1 mm, heptane/EtOAc 1:1) and eluted in DCM/EtOAc 1:1 to give 7 mg of the title compound as a white solid. 421.2 [M+H]$^+$.

Example 10

3-(Cyclopropylmethoxy)-4-(3,3-difluoroazetidin-1-yl)-N-[2-(5-methyl-1,2,4-oxadiazol-3-yl)propan-2-yl]benzamide

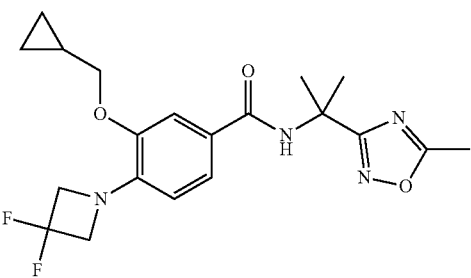 [SMILES: Cc1nc(C(C)(C)NC(=O)c2ccc(N3CC(F)(F)C3)c(OCC3CC3)c2)no1]

a) 4-Bromo-3-cyclopropylmethoxy-benzoic acid methyl ester

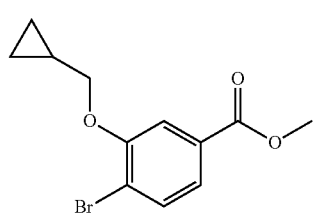 [SMILES: COC(=O)c1ccc(Br)c(OCC2CC2)c1]

The title compound was synthesized in analogy to Example 3a, using methyl 4-bromo-3-hydroxybenzoate (CAN 106291-80-9) and (bromomethyl)cyclopropane (CAN 7051-34-5). MS: 285.0 [M+H]+.

b) 3-Cyclopropylmethoxy-4-(3,3-difluoro-azetidin-1-yl)-benzoic acid methyl ester

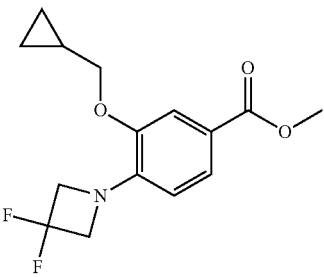 [SMILES: COC(=O)c1ccc(N2CC(F)(F)C2)c(OCC2CC2)c1]

Methyl 4-bromo-3-(cyclopropylmethoxy)benzoate (500 mg, 1.75 mmol) was dissolved in toluene (28 mL). 3,3-Difluoroazetidine hydrochloride (CAN 288315-03-7; 250 mg, 1.93 mmol), cesium carbonate (1.43 g, 4.38 mmol), racemic-2,2'-bis(diphenylphosphino)-1,1'-binaphtyl (76.4 mg, 123 µmol) and palladium (II) acetate (19.7 mg, 87.7 µmol) were added under argon. The resulting reaction mixture was heated to 110° C. for 16 h. After cooling to room temperature EtOAc (40 mL) was added. The mixture was poured onto icewater/1N HCl/brine (80 mL) and extracted with EtOAc. The organic layers back-washed with brine, dried over Na₂SO₄, filtered and concentrated in vacuo. The crude material was purified by flashmaster chromatography (silica gel, 50 g, gradient of EtOAc in heptane).

c) 3-(Cyclopropylmethoxy)-4-(3,3-difluoroazetidin-1-yl)benzoic acid

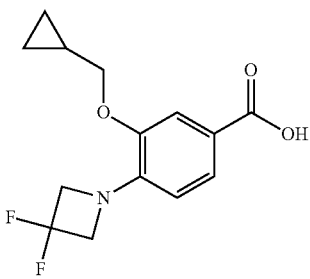 [SMILES: O=C(O)c1ccc(N2CC(F)(F)C2)c(OCC2CC2)c1]

Methyl 3-(cyclopropylmethoxy)-4-(3,3-difluoroazetidin-1-yl)benzoate (356 mg, 1.2 mmol) was combined with tetrahydrofuran (21 mL) and water (7 mL) to give a colorless solution. Lithium hydroxide monohydrate (151 mg, 3.59 mmol) was added and the resulting reaction mixture was stirred under reflux conditions for 24 h. After cooling to room temperature water (10 mL) was added. The reaction mixture was acidified with 1N HCl (pH=2) and extracted with TBME (100 mL). The aqueous layer was back extracted with TBME. The combined organic phases were dried on Na₂SO₄ and concentrated in vacuo to afford 320 mg of the title compound as off-white solid. MS: 284.3 [M+H]+.

d) 3-(Cyclopropylmethoxy)-4-(3,3-difluoroazetidin-1-yl)-N-[2-(5-methyl-1,2,4-oxadiazol-3-yl)propan-2-yl]benzamide A mixture of 3-(cyclopropylmethoxy)-4-(3,3-difluoroazetidin-1-yl)benzoic acid (50 mg, 177 µmol), DIEA (114 mg, 154 µL, 883 µmol), TBTU (62.3 mg, 194 µmol) and 2-(5-methyl-1,2,4-oxadiazol-3-yl)propan-2-amine (CAN 1153831-97-0; 27.4 mg, 194 µmol) in DMF (2 mL) was stirred at ambient temperature overnight. After concentration in vacuo (high vac., 40° C., 30 min) the residue was dissolved in EtOAc (3 mL). 2N NaOH was added. The mixture was stirred for 1 minute and poured into a 10 g Varian chemElut-column. After 10 minutes the column was washed with EtOAc (40 mL) and the solution was concentrated in vacuo. The crude material was purified by flash chromatography (silica gel, 10 g, gradient of EtOAc in heptane) to give the title compound. MS: 407.18 [M+H]+.

Example 11

N-[2-(5-Amino-1,2,4-oxadiazol-3-yl)propan-2-yl]-3-(cyclopropylmethoxy)-4-(3,3-difluoroazetidin-1-yl)benzamide

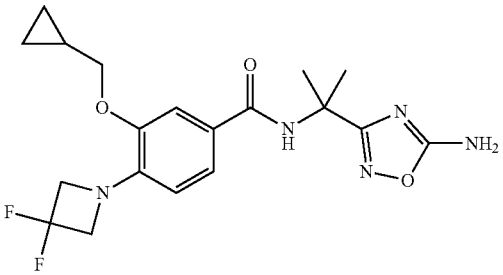 [SMILES: CC(C)(NC(=O)c1ccc(N2CC(F)(F)C2)c(OCC2CC2)c1)c1noc(N)n1]

The title compound was synthesized in analogy to Example 10d, using 3-(cyclopropylmethoxy)-4-(3,3-difluoroazetidin-1-yl)benzoic acid (Example 10c) and 1-(5-amino-[1,2,4]oxadiazol-3-yl)-1-methyl-ethyl-ammonium chloride (CAN 1415899-80-7) as starting materials. The crude reaction mixture was concentrated in vacuo. The residue was stirred with EtOAc (3 mL). 2N NaOH was added. Methanol (1 mL) was added to the EtOAc layer to dissolve the solid after separation. The organic phase was dried with Na₂SO₄, filtered and concentrated in vacuo. The crude product was stirred with EtOAc at reflux and slowly cooled to room temperature. The precipitating title compound was collected by filtration. MS: 408.18 [M+H]+.

Example 12

N²-[3-(cyclopropylmethoxy)-4-(3,3-difluoroazetidin-1-yl)benzoyl]-N-methyl-L-leucinamide

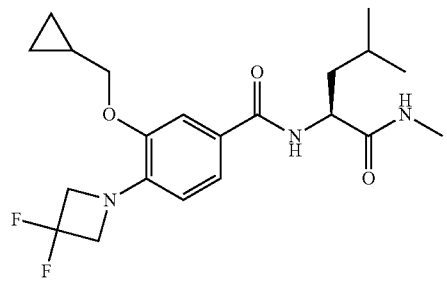 [SMILES: CNC(=O)[C@H](CC(C)C)NC(=O)c1ccc(N2CC(F)(F)C2)c(OCC2CC2)c1]

The title compound was synthesized in analogy to Example 10d, using 3-(cyclopropylmethoxy)-4-(3,3-difluoroazetidin-1-yl)benzoic acid (Example 10c) and (S)-2-amino-N,4-dimethylpentanamide hydrochloride (CAN 99145-71-8) as starting materials. The crude product was concentrated in vacuo (high vacuum, 40° C.). The residue was dissolved in EtOAc (3 mL). 2N NaOH was added. The mixture was stirred for 1 minute and poured into a 10 g Varian chemElut-column. After 10 minutes the column was washed with EtOAc (40 mL). The crude mixture was concentrated in vacuo and purified by flash chromatography (silica gel, 10 g, gradient of EtOAc in heptane) to give 35 mg of the title compound as white solid. MS: 410.22 [M+H]+.

Example 13

3-(Cyclopropylmethoxy)-4-(3,3-difluoroazetidin-1-yl)-N-[(2S)-1-hydroxy-4-methylpentan-2-yl]benzamide

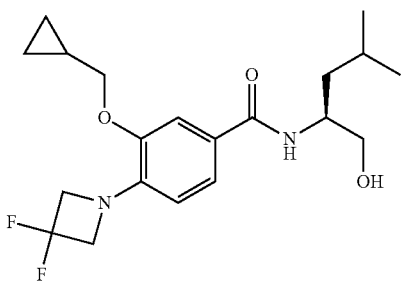 [SMILES: CC(C)C[C@@H](CO)NC(=O)c1ccc(N2CC(F)(F)C2)c(OCC2CC2)c1]

The title compound was synthesized in analogy to Example 10d, using 3-(cyclopropylmethoxy)-4-(3,3-difluoroazetidin-1-yl)benzoic acid (Example 10c) and (S)-2-amino-4-methylpentan-1-ol (CAN 7533-40-6) as starting materials. The crude mixture was concentrated in vacuo (high vac., 40° C.). The residue was dissolved in EtOAc (3 mL). 2N NaOH was added. The solution was stirred 1 minute and poured into a 10 g Varian chemElut-column. After 10 minutes the column was washed with EtOAc (40 mL). The solvent was evaporated in vacuo and the crude material purified by flash chromatography (silica gel, 10 g, gradient of EtOAc in heptane) to give 37 mg of the title compound as white solid. MS: 383.21 [M+H]+.

Example 14

3-tert-Butyl-5-[4-cyclopropyl-3-(cyclopropylmethoxy)phenyl]-1,2,4-oxadiazole

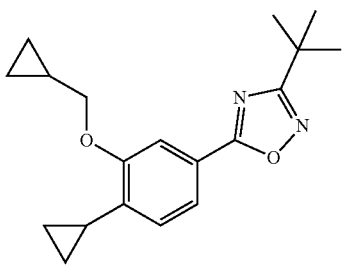 [SMILES: CC(C)(C)c1noc(-c2ccc(C3CC3)c(OCC3CC3)c2)n1]

To a solution of 4-cyclopropyl-3-(cyclopropylmethoxy)benzoic acid (Example 3c; 15 mg, 64.6 µmol) in dry DMF (0.643 mL) CDI (15.7 mg, 96.9 µmol) was added. The mixture was stirred for 30 min at ambient temperature. (E)-N'-hydroxypivalimidamide (CAN 1240301-71-6; 11.3 mg, 96.9 µmol) was added and stirring at ambient temperature was continued for 1 h. The temperature was raised to 100° C. After 72 h the mixture was cooled to room temperature and directly purified by preparative HPLC without any work-up to give 13 mg of the title compound. MS (ESI) m/e=313.5 [M+H]+.

Example 15

N-[3-(2-Amino-2-oxoethyl)oxetan-3-yl]-4-cyclopropyl-3-(cyclopropylmethoxy)benzamide

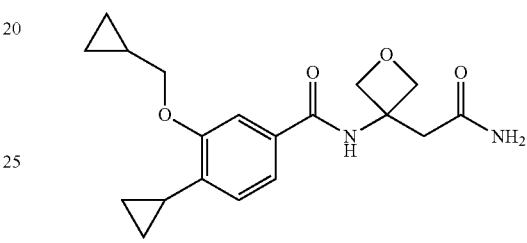

The title compound was synthesized in analogy to Example 3d, using 4-cyclopropyl-3-(cyclopropylmethoxy)benzoic acid (Example 3c) and 2-(3-amino-oxetan-3-yl)-acetamide (CAN 1417638-25-5) as starting materials in the presence of DIEA in THF. The reaction mixture was poured onto ice/water/1N HCl (20 mL) and extracted with EtOAc (2×40 mL). The combined organic layers were washed with ice/water (20 mL), dried over Na2SO4 and concentrated in vacuo to give 22 mg of a white solid. The crude material was purified by preparative TLC (silica gel, 1.0 mm, heptane/EtOAc 1:1) and eluted in CH2Cl2/EtOAc 1:1 to give 10 mg of the title compound as a white solid. MS(ESI): m/e=345.2 [M+H]+.

Example 16

N-[3-(2-Amino-2-oxoethyl)-1,1-dioxothietan-3-yl]-4-cyclopropyl-3-(cyclopropylmethoxy)benzamide

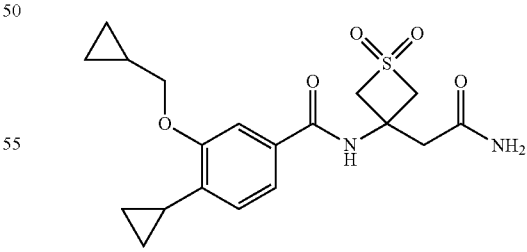

The title compound was synthesized in analogy to Example 3d, using 4-cyclopropyl-3-(cyclopropylmethoxy)benzoic acid (Example 3c) and 2-(3-amino-1,1-dioxo-thietan-3-yl)acetamide (CAN 1613239-56-7) as starting materials. The reaction mixture was stirred for 1 day at ambient temperature. The reaction mixture was poured onto ice/water/1M HCl (20 mL) and extracted with EtOAc (2×30 mL). The combined extracts were washed with ice/water/brine (20 mL), dried over Na$_2$SO$_4$ and concentrated in vacuo to give 39 mg of an off white solid. The crude material was purified by preparative HPLC to give 18 mg of the title compound. MS (ESI) m/e=393.7 [M+H]$^+$.

Example 17

1-[4-Cyclopropyl-3-(cyclopropylmethoxy)benzoyl]-4,4-difluoro-L-prolinamide

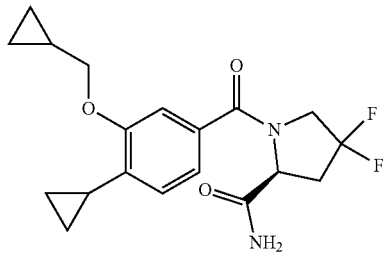 [SMILES: NC(=O)[C@@H]1CC(F)(F)CN1C(=O)c1ccc(C2CC2)c(OCC2CC2)c1]

The title compound was synthesized in analogy to Example 3d, using 4-cyclopropyl-3-(cyclopropylmethoxy)benzoic acid (Example 3c) and (2S)-4,4-difluoroprolinamide (CAN 719267-96-6) as starting materials in the presence of DIEA in THF. The reaction mixture was stirred for 1 day at ambient temperature. The reaction mixture was poured onto ice/water/1N HCl (20 mL) and extracted with EtOAc (2×40 mL). The combined extracts were washed with ice/water (20 mL), dried over Na$_2$SO$_4$ and concentrated in vacuo to give 11 mg of a colorless oil. The crude material was purified by TLC (silica gel, heptane/EtOAc 1:1) and eluted in CH$_2$Cl$_2$/EtOAc 1:1 to give 4 mg of the title compound as colorless oil. MS(ESI): m/e=365.3 [M+H]$^+$.

Example 18

N-(3-Carbamoylpentan-3-yl)-4-cyclopropyl-3-(cyclopropylmethoxy)benzamide

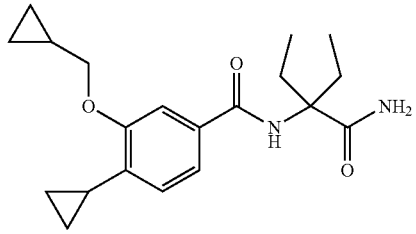 [SMILES: CCC(CC)(NC(=O)c1ccc(C2CC2)c(OCC2CC2)c1)C(N)=O]

The title compound was synthesized in analogy to Example 3d, using 4-cyclopropyl-3-(cyclopropylmethoxy)benzoic acid (Example 3c) and 2-amino-2-ethylbutyramide hydrochloride (CAN 17704-75-5) as starting materials in the presence of DIEA in THF. The reaction mixture was stirred for 2 days at ambient temperature, poured onto ice/water/1N HCl (20 mL) and extracted with EtOAc (2×40 mL). The combined extracts were washed with ice/water (20 mL), dried over Na$_2$SO$_4$ and concentrated in vacuo to give 24 mg of a white solid. The crude material was purified by prep. TLC (silica gel, 1.0 mm heptane/EtOAc 1:1 and eluted in CH$_2$Cl$_2$/EtOAc 1:1 to give 11 mg of the title compound as white solid. MS(ESI): m/e=345.7 [M+H]$^+$.

Example 19

N$^2$-[4-cyclopropyl-3-(cyclopropylmethoxy)benzoyl]-N-methyl-L-leucinamide

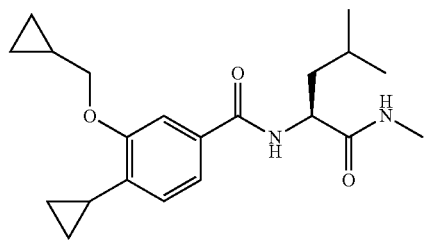 [SMILES: CNC(=O)[C@H](CC(C)C)NC(=O)c1ccc(C2CC2)c(OCC2CC2)c1]

The title compound was synthesized in analogy to Example 3d, using 4-cyclopropyl-3-(cyclopropylmethoxy)benzoic acid (Example 3c) and (S)-2-amino-N,4-dimethylpentanamide hydrochloride (CAN 99145-71-8) as starting materials in the presence of DIEA in THF. The reaction mixture was stirred for 1 day at ambient temperature, poured onto ice/water/1N HCl (20 mL) and extracted with EtOAc (2×40 mL). The combined extracts were washed with ice/water (20 mL), dried over Na$_2$SO$_4$ and concentrated in vacuo. The crude material was purified by HPLC to give 11 mg of the title compound as white solid. MS(ESI): m/e=359.2 [M+H]$^+$.

Example 20

4-Cyclopropyl-3-(cyclopropylmethoxy)-N-[(2S)-1-(methanesulfonyl)-2-(5-methyl-1,2,4-oxadiazol-3-yl)propan-2-yl]benzamide

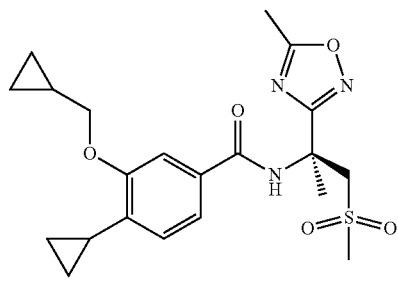 [SMILES: Cc1nc([C@@](C)(CS(C)(=O)=O)NC(=O)c2ccc(C3CC3)c(OCC3CC3)c2)no1]

The title compound was synthesized in analogy to Example 3d, using 4-cyclopropyl-3-(cyclopropylmethoxy)benzoic acid (Example 3c) and (S)-2-(5-methyl-1,2,4-oxadiazol-3-yl)-1-(methylsulfonyl)propan-2-amine (CAN 1613239-21-6) as starting materials in the presence of DIEA in dioxane. The reaction mixture was stirred for 1 d at ambient temperature, poured onto ice/0.1N HCl (25 mL) and extracted with EtOAc (2×25 mL). The combined extracts were washed with icewater/brine (25 mL) to pH 6, dried over Na$_2$SO$_4$ and concentrated under reduced pressure to give 34 mg of an orange liquid. The crude material was purified by preparative TLC (silica gel, 2.0 mm, heptane/AcOEt 1:2) and eluted with EtOAc to give 6 mg of the title compound. MS (ESI) m/e=434.3 [M+H]$^+$.

Example 21

4-Cyclopropyl-3-(cyclopropylmethoxy)-N-[(2R)-1-(methanesulfonyl)-2-(5-methyl-1,2,4-oxadiazol-3-yl)propan-2-yl]benzamide

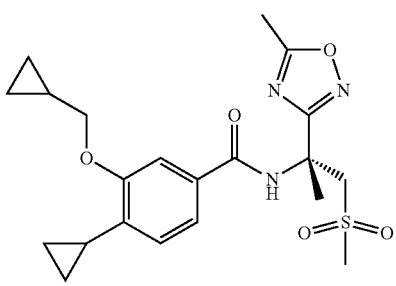 [SMILES: Cc1nc([C@](C)(CS(C)(=O)=O)NC(=O)c2ccc(C3CC3)c(OCC3CC3)c2)no1]

The title compound was synthesized in analogy to Example 3d, using 4-cyclopropyl-3-(cyclopropylmethoxy)benzoic acid (Example 3c) and (R)-2-(5-methyl-1,2,4-oxadiazol-3-yl)-1-(methylsulfonyl)propan-2-amine (CAN 1613239-20-5) as starting materials in the presence of DIEA in dioxane. The reaction mixture was stirred for 1 d at ambient temperature, poured onto ice/0.1N HCl (25 mL) and extracted with EtOAc (2×25 mL). The combined extracts were washed with ice/water/brine (25 mL) to pH 6, dried over Na$_2$SO$_4$ and concentrated under reduced pressure. The crude material was purified by preparative TLC (silica gel, 2.0 mm, heptane/AcOEt 1:2) and eluted with EtOAc to afford 10 mg of the title compound. MS (ESI) m/e=434.3 [M+H]$^+$.

Example 22

5-[4-Cyclopropyl-3-(cyclopropylmethoxy)benzoyl]-5-azaspiro[2.4]heptane-6-carboxamide

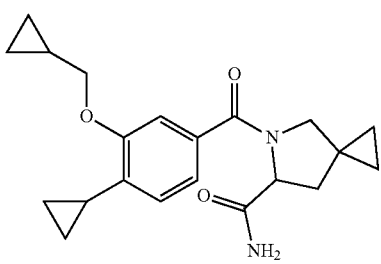 [SMILES: NC(=O)C1CC2(CC2)CN1C(=O)c1ccc(C2CC2)c(OCC2CC2)c1]

The title compound was synthesized in analogy to Example 3d, using 4-cyclopropyl-3-(cyclopropylmethoxy)benzoic acid (Example 3c) and 5-azaspiro[2.4]heptane-6-carboxamide hydrochloride (CAN 1613115-26-6) as starting materials in the presence of DIEA in dioxane. The reaction mixture was stirred for 4 days at ambient temperature, poured onto ice/0.1N HCl (25 mL) and extracted with EtOAc (2×25 mL). The combined extracts were washed with ice/water/brine (25 mL) to pH 6, dried over Na$_2$SO$_4$ and concentrated under reduced pressure. The crude product was purified by prep. HPLC to give 5 mg of the title compound. MS (ESI) m/e=355.3 [M+H]$^+$.

Example 23

5-tert-Butyl-3-[4-cyclopropyl-3-(2,2,2-trifluoroethoxy)phenyl]-1,2,4-oxadiazole

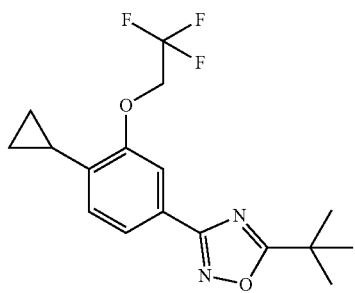 [SMILES: CC(C)(C)c1nc(-c2ccc(C3CC3)c(OCC(F)(F)F)c2)no1]

a) (Z)-4-Bromo-N'-hydroxy-3-methoxybenzimidamide

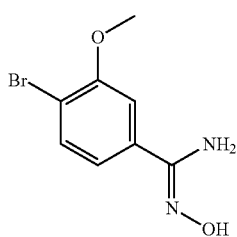

To a solution of 4-bromo-3-methoxybenzonitrile (CAN 120315-65-3; 700 mg, 3.3 mmol) in EtOH (16.5 mL) was added hydroxylamine hydrochloride (344 mg, 4.95 mmol) and triethylamine (920 µL, 6.6 mmol). The reaction mixture was stirred at 60° C. overnight. DCM (60 mL) was added and the mixture was washed with sat. aq. NaHCO$_3$ solution. The aqueous phase was back extracted with ethyl acetate. The combined organic layers were dried on Na$_2$SO$_4$ and evaporated to dryness. The crude product was directly used in the next reaction step without further purification. MS (ESI) m/e=247.1 [M+H]$^+$.

b) 3-(4-Bromo-3-methoxyphenyl)-5-tert-butyl-1,2,4-oxadiazole

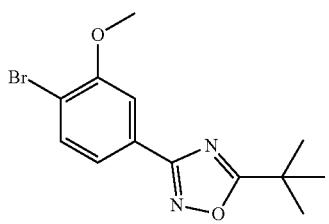 [SMILES: COc1cc(-c2noc(C(C)(C)C)n2)ccc1Br]

To a solution of (Z)-4-bromo-N'-hydroxy-3-methoxybenzimidamide (875 mg, 3.39 mmol) in dry DMF (22.6 mL) was added pivaloyl chloride (543 µL, 4.41 mmol) and triethylamine (946 L, 6.78 mmol). The reaction mixture was stirred at ambient temperature for 30 min. Temperature was increased to 110° C. and stirring was continued overnight. The mixture was concentrated under reduced pressure. Ethyl acetate and aqueous saturated NaHCO₃ solution was added and the layers were separated. The organic layer was dried on Na₂SO₄ and evaporated to dryness. Column chromatography on silica gel using MPLC ISCO with a gradient of heptane/ethyl acetate provided the title compound. MS (ESI) m/e=311.1 [M+H]⁺.

c) 5-tert-Butyl-3-(4-cyclopropyl-3-methoxyphenyl)-1,2,4-oxadiazole

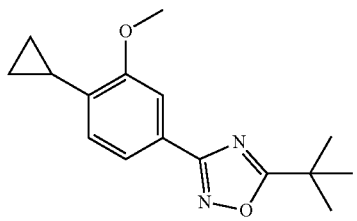 [SMILES: COc1cc(-c2noc(C(C)(C)C)n2)ccc1C1CC1]

To a solution of 3-(4-bromo-3-methoxyphenyl)-5-tert-butyl-1,2,4-oxadiazole (380 mg, 1.22 mmol) in toluene/water (5.4 mL/0.7 mL) was added potassium cyclopropyltrifluoroborate (217 mg, 1.47 mmol), palladium (II) acetate (11 mg, 0.048 mmol), cesium carbonate (995 mg, 3.05 mmol) and butyldi-1-adamantylphosphine (26 mg, 0.073 mmol) under an argon atmosphere. The reaction mixture was stirred at 120° C. overnight. Ethyl acetate and/aqueous saturated NaHCO₃ solution were added. The layers were separated. The organic layer was dried on Na₂SO₄ and evaporated to dryness. The crude product was purified by column chromatography on silica gel using MPLC ISCO with a gradient of heptane/ethyl acetate to provide the title compound. MS (ESI) m/e=273.2 [M+H]⁺.

d) 5-(5-tert-Butyl-1,2,4-oxadiazol-3-yl)-2-cyclopropylphenol

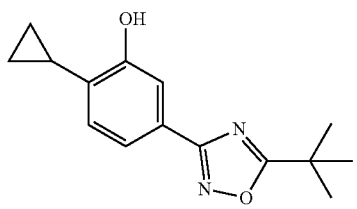 [SMILES: CC(C)(C)c1nc(-c2ccc(C3CC3)c(O)c2)no1]

To a solution of 5-tert-butyl-3-(4-cyclopropyl-3-methoxyphenyl)-1,2,4-oxadiazole (300 mg, 1.1 mmol) in dry CH₂Cl₂ (4.5 mL) under an argon atmosphere was added a 1.0 M solution of BBr₃ in CH₂Cl₂ (1.65 mL, 1.65 mmol). The reaction mixture was stirred at ambient temperature for 12 h, quenched by addition of water and stirred for 10 min. Aqueous saturated NH₄Cl solution was added and the layers were separated. The aqueous phase was back-extracted with CH₂Cl₂. The organic phases were combined, dried over MgSO₄ and evaporated to dryness to give 255 mg of the title compound. MS (ESI) m/e=259.2 [M+H]⁺.

e) 5-tert-Butyl-3-[4-cyclopropyl-3-(2,2,2-trifluoroethoxy)phenyl]-1,2,4-oxadiazole To a solution of 5-(5-tert-butyl-1,2,4-oxadiazol-3-yl)-2-cyclopropylphenol (44 mg, 0.17 mmol) in dry DMF (1.1 mL) was added cesium carbonate (166 mg, 0.511 mmol) and 2,2,2-trifluoroethyl trifluoromethanesulfonate (CAN 6226-25-1; 35 µL, 0.256 mmol). The mixture was stirred for 4 h at ambient temperature. The solvent was partially removed under reduced pressure. Water and ethyl acetate were added, the layers were separated and the organic layer was dried over MgSO₄. Evaporation of the solvent was followed by column chromatography on silica with a gradient of heptane/ethyl acetate to give the title compound as colorless viscous oil. MS (ESI) m/e=341.2 [M+H]⁺.

Example 24

5-tert-Butyl-3-[4-cyclopropyl-3-(2,2-difluoroethoxy)phenyl]-1,2,4-oxadiazole

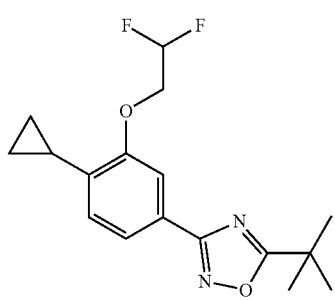 [SMILES: CC(C)(C)c1nc(-c2ccc(C3CC3)c(OCC(F)F)c2)no1]

The title compound was synthesized in analogy to Example 23e, using 5-(5-tert-butyl-1,2,4-oxadiazol-3-yl)-2-cyclopropylphenol (Example 23d) and 2,2-difluoroethyl trifluoromethanesulfonate (CAN 74427-22-8) as starting materials to give a colorless viscous oil. MS (ESI) m/e=323.3 [M+H]⁺.

Example 25

(−)-4-Cyclopropyl-N-[1-cyclopropyl-2-(5-methyl-1,2,4-oxadiazol-3-yl)propan-2-yl]-3-(2,2,2-trifluoroethoxy)benzamide

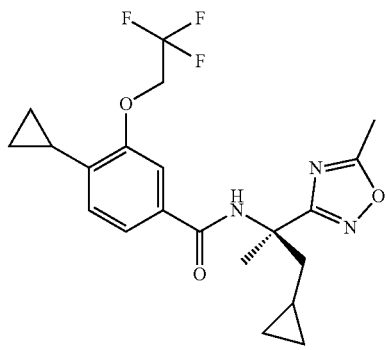 [SMILES: Cc1nc([C@@](C)(CC2CC2)NC(=O)c2ccc(C3CC3)c(OCC(F)(F)F)c2)no1]

a) Ethyl 4-bromo-3-(2,2,2-trifluoroethoxy)benzoate

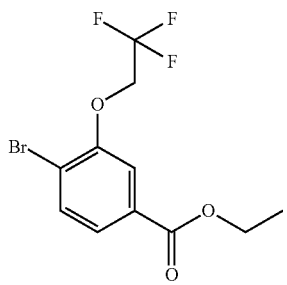 [SMILES: CCOC(=O)c1ccc(Br)c(OCC(F)(F)F)c1]

To a solution of ethyl 4-bromo-3-hydroxybenzoate (CAN 33141-66-1; 2.09 g, 8.53 mmol) in DMF (57 mL) cesium carbonate (8.34 g, 25.6 mmol) and 2,2,2-trifluoroethyl trifluoromethanesulfonate (CAN 6226-25-1; 1.28 mL, 9.38 mmol) were added. The reaction was stirred for 8 h at ambient temperature. The solvent was removed under reduced pressure. The residue was dissolved in DCM and washed with aqueous saturated NaHCO$_3$ solution. The layers were separated, the organic layer was dried over MgSO$_4$ and brought to dryness. The crude product was purified by column chromatography on silica gel using a gradient of heptane/ethyl acetate to give 2.7 g of the title compound. MS m/e=326 [M]$^+$.

b) Ethyl 4-cyclopropyl-3-(2,2,2-trifluoroethoxy)benzoate

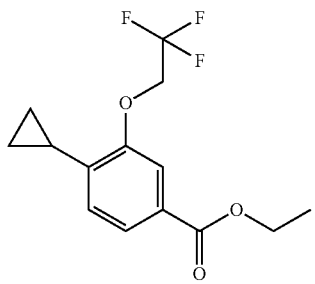 [SMILES: CCOC(=O)c1ccc(C2CC2)c(OCC(F)(F)F)c1]

To a solution of ethyl 4-bromo-3-(2,2,2-trifluoroethoxy)benzoate (2.46 g, 7.52 mmol) in toluene/water (33 mL/4.4 mL) was added potassium cyclopropyltrifluoroborate (1.34 g, 9.02 mmol), palladium (II) acetate (67.5 mg, 0.301 mmol), cesium carbonate (6.13 g, 18.8 mmol) and butyldi-1-adamantylphosphine (162 mg, 0.451 mmol) under an argon atmosphere. The mixture was stirred at 120° C. for 12 h. Ethyl acetate and sat. aq. NaHCO$_3$ solution were added. The layers were separated. The organic layer was dried on Na$_2$SO$_4$ and evaporated. The residue was purified by column chromatography on silica gel with heptane/ethyl acetate to afford the title compound. MS (ESI) m/e=289.2 [M+H]$^+$.

c) 4-Cyclopropyl-3-(2,2,2-trifluoroethoxy)benzoic acid

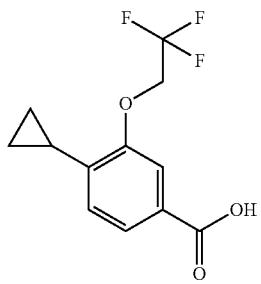 [SMILES: O=C(O)c1ccc(C2CC2)c(OCC(F)(F)F)c1]

To a solution of ethyl 4-cyclopropyl-3-(2,2,2-trifluoroethoxy)benzoate (1.635 g, 5.67 mmol) in dioxane/water 1/1 (38 mL) was added LiOH×H$_2$O (476 mg, 11.3 mmol). The mixture was stirred at ambient temperature for 12 h. 1M aqueous HCl solution and ethyl acetate/ethanol (3/1) were added. The layers were separated. The organic layer was dried on MgSO$_4$ and evaporated. The residue was purified by column chromatography on silica gel using MPLC ISCO with a gradient of heptane/ethyl acetate to give the title compound. MS (ESI) m/e=259.1 [M−H]$^-$.

d) (−)-4-Cyclopropyl-N-[1-cyclopropyl-2-(5-methyl-1,2,4-oxadiazol-3-yl)propan-2-yl]-3-(2,2,2-trifluoroethoxy)benzamide To a solution of 4-cyclopropyl-3-(2,2,2-trifluoroethoxy) benzoic acid (100 mg, 0.384 mmol) in DMF (2.5 mL) was added DIEA (134 µL, 0.769 mmol) and TBTU (148 mg, 0.461 mmol). The mixture was stirred for 5 min at ambient temperature. 1,2,4-Oxadiazole-3-methanamine, α-(cyclopropylmethyl)-α,5-dimethyl-, hydrochloride (CAN 1415900-39-8; 92 mg, 0.423 mmol was added and stirring was continued for 3 h. The solvent was removed under reduced pressure. The residue was dissolved in ethyl acetate and washed with saturated aqeuous NaHCO$_3$ solution. The layers were separated. The organic layer was dried on Na$_2$SO$_4$ and evaporated to dryness. The residue was purified by column chromatography on silica gel with a gradient of heptane/ethyl acetate. The enantiomers were separated by chiral prep. HPLC to give the title compound. MS (ESI) m/e=424.3 [M+H]$^+$.

Example 26

(+)-4-Cyclopropyl-N-[1-cyclopropyl-2-(5-methyl-1,2,4-oxadiazol-3-yl)propan-2-yl]-3-(2,2,2-trifluoroethoxy)benzamide

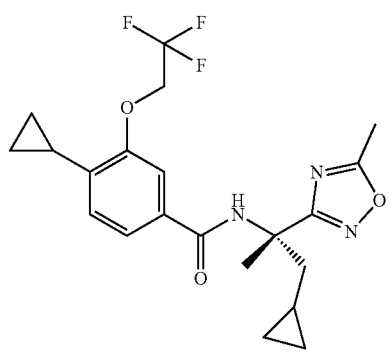 [SMILES: Cc1nc([C@](C)(CC2CC2)NC(=O)c2ccc(C3CC3)c(OCC(F)(F)F)c2)no1]

The title compound was synthesized in analogy to Example 25d, using 4-cyclopropyl-3-(2,2,2-trifluoroethoxy) benzoic acid (Example 25c) and 1,2,4-oxadiazole-3-methanamine, α-(cyclopropylmethyl)-α,5-dimethyl-, hydrochloride (CAN 1415900-39-8) as starting materials. The enantiomers were separated by chiral prep. HPLC to give the title compound. MS (ESI) m/e=424.3 [M+H]$^+$.

Example 27

N-[3-(2-Amino-2-oxoethyl)-1,1-dioxothietan-3-yl]-4-cyclopropyl-3-(2,2,2-trifluoroethoxy)benzamide

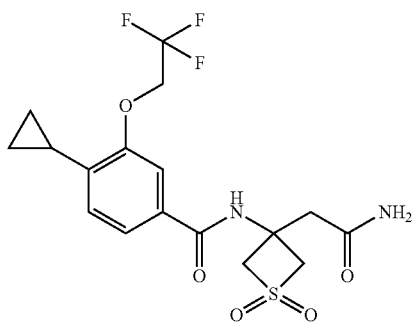 [SMILES: NC(=O)CC1(NC(=O)c2ccc(C3CC3)c(OCC(F)(F)F)c2)CS(=O)(=O)C1]

The title compound was synthesized in analogy to Example 25d, using 4-cyclopropyl-3-(2,2,2-trifluoroethoxy)benzoic acid (Example 25c) and 2-(3-amino-1,1-dioxo-thietan-3-yl)acetamide (CAN 1613239-56-7) as starting materials. The crude product was purified by flash chromatography on silica gel using a gradient of heptane/ethyl acetate to afford the title compound. MS (ESI) m/e=421.2 [M+H]$^+$.

Example 28

4-Cyclopropyl-N-[(2R)-1-(methanesulfonyl)-2-(5-methyl-1,2,4-oxadiazol-3-yl)propan-2-yl]-3-(2,2,2-trifluoroethoxy)benzamide

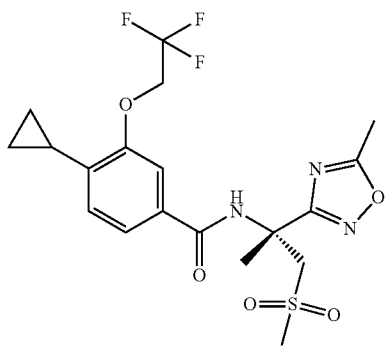 [SMILES: Cc1nc([C@](C)(CS(C)(=O)=O)NC(=O)c2ccc(C3CC3)c(OCC(F)(F)F)c2)no1]

The title compound was synthesized in analogy to Example 25d, using 4-cyclopropyl-3-(2,2,2-trifluoroethoxy)benzoic acid (Example 25c) and (R)-2-(5-methyl-1,2,4-oxadiazol-3-yl)-1-(methylsulfonyl)propan-2-amine (CAN 1613239-20-5) as starting materials. The crude product was purified by flash chromatography on silica gel using a gradient of heptane/ethyl acetate to afford the title compound. MS (ESI) m/e=462.2 [M+H]$^+$.

Example 29

4-Cyclopropyl-N-[(2S)-1-(methanesulfonyl)-2-(5-methyl-1,2,4-oxadiazol-3-yl)propan-2-yl]-3-(2,2,2-trifluoroethoxy)benzamide

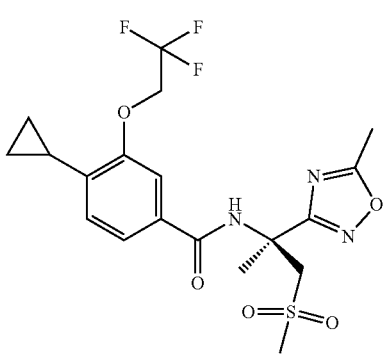 [SMILES: Cc1nc([C@@](C)(CS(C)(=O)=O)NC(=O)c2ccc(C3CC3)c(OCC(F)(F)F)c2)no1]

The title compound was synthesized in analogy to Example 25d, using 4-cyclopropyl-3-(2,2,2-trifluoroethoxy)benzoic acid (Example 25c) and (S)-2-(5-methyl-1,2,4-oxadiazol-3-yl)-1-(methylsulfonyl)propan-2-amine (CAN 1613239-21-6) as starting materials. The crude product was purified by flash chromatography on silica gel using a gradient of heptane/ethyl acetate to afford the title compound. MS (ESI) m/e=462.2 [M+H]$^+$.

Example 30

5-tert-Butyl-3-[4-cyclopropyl-3-(2-fluoroethoxy)phenyl]-1,2,4-oxadiazole

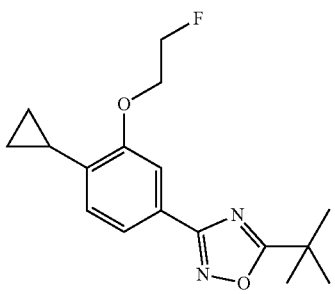 [SMILES: CC(C)(C)c1nc(-c2ccc(C3CC3)c(OCCF)c2)no1]

The title compound was synthesized in analogy to Example 23e, using 5-(5-tert-butyl-1,2,4-oxadiazol-3-yl)-2-cyclopropylphenol (Example 23d) and 1-fluoro-2-iodoethane (CAN 762-51-6) as starting materials. MS (ESI) m/e=305.2 [M+H]$^+$.

Example 31

(−)-4-Cyclopropyl-N-[1-cyclopropyl-2-(5-methyl-1,2,4-oxadiazol-3-yl)propan-2-yl]-3-(2,2-difluoroethoxy)benzamide

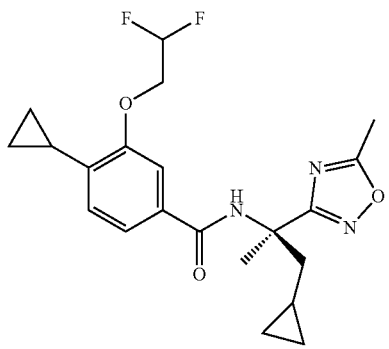 [SMILES: Cc1nc([C@@](C)(CC2CC2)NC(=O)c2ccc(C3CC3)c(OCC(F)F)c2)no1]

The title compound was synthesized in analogy to Example 25d, using 4-cyclopropyl-3-(2,2-difluoroethoxy)benzoic acid, previously prepared in analogy to Example 25 using ethyl 4-bromo-3-hydroxybenzoate (CAN 33141-66-1) and 2,2-difluoroethyl trifluoromethanesulfonate (CAN 74427-22-8) in step a, and 1,2,4-oxadiazole-3-methanamine, α-(cyclopropylmethyl)-α,5-dimethyl-, hydrochloride (CAN 1415900-39-8) as starting materials. The crude product was purified by flash chromatography on silica gel using a gradient of heptane/ethyl acetate to afford a mixture of enantiomers. Separation of the enantiomers by chiral prep. HPLC provided the title compound. MS (ESI) m/e=406.2 [M+H]$^+$.

Example 32

(+)-4-Cyclopropyl-N-[1-cyclopropyl-2-(5-methyl-1,2,4-oxadiazol-3-yl)propan-2-yl]-3-(2,2-difluoroethoxy)benzamide

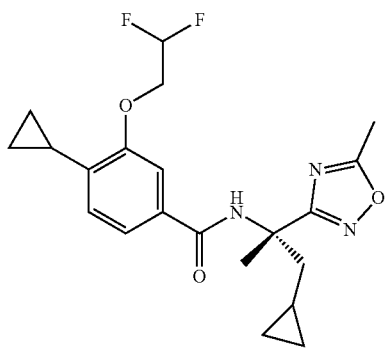 [SMILES: Cc1nc([C@](C)(CC2CC2)NC(=O)c2ccc(C3CC3)c(OCC(F)F)c2)no1]

The title compound was synthesized in analogy to Example 31, using 4-cyclopropyl-3-(2,2-difluoroethoxy)benzoic acid and 1,2,4-oxadiazole-3-methanamine,α-(cyclopropylmethyl)-α,5-dimethyl-, hydrochloride (CAN 1415900-39-8) as starting materials. The crude product was purified by flash chromatography on silica gel using a gradient of heptane/ethyl acetate to afford a mixture of enantiomers. Separation of the enantiomers by chiral prep. HPLC provided the title compound. MS (ESI) m/e=406.2 [M+H]$^+$.

Example 33

(−)-4-Cyclopropyl-N-[(1-cyclopropyl-2-(5-methyl-1,2,4-oxadiazol-3-yl)propan-2-yl]-3-(2-fluoroethoxy)benzamide

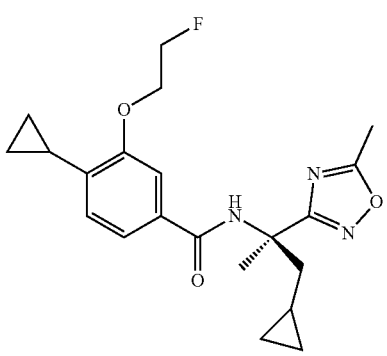 [SMILES: Cc1nc([C@@](C)(CC2CC2)NC(=O)c2ccc(C3CC3)c(OCCF)c2)no1]

The title compound was synthesized in analogy to Example 25d, using 4-cyclopropyl-3-(2-fluoroethoxy)benzoic acid, previously prepared in analogy to Example 25 using ethyl 4-bromo-3-hydroxybenzoate (CAN 33141-66-1) and 1-fluoro-2-iodoethane (CAN 762-51-6) in step a, and 1,2,4-oxadiazole-3-methanamine,α-(cyclopropylmethyl)-α,5-dimethyl-, hydrochloride (CAN 1415900-39-8) as starting materials. The crude product was purified by flash chromatography on silica gel using a gradient of heptane/ethyl acetate to afford a mixture of enantiomers. Separation of the enantiomers by chiral prep. HPLC provided the title compound. MS (ESI) m/e=388.2 [M+H]$^+$.

Example 34

(+)-4-Cyclopropyl-N-[1-cyclopropyl-2-(5-methyl-1,2,4-oxadiazol-3-yl)propan-2-yl]-3-(2-fluoroethoxy)benzamide

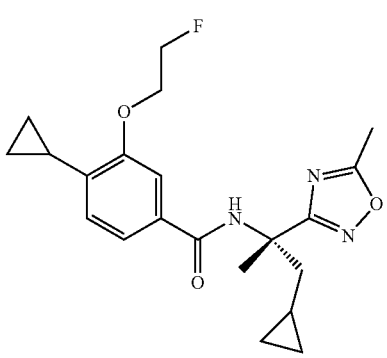 [SMILES: Cc1nc([C@](C)(CC2CC2)NC(=O)c2ccc(C3CC3)c(OCCF)c2)no1]

The title compound was synthesized in analogy to Example 33, using 4-cyclopropyl-3-(2-fluoroethoxy)benzoic acid and 1,2,4-oxadiazole-3-methanamine,α-(cyclopropylmethyl)-α,5-dimethyl-, hydrochloride (CAN 1415900-39-8) as starting materials. The crude product was purified by flash chromatography on silica gel using a gradient of heptane/ethyl acetate to afford a mixture of enantiomers. Separation of the enantiomers by chiral prep. HPLC provided the title compound. MS (ESI) m/e=388.2 [M+H]$^+$.

Example 35

(−)-N-[4-Amino-2-cyclopropyl-4-oxobutan-2-yl]-4-cyclopropyl-3-(2,2,2-trifluoroethoxy)benzamide

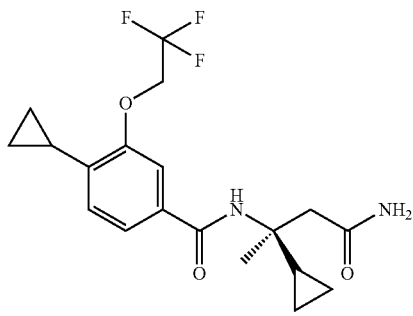 [SMILES: C[C@@](CC(N)=O)(NC(=O)c1ccc(C2CC2)c(OCC(F)(F)F)c1)C1CC1]

The title compound was synthesized in analogy to Example 25d, using 4-cyclopropyl-3-(2,2,2-trifluoroethoxy)benzoic acid (Example 25c) and 3-amino-3-cyclopropyl-butanamide (CAN 1534510-01-4) as starting materials. The crude product was purified by flash chromatography on silica gel using a gradient of heptane/ethyl acetate to afford a mixture of enantiomers. Separation of the enantiomers by chiral prep. HPLC provided the title compound. MS (ESI) m/e=385.2 [M+H]$^+$.

Example 36

(+)-N-[4-amino-2-cyclopropyl-4-oxobutan-2-yl]-4-cyclopropyl-3-(2,2,2-trifluoroethoxy)benzamide

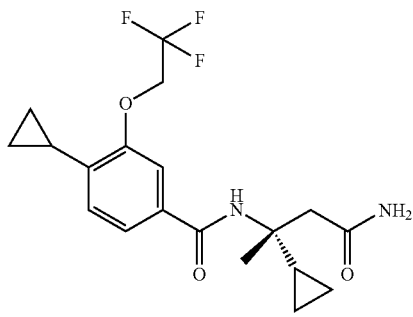 [SMILES: C[C@](CC(N)=O)(NC(=O)c1ccc(C2CC2)c(OCC(F)(F)F)c1)C1CC1]

The title compound was synthesized in analogy to Example 25d, using 4-cyclopropyl-3-(2,2,2-trifluoroethoxy)benzoic acid (Example 25c) and 3-amino-3-cyclopropyl-butanamide (CAN 1534510-01-4) as starting materials. The crude product was purified by flash chromatography on silica gel using a gradient of heptane/ethyl acetate to afford a mixture of enantiomers. Separation of the enantiomers by chiral prep. HPLC provided the title compound. MS (ESI) m/e=385.2 [M+H]$^+$.

Example 37

4-Cyclopropyl-N-[(2S)-3,3-dimethyl-1-(methylamino)-1-oxobutan-2-yl]-3-[(propan-2-yl)oxy]benzamide

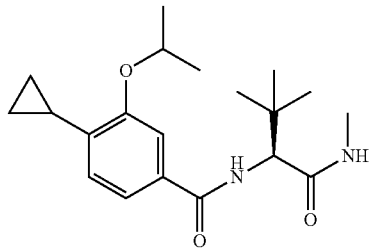 [SMILES: CNC(=O)[C@@H](NC(=O)c1ccc(C2CC2)c(OC(C)C)c1)C(C)(C)C]

a) Methyl 4-bromo-3-(propan-2-yloxy)benzoate

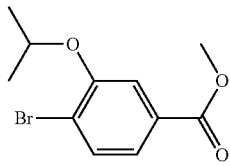

To a stirred solution of methyl 4-bromo-3-hydroxybenzoate (CAN 106291-80-9; 4 g, 17.3 mmol) in THF (100 mL), propane-2-ol (2 mL, 25.96 mmol), triphenylphosphine (6.83 g, 25.96 mmol) and diisopropyl azodicarboxylate (DIAD; 5.14 mL, 25.96 mmol) were added at 25° C. The reaction mixture was stirred at 25° C. for 15 h. The reaction volatiles were removed under reduced pressure to get crude product which was purified by column chromatography using 10% ethyl acetate in hexane as eluents to obtain the title compound (4 g, 85%) as light red liquid.

b) Methyl 4-cyclopropyl-3-(propan-2-yloxy)benzoate

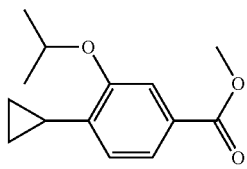 [SMILES: COC(=O)c1ccc(C2CC2)c(OC(C)C)c1]

Methyl 4-bromo-3-(propan-2-yloxy)benzoate (3 g, 10.98 mmol), cyclopropylboronic acid (1.2 g, 14.27 mmol) and K$_3$PO$_4$ (5.83 g, 27.45 mmol) were dissolved in tolene-water (60 mL/2.5 mL) and the mixture was degassed with nitrogen for 30 min. Palladium(II)acetate (250 mg, 1.09 mmol) and tricyclohexylphosphine (308 mg, 1.09 mmol) were added. The mixture was degassed with argon for 20 min and then heated to 100° C. for 15 h. The reaction mixture was diluted with water (50 mL) and extracted with ethyl acetate (3×100 mL). The combined organic layers were washed with brine and dried over anhydrous Na$_2$SO$_4$. The solvent was removed under reduced pressure to get crude product which was purified by combiflash column chromatography using 15% ethyl acetate in hexane as eluents to get the title compound (2 g, 78%) as light yellow liquid.

c) 4-Cyclopropyl-3-(propan-2-yloxy)benzoic acid

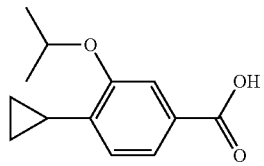 [SMILES: CC(C)Oc1cc(C(=O)O)ccc1C1CC1]

To a stirred solution of methyl 4-bromo-3-(propan-2-yloxy)benzoate (2.1 g, 8.97 mmol) in dioxane/water 1/1 (60 mL) was added LiOH×H$_2$O (753 mg, 17.94 mmol) at 25° C. The reaction mixture was stirred at 25° C. for 15 h and then brought to pH 2-3 by adding 1M aq. HCl solution. Extraction with ethyl acetate (3×50 mL) was followed by washing the combined organic layers with brine and drying over Na$_2$SO$_4$. Removal of the solvent under reduced pressure provided crude product which was purified by combiflash column chromatography using 40% ethyl acetate in hexane as eluents to get the title compound (1.4 g, 71%) as off white solid. MS (ESI) m/e=219.0 [M−H]$^-$.

d) 4-Cyclopropyl-N-[(2S)-3,3-dimethyl-1-(methylamino)-1-oxobutan-2-yl]-3-[(propan-2-yl)oxy]benzamide To a stirred solution of 4-cyclopropyl-3-(propan-2-yloxy) benzoic acid (100 mg, 0.45 mmol) in DMF (2.5 mL) were added DIEA (0.3 mL, 1.81 mmol) and 2-chloro-1-methylpyridinium iodide (290 mg, 1.13 mmol). The mixture was stirred for 1.5 h at 25° C. (2S)-2-Amino-N,3,3-trimethylbutanamide (CAN 89226-12-0; 78.7 mg, 0.55 mmol) was added and stirring was continued at 25° C. for 16 h. The reaction mixture was diluted with water (20 mL) and extracted with ethyl acetate (2×50 mL). The combined organic layers were washed with brine (50 mL), dried over anhydrous Na$_2$SO$_4$ and concentrated in vacuo to get the crude product which was purified via prep. HPLC to obtain the title compound (13.5 mg, 9%) as off white solid. MS (ESI) m/e=347.1 [M+H]$^+$.

Example 38

4-Cyclopropyl-N-[(2S)-1-cyclopropyl-2-(5-methyl-1,2,4-oxadiazol-3-yl)propan-2-yl]-3-[(propan-2-yl)oxy]benzamide or enantiomer

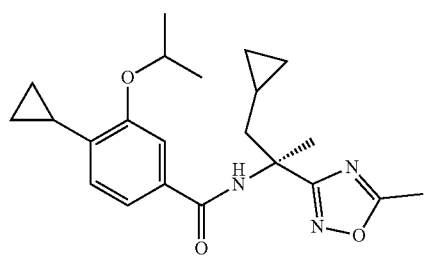 [SMILES: Cc1nc([C@](C)(CC2CC2)NC(=O)c2ccc(C3CC3)c(OC(C)C)c2)no1]

a) 2-Cyclopropyl-N-methoxy-N-methylacetamide

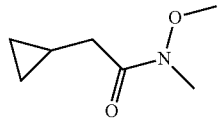

To a stirred solution of cyclopropyl-acetic acid (40 g, 400 mmol) in DCM (400 mL) was added CDI (70 g 431.6 mmol) portion wise and the reaction mixture was stirred for 2 h at 25° C. O,N-dimethyl-hydroxylamine hydrochloride (39.76 g, 407.6 mmol) was added in one portion. The reaction mixture was stirred for 12 h at 25° C., poured in to ice-cold water (300 mL) and extracted with DCM (2×200 mL). The combined DCM layer was washed with brine (200 mL), dried over anhydrous Na$_2$SO$_4$ and concentrated under reduced pressure. The crude product was purified by combiflash column chromatography to get the title compound (45 g, 79%) as colorless liquid.

b) 1-Cyclopropylpropan-2-one

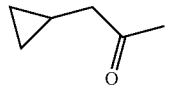

To a stirred solution of 2-cyclopropyl-N-methoxy-N-methylacetamide (25 g, 174.9 mmol) in dry diethyl ether (125 mL) was added methyl lithium (1.6 M solution in ether; 120 mL, 192.3 mmol) at −15° C. over 30 min. The reaction mixture was stirred for 1.5 h at 0° C., quenched with saturated aqueous NH$_4$Cl solution (100 mL) and extracted with diethyl ether (2×300 mL). The combined ether layer was washed with brine solution (200 mL). dried over anhydrous Na$_2$SO$_4$ and concentrated under reduced pressure to give crude title compound (52 g) as light yellow liquid that was used in the next step without further purification.

c) 2-Amino-3-cyclopropyl-2-methylpropanenitrile

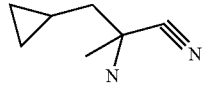

To a stirred solution of 1-cyclopropylpropan-2-one (36 g, 367 mmol) in ethanol (360 mL) was added NH$_4$OH (25% in water; 360 mL) at 25° C. and ammonium chloride (20 g, 374 mmol). The reaction mixture was stirred at 25° C. for 1 h. Potassium cyanide (37 g, 572 mmol) was added portion wise and stirring was continued for 12 h. The mixture was concentrated under reduced pressure, diluted with water (500 mL) and extracted with ethyl acetate (3×200 mL). The combined organic layer was washed with saturated ferrous sulphate solution (3×300 mL) and brine (200 mL), dried over anhydrous Na$_2$SO$_4$ and concentrated under reduced pressure to obtain crude title compound (25 g) as light yellow oil which was used for next step without further purification. MS m/e=123 [M−H]$^-$.

d) Benzyl N-(1-cyano-2-cyclopropyl-1-methylethyl)carbamate

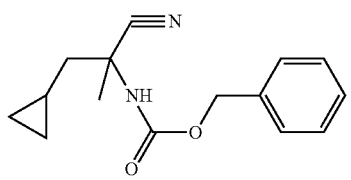 [SMILES: CC(C#N)(CC1CC1)NC(=O)OCc1ccccc1]

To a stirred solution of 2-amino-3-cyclopropyl-2-methyl-propanenitrile (24 g, 194 mmol) in dry THF (570 mL) was added DIEA (70 mL, 426 mmol) and benzyl carbonochloridate (50% in toluene; 79.2 mL, 232 mmol) at 25° C. The mixture was stirred at 45° C. for 18 h and concentrated under reduced pressure. The residue was dissolved in ethyl acetate (300 mL) and washed with 1 M aqueous NaHCO$_3$ solution (250 mL). The layers were separated. The aqueous layer was extracted with ethyl acetate (2×200 mL). The combined organic layer was washed with brine (200 mL), dried over anhydrous Na$_2$SO$_4$ and evaporated to dryness. The crude product was purified by combiflash column chromatography eluting with 10% ethyl acetate in hexane to obtain the title compound (42 g, 44%) as colorless oil. MS m/e=258.9 [M]$^+$.

e) Benzyl N-[2-cyclopropyl-1-(N-hydroxycarbamimidoyl)-1-methylethyl]carbamate

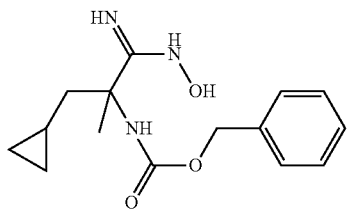 [SMILES: CC(CC1CC1)(NC(=O)OCc1ccccc1)C(=N)NO]

To a stirred solution of benzyl N-(1-cyano-2-cyclopropyl-1-methylethyl)carbamate (42 g, 162.8 mmol) in ethanol (520 mL) were added triethylamine (25 mL, 179.1 mmol) and hydroxylamine hydrochloride (11.3 g, 162.5 mmol). The reaction mixture was stirred at 60° C. for 18 h. The volatiles were removed under reduced pressure. The residue was diluted with ethyl acetate (300 mL) and aqueous NaHCO$_3$ solution (200 mL). The layers were separated. The aqueous layer was extracted with ethyl acetate (2×200 mL). The combined organic layer was dried over anhydrous Na$_2$SO$_4$ and evaporated to dryness. The crude product was purified by CombiFlash column chromatography eluting with 15-20% ethyl acetate in hexane to obtain the title compound (40 g, 84%) as white solid. MS (ESI) m/e=292.2 [M+H]$^+$.

f) Benzyl N-[(2S)-1-cyclopropyl-2-(5-methyl-1,2,4-oxadiazol-3-yl)propan-2-yl]carbamate

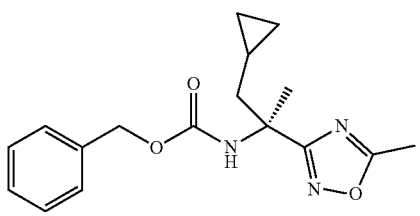 [SMILES: Cc1nc([C@](C)(CC2CC2)NC(=O)OCc2ccccc2)no1]

To a stirred solution of benzyl N-[2-cyclopropyl-1-(N-hydroxycarbamimidoyl)-1-methylethyl]carbamate (26 g, 89.3 mmol) in isopropyl alcohol (466 mL) was added 1,1 dimethoxy-N,N-dimethylethanamine (47.6 g, 357.4 mmol). The reaction mixture was stirred for 17 h at 25° C. After cooling to 0° C. 4 M hydrochloric acid in dioxane (112 mL, 447 mmol) was added drop wise. Stirring was continued for 2 h at 0° C. Ethyl acetate (300 mL) was added and the mixture was washed with aqueous 2M sodium carbonate solution (500 mL). The aqueous layer was extracted with ethyl acetate (2×300 mL). The combined organic layer was washed with brine (200 mL), dried over anhydrous Na$_2$SO$_4$ and evaporated to dryness. The crude product was purified by combiflash column chromatography eluting with 20-30% ethyl acetate in hexane to obtain racemic benzyl N-[1-cyclopropyl-2-(5-methyl-1,2,4-oxadiazol-3-yl)propan-2-yl] carbamate (25 g, 85%) as colorless sticky oil. Chiral separation provided the title compound (11.5 g, 46%) as colorless sticky oil. MS (ESI) m/e=315.9 [M+H]$^+$.

g) (2S)-1-Cyclopropyl-2-(5-methyl-1,2,4-oxadiazol-3-yl)propan-2-amine

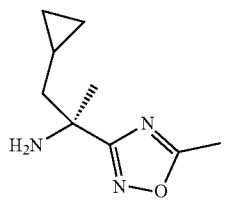

To a stirred solution of benzyl N-[(2S)-1-cyclopropyl-2-(5-methyl-1,2,4-oxadiazol-3-yl)propan-2-yl]carbamate (11.5 g, 36.5 mmol) in dry DCM (250 mL) was added BCl3 (1 M solution in DCM; 186 mL) at 0° C. under a nitrogen atmosphere. The reaction mixture was stirred at 25° C. for 1.5 h. The solution was quenched with methanol (30 mL) and H$_2$O (10 mL). The solvent was removed under reduced pressure. The residue was taken up in water (100 mL), basified with saturated sodium bicarbonate solution and extracted with DCM (2×200 mL). The combined extracts were washed with brine (100 mL), dried over anhydrous Na$_2$SO$_4$ and evaporated to dryness to give the title compound (5.4 g, 82%) as light brown liquid.

h) (2S)-1-Cyclopropyl-2-(5-methyl-1,2,4-oxadiazol-3-yl)propan-2-amine hydrochloride

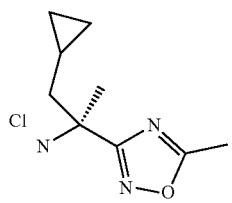

To a stirred solution of (2S)-1-cyclopropyl-2-(5-methyl-1,2,4-oxadiazol-3-yl)propan-2-amine (5.4 g, 29.8 mmol) in methanol (50 mL) was added a 4 M solution of hydrochloric acid in dioxane (37 mL, 149 mmol) drop wise at 0° C. The solution was stirred for 2 h at 25° C. The volatiles were i) 4-Cyclopropyl-N-[(2S)-1-cyclopropyl-2-(5-methyl-1,2,4-oxadiazol-3-yl)propan-2-yl]-3-[(propan-2-yl)oxy]benzamide or enantiomer The title compound was synthesized in analogy to Example 37d from 4-cyclopropyl-3-(propan-2-yloxy)benzoic acid (Example 37c; 110 mg, 0.5 mmol) and (2S)-1-Cyclopropyl-2-(5-methyl-1,2,4-oxadiazol-3-yl)propan-2-amine hydrochloride (109 mg, 0.5 mmol) as off white solid (46 mg, 24%). MS (ESI) m/e=384.1 [M+H]+.

Example 39

4-Cyclopropyl-N-[(2S)-3,3-dimethyl-1-(methylamino)-1-oxobutan-2-yl]-3-(2-fluoroethoxy)benzamide

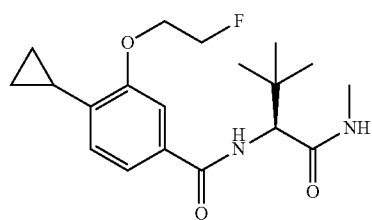 [SMILES: CNC(=O)[C@@H](NC(=O)c1ccc(C2CC2)c(OCCF)c1)C(C)(C)C]

The title compound was synthesized in analogy to Example 37d from 4-cyclopropyl-3-(2-fluoroethoxy)benzoic acid (Example 33; 100 mg, 0.45 mmol) and (2S)-2-amino-N,3,3-trimethylbutanamide (CAN 89226-12-0; 66.5 mg, 0.46 mmol) as off white solid (110 mg, 70%). MS (ESI) m/e=350.9 [M+H]+.

Example 40

1-[4-Cyclopropyl-3-(2-fluoroethoxy)benzoyl]-4,4-difluoro-L-prolinamide

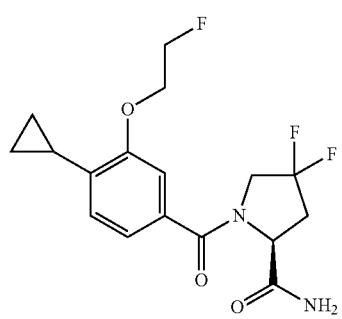 [SMILES: NC(=O)[C@@H]1CC(F)(F)CN1C(=O)c1ccc(C2CC2)c(OCCF)c1]

The title compound was synthesized in analogy to Example 37d from 4-cyclopropyl-3-(2-fluoroethoxy)benzoic acid (Example 33; 100 mg, 0.45 mmol) and (2S)-4,4-difluoropyrrolidine-2-carboxamide hydrochloride (CAN 426844-51-1; 86 mg, 0.46 mmol) as off white solid (63 mg, 46%). MS (ESI) m/e=356.9 [M+H]+.

Example 41

4-Cyclopropyl-N-[(2S)-3,3-dimethyl-1-(methylamino)-1-oxobutan-2-yl]-3-(2,2,2-trifluoroethoxy)benzamide

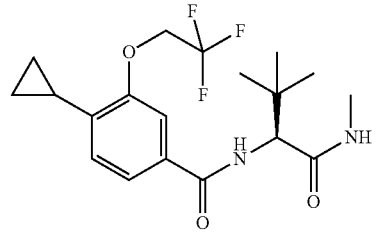 [SMILES: CNC(=O)[C@@H](NC(=O)c1ccc(C2CC2)c(OCC(F)(F)F)c1)C(C)(C)C]

The title compound was synthesized in analogy to Example 37d from 4-cyclopropyl-3-(2,2,2-trifluoroethoxy)benzoic acid (Example 25c; 100 mg, 0.38 mmol) and (2S)-2-amino-N,3,3-trimethylbutanamide (CAN 89226-12-0; 67 g, 0.46 mmol) as off white solid (49 mg, 70%). MS (ESI) m/e=386.8 [M+H]+.

Example 42

1-[4-Cyclopropyl-3-(2,2,2-trifluoroethoxy)benzoyl]-4,4-difluoro-L-prolinamide

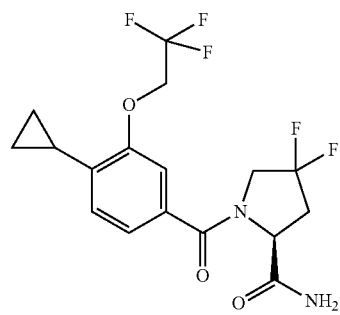 [SMILES: NC(=O)[C@@H]1CC(F)(F)CN1C(=O)c1ccc(C2CC2)c(OCC(F)(F)F)c1]

The title compound was synthesized in analogy to Example 37d from 4-cyclopropyl-3-(2,2,2-trifluoroethoxy)benzoic acid (Example 25c; 100 mg, 0.38 mmol) and (2S)-4,4-difluoropyrrolidine-2-carboxamide hydrochloride (CAN 426844-51-1; 86.1 mg, 0.46 mmol) as off white solid (55 mg, 37%). MS (ESI) m/e=393.1 [M+H]+.

Example 43

N-[(2S)-4-Amino-2-cyclopropyl-4-oxobutan-2-yl]-4-cyclopropyl-3-[(propan-2-yl)oxy]benzamide

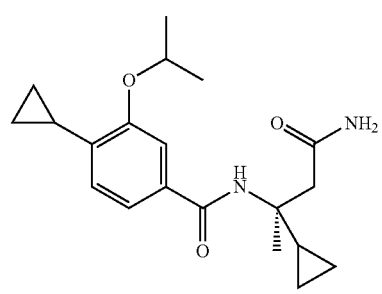 [SMILES: CC(C)Oc1cc(C(=O)N[C@@](C)(CC(N)=O)C2CC2)ccc1C1CC1]

The title compound was synthesized in analogy to Example 37d from 4-cyclopropyl-3-(propan-2-yloxy)benzoic acid (Example 37c; 100 mg, 0.45 mmol) and (3S)-3-amino-3-cyclopropylbutanamide hydrochloride (97 mg, 0.54 mmol) as off white solid (56 mg, 36%). (3S)-3-Amino-3-cyclopropylbutanamide hydrochloride was prepared in analogy to 3-cyclopropyl-3-[(2-methylpropane-2-sulfinyl)amino]butanoic acid (CAN 1534510-01-4) starting from (R)-2-methylpropane-2-sulfinamide (CAN 196929-78-9) and 1-cyclopropyl-ethanone (CAN 765-43-5). MS (ESI) m/e=345.0 [M+H]$^+$.

Example 44

N-[(2R)-4-Amino-2-cyclopropyl-4-oxobutan-2-yl]-4-cyclopropyl-3-[(propan-2-yl)oxy]benzamide

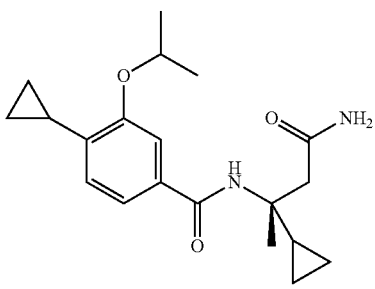 [SMILES: CC(C)Oc1cc(C(=O)N[C@](C)(CC(N)=O)C2CC2)ccc1C1CC1]

The title compound was synthesized in analogy to Example 37d from 4-cyclopropyl-3-(propan-2-yloxy)benzoic acid (Example 37c; 100 mg, 0.45 mmol) and (3R)-3-amino-3-cyclopropylbutanamide hydrochloride (97 mg, 0.54 mmol) as off white solid (45 mg, 29%). (3R)-3-Amino-3-cyclopropylbutanamide hydrochloride was prepared in analogy to 3-cyclopropyl-3-[(2-methylpropane-2-sulfinyl)amino]butanoic acid (CAN 1534510-01-4) starting from (S)-2-methylpropane-2-sulfinamide (CAN 343338-28-3) and 1-cyclopropyl-ethanone (CAN 765-43-5). MS (ESI) m/e=345.0 [M+H]$^+$.

Example 45

N-[(2R)-4-Amino-2-cyclopropyl-4-oxobutan-2-yl]-4-cyclopropyl-3-(2-fluoroethoxy)benzamide

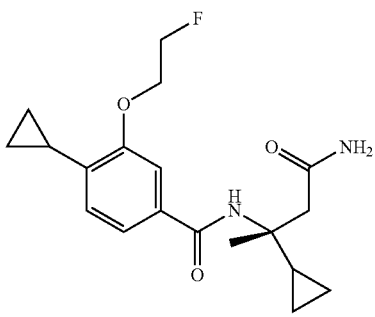 [SMILES: C[C@](CC(N)=O)(NC(=O)c1ccc(C2CC2)c(OCCF)c1)C1CC1]

The title compound was synthesized in analogy to Example 37d from 4-cyclopropyl-3-(2-fluoroethoxy)benzoic acid (Example 33; 100 mg, 0.45 mmol) and (3R)-3-amino-3-cyclopropylbutanamide hydrochloride (Example 44; 96 mg, 0.54 mmol) as off white solid (60 mg, 39%). MS (ESI) m/e=348.8 [M+H]$^+$.

Example 46

3-tert-Butyl-5-{4-cyclopropyl-3-[(propan-2-yl)oxy]phenyl}-1,2,4-oxadiazole

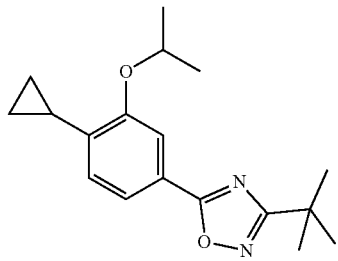 [SMILES: CC(C)Oc1cc(-c2nc(C(C)(C)C)no2)ccc1C1CC1]

To a stirred solution of 4-cyclopropyl-3-(propan-2-yloxy)benzoic acid (Example 37c; 50 mg, 0.22 mmol) in dry DMF (3 mL) was added N,N'-dicyclohexylcarbodiimide (54 mg, 0.33 mmol). The mixture was stirred for 30 min at 25° C. (E)-N'-Hydroxy-2,2-dimethylpropimidamide (39 mg, 0.33 mmol) was added and stirring was continued for 1 h at 25° C. The temperature was raised to 100° C. for 72 h. After cooling to room temperature the concentrated crude mixture was purified by preparative HPLC to give the title compound (34 mg, 51%) as colorless liquid. MS (ESI) m/e=331.2 [M+H]$^+$.

Example 47

3-tert-Butyl-5-[4-cyclopropyl-3-(3,3-difluoropyrrolidin-1-yl)phenyl]-1,2,4-oxadiazole

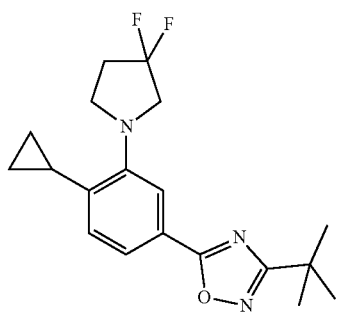 [SMILES: CC(C)(C)c1noc(-c2ccc(C3CC3)c(N3CCC(F)(F)C3)c2)n1]

a) Methyl 4-cyclopropyl-3-(3,3-difluoropyrrolidin-1-yl)benzoate

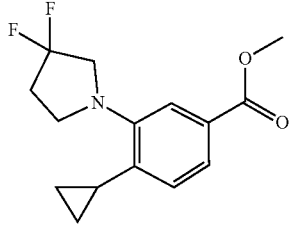 [SMILES: COC(=O)c1ccc(C2CC2)c(N2CCC(F)(F)C2)c1]

To a stirred solution of methyl 3-bromo-4-cyclopropylbenzoate (CAN 1131615-05-8; 1 g, 3.92 mmol) in dioxane (10 mL) were added 3,3-difluoropyrrolidine hydrochloride (1.1 g, 7.84 mmol) and sodium tert-butoxide (1.88 g, 19.6 mmol). The mixture was degassed with nitrogen for 10 min. Ru-Phos (220 mg, 0.47 mmol) and Brett-Phos palladocycle (188 mg, 0.23 mmol) were added. The suspension was degassed 5 min., stirred at 100° C. for 45 h and filtered through a bed of celite. The concentrated filtrate was purified via prep. TLC to obtain the title compound (200 mg, 19%) as off white solid. MS (ESI) m/e=282.2 [M+H]$^+$.

b) 4-Cyclopropyl-3-(3,3-difluoropyrrolidin-1-yl)benzoic acid

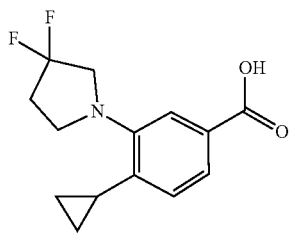 [SMILES: O=C(O)c1ccc(C2CC2)c(N2CCC(F)(F)C2)c1]

The title compound was synthesized in analogy to the procedure described in Example 37c, starting from methyl 4-cyclopropyl-3-(3,3-difluoropyrrolidin-1-yl)benzoate (200 mg, 0.71 mmol) using LiOH×H$_2$O (60 mg, 1.42 mmol) as off white solid (150 mg, 79%). MS (ESI) m/e=268.1 [M+H]$^+$.

c) 3-tert-Butyl-5-[4-cyclopropyl-3-(3,3-difluoropyrrolidin-1-yl)phenyl]-1,2,4-oxadiazole The title compound was synthesized in analogy to Example 46 from 4-cyclopropyl-3-(3,3-difluoropyrrolidin-1-yl)benzoic acid (50 mg, 0.18 mmol) and (E)-N'-hydroxy-2,2-dimethylpropimidamide (32 mg, 0.28 mmol) as colorless liquid (23 mg, 35%). MS (ESI) m/e=348.3 [M+H]$^+$.

Example 48

1-{4-Cyclopropyl-3-[(propan-2-yl)oxy]benzoyl}-4,4-difluoro-L-prolinamide

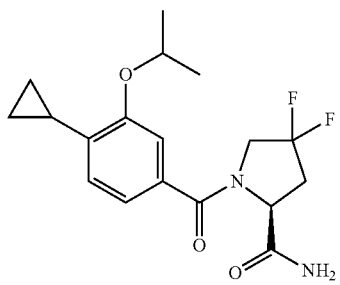 [SMILES: CC(C)Oc1cc(C(=O)N2CC(F)(F)C[C@H]2C(N)=O)ccc1C1CC1]

The title compound was synthesized in analogy to Example 37d from 4-cyclopropyl-3-(propan-2-yloxy)benzoic acid (Example 37c; 100 mg, 0.45 mmol) and (2S)-4,4-difluoropyrrolidine-2-carboxamide hydrochloride (CAN 426844-51-1; 102 mg, 0.54 mmol) as off white solid (18 mg, 11%). MS (ESI) m/e=353.1 [M+H]$^+$.

Example 49

4-Cyclopropyl-N-[(2R)-1-cyclopropyl-2-(5-methyl-1,2,4-oxadiazol-3-yl)propan-2-yl]-3-[(propan-2-yl)oxy]benzamide

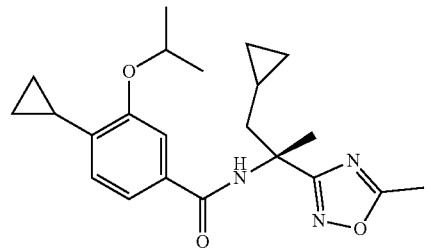 [SMILES: Cc1nc([C@@](C)(CC2CC2)NC(=O)c2ccc(C3CC3)c(OC(C)C)c2)no1]

a) Benzyl N-[(2R)-1-cyclopropyl-2-(5-methyl-1,2,4-oxadiazol-3-yl)propan-2-yl]carbamate

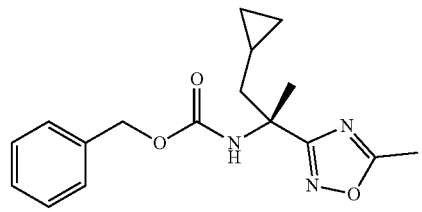 [SMILES: Cc1nc([C@@](C)(CC2CC2)NC(=O)OCc2ccccc2)no1]

To a stirred solution of benzyl N-[2-cyclopropyl-1-(N-hydroxycarbamimidoyl)-1-methylethyl]carbamate (26 g, 89.3 mmol) in isopropyl alcohol (466 mL) was added 1,1 dimethoxy-N,N-dimethylethanamine (47.6 g, 357.4 mmol). The reaction mixture was stirred for 17 h at 25° C. After cooling to 0° C. 4 M hydrochloric acid in dioxane (112 mL, 447 mmol) was added drop wise. Stirring was continued for 2 h at 0° C. Ethyl acetate (300 mL) was added and the mixture was washed with aqueous 2M sodium carbonate solution (500 mL). The aqueous layer was extracted with ethyl acetate (2×300 mL). The combined organic layer was washed with brine (200 mL), dried over anhydrous Na$_2$SO$_4$ and evaporated to dryness. The crude product was purified by combiflash column chromatography eluting with 20-30% ethyl acetate in hexane to obtain racemic benzyl N-[1-cyclopropyl-2-(5-methyl-1,2,4-oxadiazol-3-yl)propan-2-yl]carbamate (25 g, 85%) as colorless sticky oil. Chiral separation provided the title compound (10.5 g, 42%) as colorless sticky oil. MS (ESI) m/e=316.1 [M+H]$^+$.

b) (2R)-1-Cyclopropyl-2-(5-methyl-1,2,4-oxadiazol-3-yl)propan-2-amine

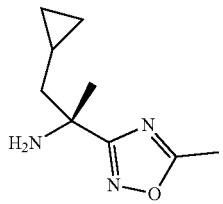

The title compound (5.7 g, 99%) was synthesized in analogy to Example 38g starting from benzyl N-[(2R)-1-cyclopropyl-2-(5-methyl-1,2,4-oxadiazol-3-yl)propan-2-yl] carbamate as light brown liquid.

c) (2R)-1-Cyclopropyl-2-(5-methyl-1,2,4-oxadiazol-3-yl)propan-2-amine hydrochloride

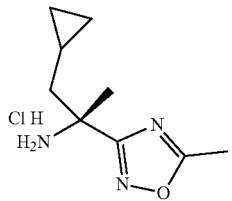

The title compound (6.3 g, 92%) was synthesized in analogy to Example 38h starting from (2R)-1-cyclopropyl-2-(5-methyl-1,2,4-oxadiazol-3-yl)propan-2-amine as off white solid.

d) 4-Cyclopropyl-N-[(2R)-1-cyclopropyl-2-(5-methyl-1,2,4-oxadiazol-3-yl)propan-2-yl]-3-[(propan-2-yl)oxy]benzamide The title compound was synthesized in analogy to Example 37d from 4-cyclopropyl-3-(propan-2-yloxy)benzoic acid (Example 37c; 110 mg, 0.5 mmol) and (2R)-1-cyclopropyl-2-(5-methyl-1,2,4-oxadiazol-3-yl)propan-2-amine hydrochloride (109 mg, 0.5 mmol) as off white solid (31 mg, 16%). MS (ESI) m/e=383.9 [M+H]$^+$.

Example 50

4-Cyclopropyl-N-[(2R)-1-cyclopropyl-2-(5-methyl-1,2,4-oxadiazol-3-yl)propan-2-yl]-3-(6-fluoropyridin-3-yl)benzamide

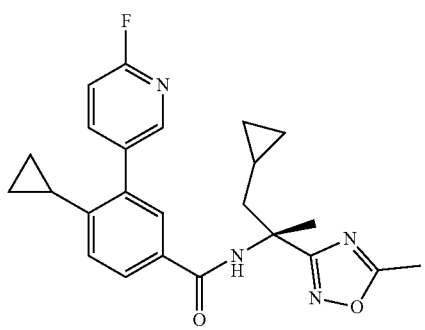 [SMILES: Cc1nc([C@@](C)(CC2CC2)NC(=O)c2ccc(C3CC3)c(-c3ccc(F)nc3)c2)no1]

a) Methyl 4-cyclopropyl-3-(6-fluoropyridin-3-yl)benzoate

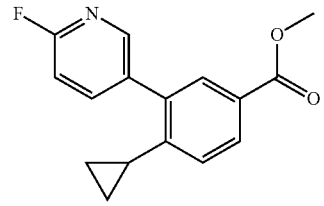 [SMILES: COC(=O)c1ccc(C2CC2)c(-c2ccc(F)nc2)c1]

The title compound was synthesized in analogy to Example 37b starting from methyl 3-bromo-4-cyclopropylbenzoate (CAN 1131615-05-8; 2.0 g, 7.84 mmol) and (6-fluoropyridin-3-yl)boronic acid (2.8 g, 19.6 mmol) as white solid (1.4 g, 66%). MS m/e=271 [M]$^+$.

b) 4-Cyclopropyl-3-(6-fluoropyridin-3-yl)benzoic acid

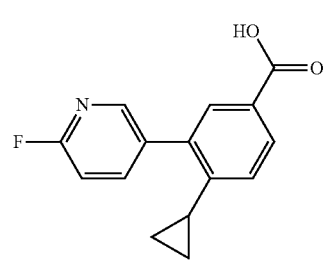 [SMILES: O=C(O)c1ccc(C2CC2)c(-c2ccc(F)nc2)c1]

The title compound was synthesized in analogy to the procedure described in Example 37c, starting from methyl 4-cyclopropyl-3-(6-fluoropyridin-3-yl)benzoate (1.4 g, 5.2 mmol) using LiOH×H$_2$O (433 mg, 10.3 mmol) as white solid (1.3 g, 98%). MS (ESI) m/e=257.9 [M+H]$^+$.

c) 4-Cyclopropyl-N-[(2R)-1-cyclopropyl-2-(5-methyl-1,2,4-oxadiazol-3-yl)propan-2-yl]-3-(6-fluoropyridin-3-yl)benzamide The title compound was synthesized in analogy to Example 37d from 4-cyclopropyl-3-(6-fluoropyridin-3-yl)benzoic acid (110 mg, 0.43 mmol) and (2R)-1-cyclopropyl-2-(5-methyl-1,2,4-oxadiazol-3-yl)propan-2-amine hydrochloride (Example 49c; 93 mg, 0.43 mmol) as off white solid (62 mg, 34%). MS (ESI) m/e=421.0 [M+H]$^+$.

Example 51

N-[(2S)-4-Amino-2-cyclopropyl-4-oxobutan-2-yl]-4-cyclopropyl-3-(2,2,2-trifluoroethoxy)benzamide

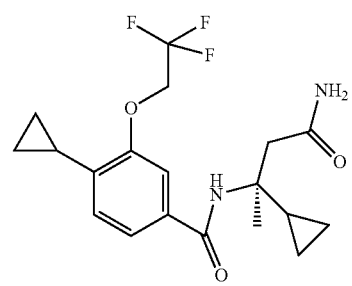 [SMILES: C[C@@](CC(N)=O)(NC(=O)c1ccc(C2CC2)c(OCC(F)(F)F)c1)C1CC1]

The title compound was synthesized in analogy to Example 37d from 4-cyclopropyl-3-(2,2,2-trifluoroethoxy)benzoic acid (Example 25c; 100 mg, 0.38 mmol) and (3S)-3-amino-3-cyclopropylbutanamide hydrochloride (Example 43; 82 mg, 0.46 mmol) as off white solid (50 mg, 34%). MS (ESI) m/e=384.8 [M+H]+.

Example 52

N-[(2R)-4-Amino-2-cyclopropyl-4-oxobutan-2-yl]-4-cyclopropyl-3-(6-fluoropyridin-3-yl)benzamide

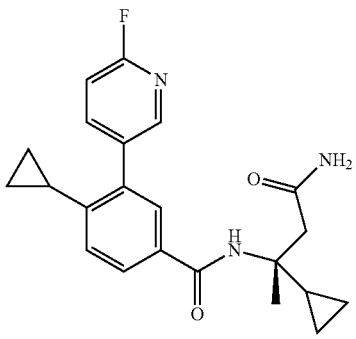 [SMILES: C[C@](CC(N)=O)(NC(=O)c1ccc(C2CC2)c(-c2ccc(F)nc2)c1)C1CC1]

The title compound was synthesized in analogy to Example 37d from 4-cyclopropyl-3-(6-fluoropyridin-3-yl)benzoic acid (Example 50b; 80 mg, 0.31 mmol) and (3R)-3-amino-3-cyclopropylbutanamide hydrochloride (Example 44; 67 mg, 0.37 mmol) as off white solid (65 mg, 55%). MS (ESI) m/e=381.9 [M+H]+.

Example 53

N-[(2S)-4-Amino-2-cyclopropyl-4-oxobutan-2-yl]-4-cyclopropyl-3-(6-fluoropyridin-3-yl)benzamide

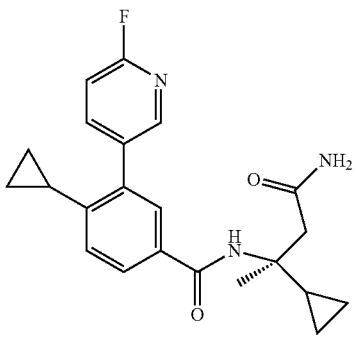 [SMILES: C[C@@](CC(N)=O)(NC(=O)c1ccc(C2CC2)c(-c2ccc(F)nc2)c1)C1CC1]

The title compound was synthesized in analogy to Example 37d from 4-cyclopropyl-3-(6-fluoropyridin-3-yl)benzoic acid (Example 50b; 80 mg, 0.31 mmol) and (3S)-3-amino-3-cyclopropylbutanamide hydrochloride (Example 43; 67 mg, 0.37 mmol) as off white solid (68 mg, 57%). MS (ESI) m/e=381.8 [M+H]+.

Example 54

N-[(2S)-4-Amino-2-cyclopropyl-4-oxobutan-2-yl]-4-cyclopropyl-3-(2-fluoroethoxy)benzamide

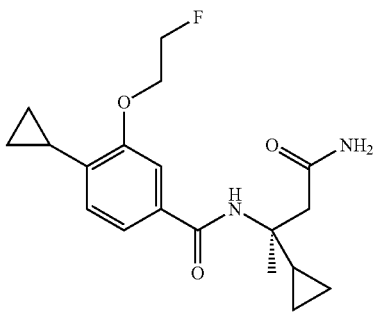 [SMILES: C[C@@](CC(N)=O)(NC(=O)c1ccc(C2CC2)c(OCCF)c1)C1CC1]

The title compound was synthesized in analogy to Example 37d from 4-cyclopropyl-3-(2-fluoroethoxy)benzoic acid (Example 33; 100 mg, 0.45 mmol) and (3S)-3-amino-3-cyclopropylbutanamide hydrochloride (Example 43; 96 mg, 0.53 mmol) as off white solid (75 mg, 42%). MS (ESI) m/e=349.2 [M+H]+.

Example 55

1-[4-Cyclopropyl-3-(1-methyl-1H-pyrazol-5-yl)benzoyl]-4,4-difluoro-L-prolinamide

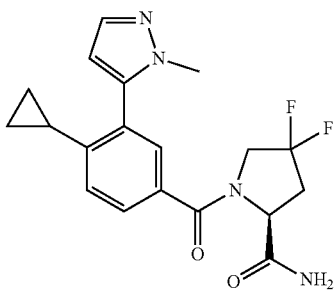 [SMILES: Cn1nccc1-c1cc(C(=O)N2CC(F)(F)C[C@H]2C(N)=O)ccc1C1CC1]

a) Methyl 4-cyclopropyl-3-(3,3-difluoropyrrolidin-1-yl)benzoate

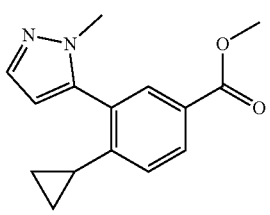 [SMILES: COC(=O)c1ccc(C2CC2)c(-c2ccnn2C)c1]

The title compound was synthesized in analogy to Example 37b starting from methyl 3-bromo-4-cyclopropylbenzoate (CAN 1131615-05-8; 2 g, 7.84 mmol) and 1-methyl-5-(tetramethyl-1,3,2-dioxaborolan-2-yl)-1H-pyrazole (2.4 g, 11.8 mmol) as light brown oil (1.4 g, 70%). MS m/e=256.5 [M]+.

b) 4-Cyclopropyl-3-(1-methyl-1H-pyrazol-5-yl)benzoic acid

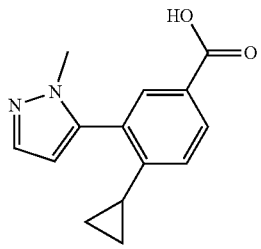 [SMILES: Cn1nccc1-c1cc(C(=O)O)ccc1C1CC1]

The title compound was synthesized in analogy to the procedure described in Example 37c, starting from methyl 4-cyclopropyl-3-(1-methyl-1H-pyrazol-5-yl)benzoate (2 g, 7.8 mmol) using LiOH×H$_2$O (655 mg, 15.6 mmol) as off white solid (1.2 g, 63%). MS (ESI) m/e=241.0 [M−H]$^-$.

c) 1-[4-Cyclopropyl-3-(1-methyl-1H-pyrazol-5-yl)benzoyl]-4,4-difluoro-L-prolinamide The title compound was synthesized in analogy to Example 37d from 4-cyclopropyl-3-(1-methyl-1H-pyrazol-5-yl)benzoic acid (80 mg, 0.33 mmol) and (2S)-4,4-difluoropyrrolidine-2-carboxamide hydrochloride (CAN 426844-51-1; 57 mg, 0.4 mmol) as off white solid (50 mg, 40%). MS (ESI) m/e=375.1 [M+H]$^+$.

Example 56

4-Cyclopropyl-N-[(2S)-3,3-dimethyl-1-(methylamino)-1-oxobutan-2-yl]-3-(1-methyl-1H-pyrazol-5-yl)benzamide

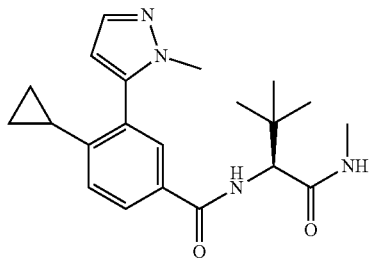 [SMILES: CNC(=O)[C@@H](NC(=O)c1ccc(C2CC2)c(-c2ccnn2C)c1)C(C)(C)C]

The title compound was synthesized in analogy to Example 37d from 4-cyclopropyl-3-(1-methyl-1H-pyrazol-5-yl)benzoic acid (Example 55b; 80 mg, 0.33 mmol) and (2S)-2-amino-N,3,3-trimethylbutanamide (CAN 89226-12-0; 57 g, 0.39 mmol) as off white solid (72 mg, 59%). MS (ESI) m/e=369.2 [M+H]$^+$.

Example 57

1-[4-Cyclopropyl-3-(6-fluoropyridin-3-yl)benzoyl]-4,4-difluoro-L-prolinamide

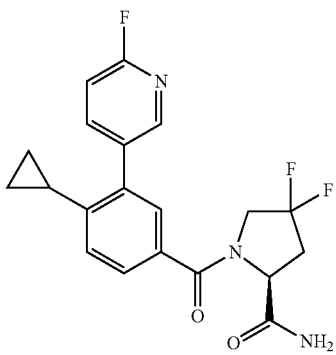 [SMILES: NC(=O)[C@@H]1CC(F)(F)CN1C(=O)c1ccc(C2CC2)c(-c2ccc(F)nc2)c1]

The title compound was synthesized in analogy to Example 37d from 4-cyclopropyl-3-(6-fluoropyridin-3-yl)benzoic acid (Example 50b; 100 mg, 0.39 mmol) and (2S)-4,4-difluoropyrrolidine-2-carboxamide hydrochloride (CAN 426844-51-1; 87 mg, 0.46 mmol) as off white solid (65 mg, 43%). MS (ESI) m/e=390.1 [M+H]$^+$.

Example 58

4-Cyclopropyl-N-[(2S)-3,3-dimethyl-1-(methylamino)-1-oxobutan-2-yl]-3-(6-fluoropyridin-3-yl)benzamide

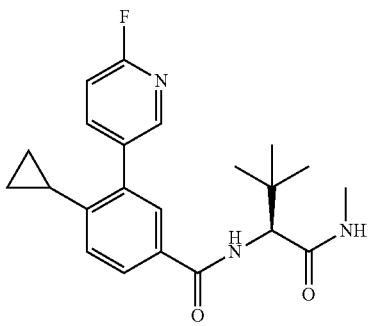 [SMILES: CNC(=O)[C@@H](NC(=O)c1ccc(C2CC2)c(-c2ccc(F)nc2)c1)C(C)(C)C]

The title compound was synthesized in analogy to Example 37d from 4-cyclopropyl-3-(6-fluoropyridin-3-yl)benzoic acid (Example 50b; 100 mg, 0.39 mmol) and (2S)-2-amino-N,3,3-trimethylbutanamide (CAN 89226-12-0; 67 mg, 0.46 mmol) as off white solid (70 mg, 47%). MS (ESI) m/e=384.2 [M+H]$^+$.

Example 59

4-Cyclopropyl-N-[(2S)-1-cyclopropyl-2-(5-methyl-1,2,4-oxadiazol-3-yl)propan-2-yl]-3-(1-methyl-1H-pyrazol-5-yl)benzamide

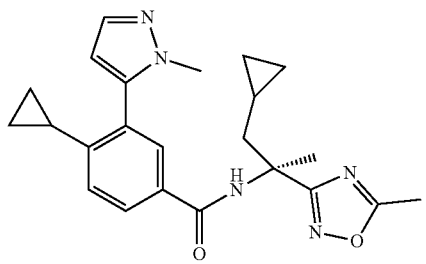 [SMILES: Cc1nc([C@](C)(CC2CC2)NC(=O)c2ccc(C3CC3)c(-c3ccnn3C)c2)no1]

The title compound was synthesized in analogy to Example 37d from 4-cyclopropyl-3-(1-methyl-1H-pyrazol-5-yl)benzoic acid (Example 55b; 110 mg, 0.45 mmol) and (2S)-1-cyclopropyl-2-(5-methyl-1,2,4-oxadiazol-3-yl)propan-2-amine hydrochloride (Example 38h; 99 mg, 0.45 mmol) as off white solid (73 mg, 40%). MS (ESI) m/e=404.2 [M−H]⁻.

Example 60

4-Cyclopropyl-N-[(2S)-1-cyclopropyl-2-(5-methyl-1,2,4-oxadiazol-3-yl)propan-2-yl]-3-(6-fluoropyridin-3-yl)benzamide

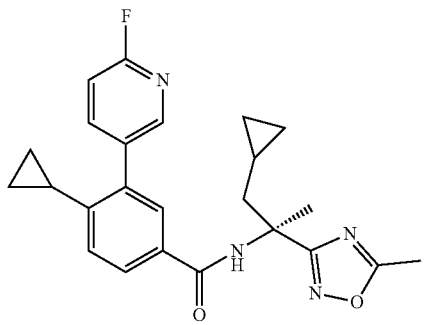 [SMILES: Cc1nc([C@](C)(CC2CC2)NC(=O)c2ccc(C3CC3)c(-c3ccc(F)nc3)c2)no1]

The title compound was synthesized in analogy to Example 37d from 4-cyclopropyl-3-(6-fluoropyridin-3-yl)benzoic acid (Example 50b; 110 mg, 0.43 mmol) and (2S)-1-cyclopropyl-2-(5-methyl-1,2,4-oxadiazol-3-yl)propan-2-amine hydrochloride (Example 38h; 93 mg, 0.43 mmol) as off white solid (49 mg, 27%). MS (ESI) m/e=420.9 [M+H]⁺.

Example 61

N-[(2R)-4-Amino-2-cyclopropyl-4-oxobutan-2-yl]-4-cyclopropyl-3-(3,3-difluoropyrrolidin-1-yl)benzamide

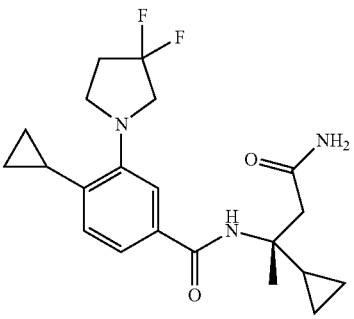 [SMILES: C[C@](CC(N)=O)(NC(=O)c1ccc(C2CC2)c(N2CCC(F)(F)C2)c1)C1CC1]

The title compound was synthesized in analogy to Example 37d from 4-cyclopropyl-3-(3,3-difluoropyrrolidin-1-yl)benzoic acid (65 mg, 0.24 mmol) and (3R)-3-amino-3-cyclopropylbutanamide hydrochloride (Example 44; 52 mg, 0.29 mmol) as off white solid (19 mg, 20%). MS (ESI) m/e=392.1 [M+H]⁺.

Example 62

N-[(2S)-4-Amino-2-cyclopropyl-4-oxobutan-2-yl]-4-cyclopropyl-3-(3,3-difluoropyrrolidin-1-yl)benzamide The title compound was synthesized in analogy to Example 37d from 4-cyclopropyl-3-(3,3-difluoropyrrolidin-1-yl)benzoic acid (60 mg, 0.22 mmol) and (3S)-3-amino-3-cyclopropylbutanamide hydrochloride (Example 43; 40 mg, 0.22 mmol) as off white solid (24 mg, 27%). MS (ESI) m/e=391.7 [M+H]⁺.

Example 63

4-Cyclopropyl-N-[(2R)-1-cyclopropyl-2-(5-methyl-1,2,4-oxadiazol-3-yl)propan-2-yl]-3-(3,3-difluoropyrrolidin-1-yl)benzamide

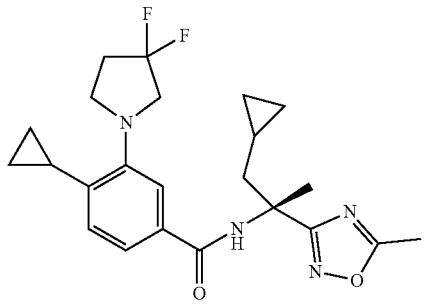 [SMILES: Cc1nc([C@@](C)(CC2CC2)NC(=O)c2ccc(C3CC3)c(N3CCC(F)(F)C3)c2)no1]

The title compound was synthesized in analogy to Example 37d from 4-cyclopropyl-3-(3,3-difluoropyrrolidin-1-yl)benzoic acid (60 mg, 0.22 mmol) and (2R)-1-cyclopropyl-2-(5-methyl-1,2,4-oxadiazol-3-yl)propan-2-amine hydrochloride (Example 49c; 49 mg, 0.22 mmol) as off white solid (35 mg, 36%). MS (ESI) m/e=428.8 [M–H]⁻.

Example 64

4-Cyclopropyl-N-[(2S)-1-cyclopropyl-2-(5-methyl-1,2,4-oxadiazol-3-yl)propan-2-yl]-3-(3,3-difluoropyrrolidin-1-yl)benzamide

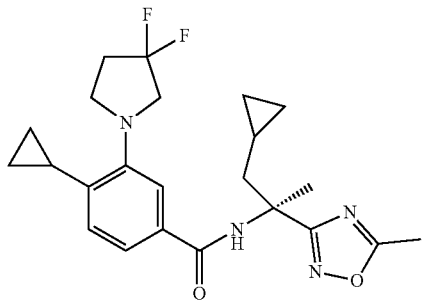 [SMILES: Cc1nc([C@](C)(CC2CC2)NC(=O)c2ccc(C3CC3)c(N3CCC(F)(F)C3)c2)no1]

The title compound was synthesized in analogy to Example 37d from 4-cyclopropyl-3-(3,3-difluoropyrrolidin-1-yl)benzoic acid (65 mg, 0.24 mmol) and (2S)-1-cyclopropyl-2-(5-methyl-1,2,4-oxadiazol-3-yl)propan-2-amine hydrochloride (Example 38h; 63 mg, 0.3 mmol) as off white solid (44 mg, 42%). MS (ESI) m/e=431.2 [M+H]⁺.

Example 65

1-[4-Cyclopropyl-3-(3,3-difluoropyrrolidin-1-yl)benzoyl]-4,4-difluoro-L-prolinamide

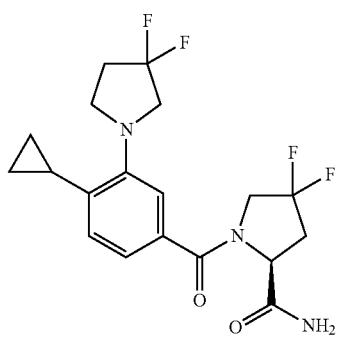 [SMILES: NC(=O)[C@@H]1CC(F)(F)CN1C(=O)c1ccc(C2CC2)c(N2CCC(F)(F)C2)c1]

The title compound was synthesized in analogy to Example 37d from 4-cyclopropyl-3-(3,3-difluoropyrrolidin-1-yl)benzoic acid (50 mg, 0.18 mmol) and (2S)-4,4-difluoropyrrolidine-2-carboxamide hydrochloride (CAN 426844-51-1; 42 mg, 0.22 mmol) as off white solid (50 mg, 67%). MS (ESI) m/e=400.1 [M+H]⁺.

Example 66

4-Cyclopropyl-3-(3,3-difluoropyrrolidin-1-yl)-N-[(2S)-3,3-dimethyl-1-(methylamino)-1-oxobutan-2-yl]benzamide

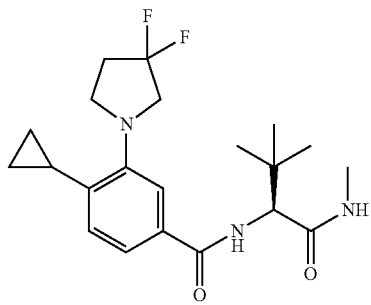 [SMILES: CNC(=O)[C@@H](NC(=O)c1ccc(C2CC2)c(N2CCC(F)(F)C2)c1)C(C)(C)C]

The title compound was synthesized in analogy to Example 37d from 4-cyclopropyl-3-(3,3-difluoropyrrolidin-1-yl)benzoic acid (50 mg, 0.18 mmol) and (2S)-2-amino-N,3,3-trimethylbutanamide (CAN 89226-12-0; 32 mg, 0.22 mmol) as off white solid (20 mg, 28%). MS (ESI) m/e=394.3 [M+H]⁺.

Example 67

4-Cyclopropyl-N-[(5-methyl-1,2,4-oxadiazol-3-yl)(3-methyloxetan-3-yl)methyl]-3-(2,2,2-trifluoroethoxy)benzamide

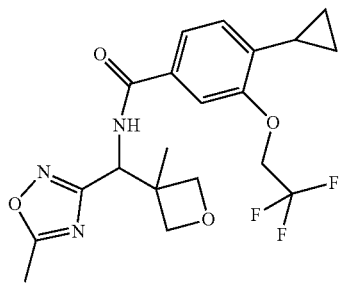 [SMILES: Cc1nc(C(NC(=O)c2ccc(C3CC3)c(OCC(F)(F)F)c2)C2(C)COC2)no1]

a) 2-Methyl-propane-2-sulfinic acid 1-(3-methyl-oxetan-3-yl)-meth-(E)-ylideneamide

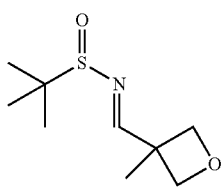

A solution of 3-methyl-oxetane-3-carbaldehyde (15 g, 149.8 mmol), 2-methylpropane-2-sulfinamide (18 g, 149.8 mmol) and Ti(OEt)$_4$ (63 mL, 299.6 mmol) in THE (300 mL) was refluxed for 16 h. The reaction mixture was cooled to 25° C., quenched with brine (800 mL), and extracted with EtOAc (3×300 mL). The combined organic layer was washed with brine (400 mL), dried over anhydrous Na$_2$SO$_4$, filtered, and evaporated in vacuo. The crude product was purified by combiflash column chromatography using 30% EtOAc in hexane as eluents to obtain the title compound (20 g, 66%) as light yellow oil. MS (ESI) m/e=203.9 [M+H]$^+$.

b) 2-Methyl-propane-2-sulfinic acid [cyano-(3-methyl-oxetan-3-yl)-methyl]-amide

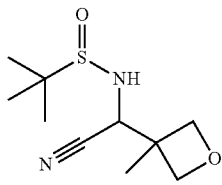

To a stirred solution of 2-methyl-propane-2-sulfinic acid 1-(3-methyl-oxetan-3-yl)-meth-(E)-ylideneamide (4 g, 19.68 mmol) in THE (100 mL) were added cesium fluoride (3.6 g, 23.6 mmol) and trimethyl silyl cyanide (3.1 mL, 23.6 mmol) at 25° C. under a nitrogen atmosphere. The reaction mixture was stirred for 4 h at 25° C. Volatiles were removed in vacuo. The crude mixture was diluted with ethyl acetate (50 mL) and water (50 mL). The layers were separated. The aqueous layer was extracted with EtOAc (2×50 mL). The combined organic layer was washed with brine (20 mL), dried over Na$_2$SO$_4$, filtered and evaporated. The crude product was purified by combiflash column chromatography to obtain the title compound as yellow solid (3.5 g, 78%). MS (ESI) m/e=231.0 [M+H]$^+$.

c) 2-Amino-2-(3-methyloxetan-3-yl)acetonitrile

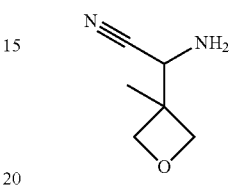

To an ice cold stirred solution of 2-methyl-propane-2-sulfinic acid [cyano-(3-methyl-oxetan-3-yl)-methyl]-amide (1.5 g, 6.51 mmol) in methanol (35 mL) was added a solution of 4 M HCl in dioxane (2.4 mL). The reaction mixture was stirred for 2 h at 0° C. Triethylamine was added (1.8 mL, 13.03 mmol) at 0° C. The volatiles were removed under reduced pressure to obtain the crude title compound (800 mg) which was used in the next step without further purification.

d) N-[Cyano-(3-methyl-oxetan-3-yl)-methyl]-4-cyclopropyl-3-(2,2,2-trifluoro-ethoxy)-benzamide

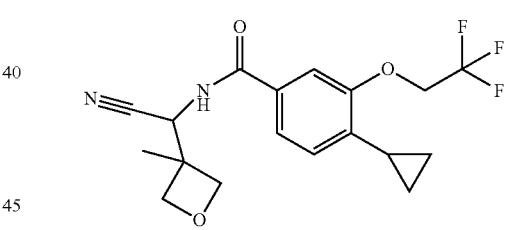

To a stirred solution of 4-cyclopropyl-3-(2,2,2-trifluoro-ethoxy)-benzoic acid (Example 25c; 134 mg, 0.51 mmol) in DMF (1.0 mL) were added DIEA (0.33 mL, 2.1 mmol) and 2-chloro-1-methylpyridinium iodide (336 mg, 1.3 mmol). The mixture was stirred at 25° C. for 1.5 h. Crude 2-amino-2-(3-methyloxetan-3-yl)acetonitrile (130 mg, 1.03 mmol) in DMF (2.0 mL) was added and stirring was continued for 15 h at 25° C. The reaction mixture was diluted with water (10 mL) and extracted with EtOAc (3×20 mL). The combined organic layers were washed with water (10 mL), saturated aqueous NaHCO$_3$ solution (10 mL) and brine (10 mL), dried over anhydrous Na$_2$SO$_4$ and concentrated in vacuo. The crude product was purified by combiflash column chromatography to obtain the title compound as off white solid (150 mg, 40%). MS (ESI) m/e=368.9 [M+H]$^+$.

e) 4-Cyclopropyl-N-[(N-hydroxycarbamimidoyl)-(3-methyl-oxetan-3-yl)-methyl]-3-(2,2,2-trifluoro-ethoxy)-benzamide

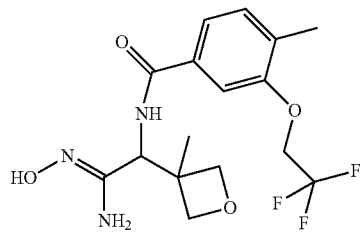 [SMILES: Cc1ccc(C(=O)NC(/C(N)=N/O)C2(C)COC2)cc1OCC(F)(F)F]

To a stirred solution of N-[cyano-(3-methyl-oxetan-3-yl)-methyl]-4-cyclopropyl-3-(2,2,2-trifluoro-ethoxy)-benzamide (150 mg, 0.407 mmol) in ethanol (2 mL) were added triethylamine (61 mL, 0.45 mmol) and hydroxylamine hydrochloride (28 mg, 0.407 mmol). The reaction mixture was stirred at 25° C. for 18 h. The solvent was removed under reduced pressure. The residue was dissolved with 10% methanol in DCM (20 mL). A saturated aqueous solution of NaHCO₃ (20 mL) was added. The organic layer was separated and the aqueous layer was extracted with 10% methanol in DCM (2×20 mL). The combined organic layers were dried over anhydrous Na₂SO₄ and concentrated in vacuo. The crude product was purified via combiflash column chromatography using 90% EtOAc in hexane as eluents to get the title compound as off white sticky solid (100 mg, 61%). MS (ESI) m/e=402.1 [M+H]⁺.

f) 4-Cyclopropyl-N-[(5-methyl-1,2,4-oxadiazol-3-yl)(3-methyloxetan-3-yl)methyl]-3-(2,2,2-trifluoroethoxy)benzamide To a stirred solution of 4-cyclopropyl-N-[(N-hydroxycarbamimidoyl)-(3-methyl-oxetan-3-yl)-methyl]-3-(2,2,2-trifluoro-ethoxy)-benzamide (100 mg, 0.25 mmol) in isopropyl alcohol (2.0 mL) was added (1,1-dimethoxy-ethyl)-dimethyl-amine (265 mg, 1.99 mmol) at 25° C. The reaction mixture was stirred at 25° C. for 17 h. Water (20 mL) and 10% methanol in DCM (20 mL) were added. The organic layer was separated and the aqueous layer was extracted with 10% methanol in DCM (3×20 mL). The combined organic layers were washed with brine (10 mL), dried over Na₂SO₄ and concentrated in vacuo to get the crude product which was purified via combiflash column chromatography using EtOAc as eluent followed by washing with pentane and finally dried via lyophilization to obtain the title compound (20.0 mg, 19%) as off white solid. MS (ESI) m/e=426.0 [M+H]⁺.

Example 68

4-Cyclopropyl-N-[(5-methyl-1,2,4-oxadiazol-3-yl)(3-methyloxetan-3-yl)methyl]-3-[(propan-2-yl)oxy]benzamide

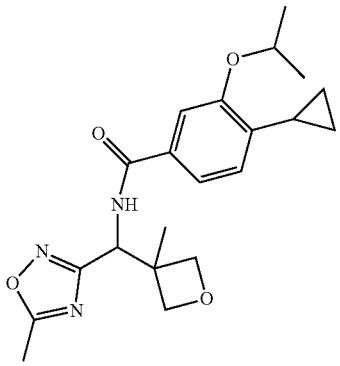 [SMILES: Cc1nc(C(NC(=O)c2ccc(C3CC3)c(OC(C)C)c2)C2(C)COC2)no1]

a) N-[cyano-(3-methyl-oxetan-3-yl)-methyl]-4-cyclopropyl-3-isopropoxy-benzamide

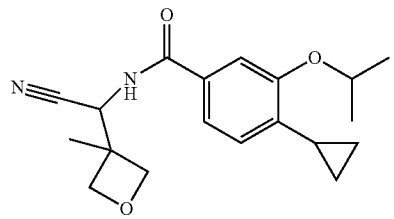 [SMILES: CC(C)Oc1cc(C(=O)NC(C#N)C2(C)COC2)ccc1C1CC1]

The title compound was synthesized in analogy to the procedure described in Example 67d from 4-cyclopropyl-3-(propan-2-yloxy)benzoic acid (Example 37c; 174 mg, 0.79 mmol) and crude 2-amino-2-(3-methyloxetan-3-yl)acetonitrile (Example 67c; 200 mg, 1.58 mmol) as off white solid (250 mg, 48%). MS (ESI) m/e=329.0 [M+H]⁺.

b) 4-Cyclopropyl-N-[(N-hydroxycarbamimidoyl)-(3-methyl-oxetan-3-yl)-methyl]-3-isopropoxy-benzamide

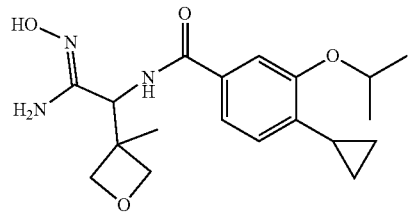 [SMILES: CC(C)Oc1cc(C(=O)NC(/C(N)=N/O)C2(C)COC2)ccc1C1CC1]

The title compound was synthesized in analogy to the procedure described in Example 67e from N-[cyano-(3-methyl-oxetan-3-yl)-methyl]-4-cyclopropyl-3-isopropoxy-benzamide (250 mg, 0.76 mmol) as off white solid (200 mg, 84%). MS (ESI) m/e=362.3 [M+H]⁺.

c) 4-Cyclopropyl-N-[(5-methyl-1,2,4-oxadiazol-3-yl)(3-methyloxetan-3-yl)methyl]-3-[(propan-2-yl)oxy]benzamide The title compound was synthesized in analogy to the procedure described in Example 67f from 4-cyclopropyl-N-[(N-hydroxycarbamimidoyl)-(3-methyl-oxetan-3-yl)-methyl]-3-isopropoxy-benzamide (200 mg, 0.55 mmol) as off white solid (48 mg, 23%). MS (ESI) m/e=386.1 [M+H]⁺.

Example 69

N-[3-Amino-1-(3-methyloxetan-3-yl)-3-oxopropyl]-4-cyclopropyl-3-(2,2,2-trifluoroethoxy)benzamide

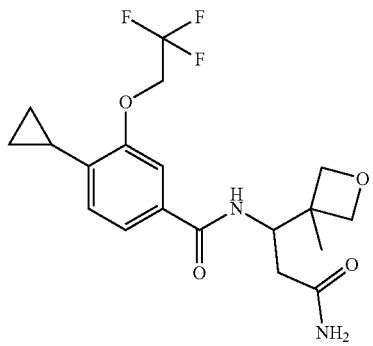 [SMILES: CC1(C(CC(N)=O)NC(=O)c2ccc(C3CC3)c(OCC(F)(F)F)c2)COC1]

a) 3-Methyl-oxetane-3-carboxylic acid benzyl ester

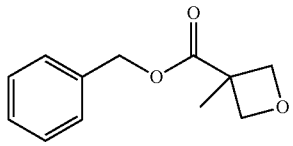

To a solution of 3-methyl-oxetane-3-carboxylic acid (5 g, 43.1 mmol) in CH$_3$CN (100 mL) was added DBU (7.1 mL, 47.4 mmol) and benzyl bromide (5.5 mL, 45.6 mmol). The reaction mixture was stirred for 18 h at 25° C. The solvent was removed under reduced pressure. Ethyl acetate (100 mL) and 1N HCl (20 mL) were added. The organic layer was separated, dried over sodium sulphate and concentrated in vacuo. The crude product was purified via combiflash column chromatography using 10% EtOAc in hexane as eluents to obtain the title compound as colorless liquid (5.4 g. 61%). MS (ESI) m/e=386.1 [M+NH$_4$]+.

b) 3-(3-Methyl-oxetan-3-yl)-3-oxo-propionitrile

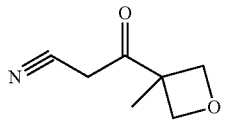

To an ice cold solution of potassium tert-butoxide (2.97 g, 26.47 mmol) in THF (40 mL) was added CH$_3$CN (1.08 g, 26.47 mmol). The mixture was stirred for 10 min at 0° C. A solution of 3-methyl-oxetane-3-carboxylic acid benzyl ester (5.2 g, 25.21 mmol) in THF (10 mL) was added. The reaction mixture was warmed to 25° C. and stirred for 3 h. After cooling to 0° C. 2N aqueous HCl solution (20 mL) was added and the mixture was extracted with CH$_2$Cl$_2$ (2×100 mL). The combined organic layer was washed with brine (10 mL), dried over sodium sulphate and concentrated under reduced pressure. The crude material was purified via combiflash column chromatography using 10% EtOAc in hexane as eluents to obtain the title compound as pale yellow oil (1.7 g, 47%). MS (ESI) m/e=138.1 [M−H]⁻.

c) (Z)-3-[(Benzo[1,3]dioxol-5-ylmethyl)-amino]-3-(3-methyl-oxetan-3-yl)-acrylonitrile

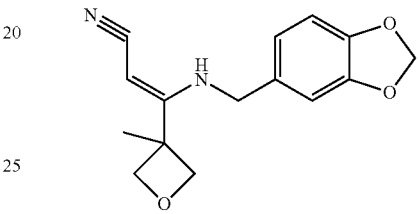

A mixture of 3-(3-methyl-oxetan-3-yl)-3-oxo-propionitrile (1.7 g, 12.21 mmol), 2H-1,3-benzodioxol-5-ylmethanamine (1.84 g, 12.26 mmol) and titanium(IV)isopropoxide (4.56 mL, 15.27 mmol) in THF (15 mL) was stirred at 25° C. for 1 h. Water (50 mL) and EtOAc (100 mL) were added. The mixture was filtered through a bed of Celite and washed with EtOAc (50 mL). The organic layer was separated, washed with brine (20 mL), dried over Na$_2$SO$_4$ and concentrated in vacuo. The crude product was purified via combiflash column chromatography to obtain the title compound as light yellow solid (1.9 g, 57%). MS (ESI) m/e=271.2 [M−H]⁻.

d) 3-[(Benzo[1,3]dioxol-5-ylmethyl)-amino]-3-(3-methyl-oxetan-3-yl)-propionitrile

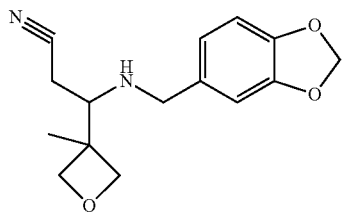 [SMILES: CC1(C(CC#N)NCc2ccc3c(c2)OCO3)COC1]

NaBH$_3$CN (650 mg, 10.47 mmol) was added to a solution of (Z)-3-[(benzo[1,3]dioxol-5-ylmethyl)-amino]-3-(3-methyl-oxetan-3-yl)-acrylonitrile (1.9 g, 6.98 mmol) in AcOH (15 mL). The reaction mixture was stirred at 25° C. for 3 h. The mixture was diluted with water (50 mL) and extracted with EtOAc (3×50 mL). The combined organic layer was washed with saturated aq. NaHCO$_3$ and brine (10 mL), dried over Na$_2$SO$_4$ and concentrated in vacuo. The crude product was purified via combiflash column chromatography using 30% EtOAc in hexane as eluents to get the title compound as colorless gummy solid (1.5 g, 78%). MS (ESI) m/e=275.0 [M+H]⁺.

e) 3-[(Benzo[1,3]dioxol-5-ylmethyl)-amino]-3-(3-methyl-oxetan-3-yl)-propionamide

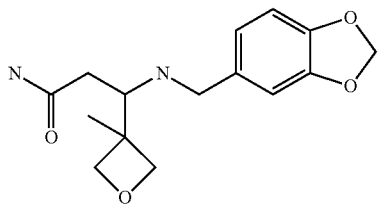 [SMILES: CC1(C(CC(N)=O)NCc2ccc3c(c2)OCO3)COC1]

To a solution of 3-[(benzo[1,3]dioxol-5-ylmethyl)-amino]-3-(3-methyl-oxetan-3-yl)-propionitrile (4.2 g, 15.3 mmol) in DMSO (50 mL) was added $K_2CO_3$ (3.59 g, 26.1 mmol) and drop wise 30% $H_2O_2$ (31 mL). The reaction mixture was stirred at 25° C. for 17 h. Water (200 mL) was added and the suspension was extracted with $CH_2Cl_2$ (2×100 mL). The combined extracts were washed with water (50 mL) and brine (50 mL), dried over $Na_2SO_4$, and concentrated in vacuo. The crude product was purified via combiflash column chromatography using 5% MeOH in DCM as eluents to obtain the title compound as off white gummy liquid (2.35 g, 52%). MS (ESI) m/e=293.0 [M+H]$^+$.

f) 3-Amino-3-(3-methyl-oxetan-3-yl)-propionamide

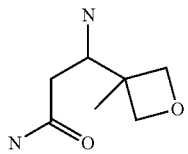

A solution of 3-[(benzo[1,3]dioxol-5-ylmethyl)-amino]-3-(3-methyl-oxetan-3-yl)-propionamide (1 g, 3.42 mmol) in MeOH (70 mL) was purged with argon for 30 min. 20% Pd(OH)$_2$/C (2 g) were added. The mixture was purged with nitrogen for 30 min., stirred for 18 h at 25° C. under $H_2$ balloon pressure and filtrated through a bed of Celite. The Celite bed was washed with 10% MeOH in $CH_2Cl_2$ (2×20 mL). The combined filtrates were concentrated in vacuo. The crude product was triturated with ether (2×20 mL) to get crude title compound as colorless liquid (550 mg) which was used for the next step without any further purification.

g) N-[3-Amino-1-(3-methyloxetan-3-yl)-3-oxopropyl]-4-cyclopropyl-3-(2,2,2-trifluoroethoxy)benzamide To a solution of 4-cyclopropyl-3-(2,2,2-trifluoroethoxy) benzoic acid (Example 25c; 50 mg, 0.192 mmol) in DMF (2 mL) were added DIEA (0.13 mL, 0.78 mmol) and 2-chloro-1-methylpyridinium iodide (122.8 mg, 0.48 mmol). The reaction mixture was stirred for 1.5 h at 25° C. Crude (3-amino-3-(3-methyloxetan-3-yl)propanamide (45.6 mg, 0.288 mmol) in DMF (1.0 mL) was added. Stirring was continued for 16 h at 25° C. The mixture was diluted with water (20 mL) and extracted with ethyl acetate (2×50 mL). The combined organic layer was washed with brine (20 mL), dried over anhydrous $Na_2SO_4$ and concentrated under reduced pressure. Water (10 mL) was added. The suspension was filtered. The obtained off white solid was purified via combiflash column chromatography using EtOAc as eluent to obtain the title compound (23.5 mg, 31%) as off white solid. MS (ESI) m/e=400.9 [M+H]$^+$.

Example 70

4-Cyclopropyl-3-(2-fluoroethoxy)-N-[(5-methyl-1,2,4-oxadiazol-3-yl)(3-methyloxetan-3-yl)methyl]benzamide

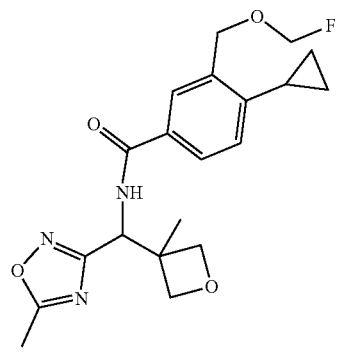 [SMILES: Cc1nc(C(NC(=O)c2ccc(C3CC3)c(COCF)c2)C2(C)COC2)no1]

a) N-[Cyano-(3-methyl-oxetan-3-yl)-methyl]-4-cyclopropyl-3-(2-fluoro-ethoxy)-benzamide

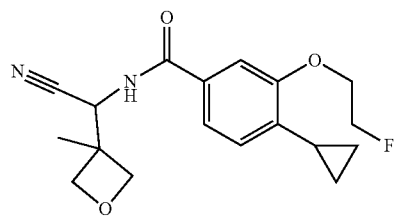 [SMILES: CC1(C(C#N)NC(=O)c2ccc(C3CC3)c(OCCF)c2)COC1]

The title compound was synthesized in analogy to the procedure described in Example 67d from 4-cyclopropyl-3-(2-fluoroethoxy)benzoic acid (Example 33; 240 mg, 1.07 mmol) and crude 2-amino-2-(3-methyloxetan-3-yl)acetonitrile (Example 67c; 270 mg, 1.07 mmol) as off white solid (250 mg, 35%). MS (ESI) m/e=333.1 [M+H]$^+$.

b) 4-Cyclopropyl-3-(2-fluoro-ethoxy)-N-[(N-hydroxycarbamimidoyl)-(3-methyl-oxetan-3-yl)-methyl]-benzamide

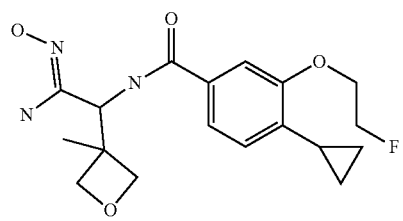 [SMILES: CC1(C(NC(=O)c2ccc(C3CC3)c(OCCF)c2)/C(N)=N/O)COC1]

The title compound was synthesized in analogy to the procedure described in Example 67e from N-[cyano-(3-methyl-oxetan-3-yl)-methyl]-4-cyclopropyl-3-(2-fluoroethoxy)-benzamide (250 mg, 0.75 mmol) as off white solid (200 mg, 73%). MS (ESI) m/e=365.9 [M+H]$^+$.

c) 4-Cyclopropyl-3-(2-fluoroethoxy)-N-[(5-methyl-1,2,4-oxadiazol-3-yl)(3-methyloxetan-3-yl)methyl]benzamide The title compound was synthesized in analogy to the procedure described in Example 67f from 4-cyclopropyl-3-(2-fluoro-ethoxy)-N-[(N-hydroxycarbamimidoyl)-(3-methyl-oxetan-3-yl)-methyl]-benzamide (200 mg, 0.55 mmol) and (1,1-dimethoxy-ethyl)-dimethyl-amine (583 mg, 4.38 mmol) as off white solid (168 mg, 79%). MS (ESI) m/e=390.0 [M+H]$^+$.

Example 71

Pharmacological Tests

The following tests were carried out in order to determine the activity of the compounds of formula I:

Radioligand Binding Assay

The affinity of the compounds of the invention for cannabinoid CB1 receptors was determined using recommended amounts of membrane preparations (PerkinElmer) of human embryonic kidney (HEK) cells expressing the human CNR1 or CNR2 receptors in conjunction with 1.5 or 2.6 nM [3H]-CP-55,940 (Perkin Elmer) as radioligand, respectively. Binding was performed in binding buffer (50 mM Tris, 5 mM MgCl2, 2.5 mM EDTA, and 0.5% (wt/vol) fatty acid free BSA, pH 7.4 for CB1 receptor and 50 mM Tris, 5 mM MgCl$_2$, 2.5 mM EGTA, and 0.1% (wt/vol) fatty acid free BSA, pH 7.4 for CB2 receptor) in a total volume of 0.2 ml for 1 h at 30° C. shaking. The reaction was terminated by rapid filtration through microfiltration plates coated with 0.5% polyethylenimine (UniFilter GF/B filter plate; Packard). Bound radioactivity was analyzed for Ki using nonlinear regression analysis (Activity Base, ID Business Solution, Limited), with the Kd values for [3H]CP55,940 determined from saturation experiments. The compounds of formula (I) show an excellent affinity for the CB2 receptor with affinities below μM, more particularly of 1 nM to 3 μM and most particularly of 1 nM to 100 nM.

cAMP Assay

CHO cells expressing human CB1 or CB2 receptors are seeded 17-24 hours prior to the experiment 50.000 cells per well in a black 96 well plate with flat clear bottom (Corning Costar #3904) in DMEM (Invitrogen No. 31331), 1×HT supplement, with 10% fetal calf serum and incubated at 5% CO$_2$ and 37° C. in a humidified incubator. The growth medium was exchanged with Krebs Ringer Bicarbonate buffer with 1 mM IBMX and incubated at 30° C. for 30 min. Compounds were added to a final assay volume of 100 μl and incubated for 30 min at 30° C. Using the cAMP-Nano-TRF detection kit the assay (Roche Diagnostics) was stopped by the addition of 50 μl lysis reagent (Tris, NaCl, 1.5% Triton X100, 2.5% NP40, 10% NaN$_3$) and 50 μl detection solutions (20 μM mAb Alexa700-cAMP 1:1, and 48 μM Ruthenium-2-AHA-cAMP) and shaken for 2 h at room temperature. The time-resolved energy transfer is measured by a TRF reader (Evotec Technologies GmbH), equipped with a ND:YAG laser as excitation source. The plate is measured twice with the excitation at 355 nm and at the emission with a delay of 100 ns and a gate of 100 ns, total exposure time 10 s at 730 (bandwidth 30 nm) or 645 nm (bandwidth 75 nm), respectively. The FRET signal is calculated as follows: FRET=T730-Alexa730-P(T645-B645) with P=Ru730-B730/Ru645-B645, where T730 is the test well measured at 730 nM, T645 is the test well measured at 645 nm, B730 and B645 are the buffer controls at 730 nm and 645 nm, respectively. cAMP content is determined from the function of a standard curve spanning from 10 μM to 0.13 nM cAMP.

EC$_{50}$ values were determined using Activity Base analysis (ID Business Solution, Limited). The EC$_{50}$ values for a wide range of cannabinoid agonists generated from this assay were in agreement with the values published in the scientific literature.

The compounds of the invention are CB2 agonists with EC$_{50}$ below 0.5 M and selectivity versus CB1 in the corresponding assay of at least 10 fold. Particular compound of the invention are CB2 agonists with EC$_{50}$ below 0.05 M and selectivity versus CB1 in the corresponding assay of at least 500 fold.

For example, the following compounds showed the following human EC$_{50}$ values in the functional cAMP assay described above:

| Example | Human CB2 EC$_{50}$ (uM) | Human CB1 EC$_{50}$ (uM) |
|---|---|---|
| 1 | 0.13611 | >10 |
| 2 | 0.49179 | >10 |
| 3 | 0.12205 | >10 |
| 4 | 0.01804 | >10 |
| 5 | 0.12961 | >10 |
| 6 | 0.02604 | 0.53879 |
| 7 | 0.00144 | >10 |
| 8 | 2.1742 | >10 |
| 9 | 0.00756 | >10 |
| 10 | 0.03294 | >10 |
| 11 | 0.09872 | >10 |
| 12 | 0.06641 | >10 |
| 13 | 0.02182 | >10 |
| 14 | 0.02328 | >10 |
| 15 | 0.03409 | >10 |
| 16 | 0.00265 | >10 |
| 17 | 0.00051 | >10 |
| 18 | 0.23258 | >10 |
| 19 | 0.0196 | >10 |
| 20 | 0.03128 | >10 |
| 21 | 0.29716 | >10 |
| 22 | 0.0281 | >10 |
| 23 | 0.02589 | >10 |
| 24 | 0.01546 | >10 |
| 25 | 0.040295 | >10 |
| 26 | 0.03631 | >10 |
| 27 | 0.09796 | >10 |
| 28 | 0.07985 | >10 |
| 29 | 0.14868 | >10 |
| 30 | 0.03834 | >10 |
| 31 | 0.01662 | >10 |
| 32 | 0.01005 | >10 |
| 33 | 0.059395 | >10 |
| 34 | 0.05695 | >10 |
| 35 | 0.00856 | >10 |
| 36 | 0.03388 | >10 |
| 37 | 0.00533 | >10 |
| 38 | 0.02662 | >10 |
| 39 | 0.01151 | 1.5586 |
| 40 | 0.21552 | >10 |
| 41 | 0.010025 | 0.585855 |
| 42 | 0.13441 | >10 |
| 43 | 0.03084 | >10 |
| 44 | 0.002905 | 1.0894 |
| 45 | 0.00742 | >10 |
| 47 | 0.00533 | >10 |
| 48 | 0.37708 | >10 |
| 49 | 0.04212 | >10 |
| 50 | 0.05368 | >10 |
| 51 | 0.08084 | >10 |
| 52 | 0.00976 | >10 |
| 53 | 0.18363 | >10 |

-continued

| Example | Human CB2 $EC_{50}$ (uM) | Human CB1 $EC_{50}$ (uM) |
|---|---|---|
| 54 | 0.23085 | >10 |
| 55 | 1.91253 | >10 |
| 56 | 0.14008 | >10 |
| 57 | 0.27384 | >10 |
| 58 | 0.01177 | 0.38833 |
| 59 | 0.28233 | >10 |
| 60 | 0.09837 | >10 |
| 61 | 0.0025 | 1.78648 |
| 62 | 0.02594 | >10 |
| 63 | 0.00383 | 0.87196 |
| 64 | 0.00108 | >10 |
| 65 | 0.01813 | >10 |
| 66 | 0.00048 | 0.042115 |
| 67 | 0.26284 | >10 |
| 68 | 0.26368 | >10 |
| 69 | 1.18458 | >10 |
| 70 | 0.50609 | >10 |

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcrystalline cellulose and the mixture is granulated with a solution of polyvinylpyrrolidone in water. The granulate is then mixed with sodium starch glycolate and magnesium stearate and compressed to yield kernels of 120 or 350 mg respectively. The kernels are lacquered with an aq. solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| Compound of formula (I) | 3.0 mg |
|---|---|
| Polyethylene glycol 400 | 150.0 mg |
| Acetic acid | q.s. ad pH 5.0 |
| Water for injection solutions | ad 1.0 ml |

The active ingredient is dissolved in a mixture of Polyethylene glycol 400 and water for injection (part). The pH is adjusted to 5.0 by addition of acetic acid. The volume is adjusted to 1.0 ml by addition of the residual amount of water. The solution is filtered, filled into vials using an appropriate overage and sterilized.

The invention claimed is:
1. A compound of formula (I)

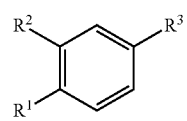

wherein
$R^1$ is cyclopropyl, alkyl or haloazetidinyl;
$R^2$ is cyclopropylmethoxy, alkoxy, haloalkoxy, halopyridinyl, alkylpyrazolyl or halopyrrolidinyl;
provided that at least one of $R^1$ and $R^2$ is cyclopropyl or cyclopropylmethoxy;
$R^3$ is —C(O)—NH—C($R^4R^5$)—$R^6$, —C(O)—$R^7$ or $R^8$;
$R^4$ and $R^5$ are independently selected from hydrogen, alkyl, cycloalkyl, cycloalkylalkyl, alkyl sulfonyl alkyl and alkyloxetanyl;
or $R^4$ and $R^5$ together with the carbon atom to which they are attached form oxetanyl or dioxothiethanyl;
$R^6$ is aminocarbonyl, 5-methyl-1,2,4-oxadiazol-3-yl, hydroxyalkyl, thiazolyl, alkoxycarbonyl, carboxy, difluoroazetidinylcarbonyl, 5-amino-1,2,4-oxadiazol-3-yl, alkylaminocarbonyl or aminocarbonylalkyl;
$R^7$ is (aminocarbonyl)(difluoro)pyrrolidinyl or (aminocarbonyl)azaspiro[2.4]heptyl; and
$R^8$ is 3-alkyl-1,2,4-oxadiazol-5-yl or 5-alkyl-1,2,4-oxadiazol-3-yl;
or a pharmaceutically acceptable salt or ester thereof.
2. The compound according to claim 1, wherein $R^1$ is cyclopropyl.
3. The compound according to claim 1, wherein $R^2$ is cyclopropylmethoxy, alkoxy, haloalkoxy or halopyrrolidinyl.
4. The compound according to claim 1, wherein $R^2$ is cyclopropylmethoxy, propyloxy, fluoroethoxy, trifluoroethoxy or difluoropyrrolidinyl.
5. The compound according to claim 1, wherein $R^4$ and $R^5$ are independently selected from the group consisting of hydrogen, alkyl, cycloalkyl and cycloalkylalkyl.
6. The compound according to claim 1, wherein $R^4$ and $R^5$ are independently selected from the group consisting of hydrogen, methyl, butyl, cyclopropyl and cyclopropylmethyl.
7. The compound according to claim 1, wherein $R^6$ is aminocarbonyl, 5-methyl-1,2,4-oxadiazol-3-yl, hydroxyalkyl or alkylaminocarbonyl.

8. The compound according to claim 1, wherein $R^6$ is aminocarbonyl, 5-methyl-1,2,4-oxadiazol-3-yl, hydroxymethyl or methyl aminocarbonyl.

9. The compound according to claim 1, wherein $R^7$ is (aminocarbonyl)(difluoro)pyrrolidinyl.

10. The compound according to claim 1, wherein $R^8$ is 3-tert-butyl-1,2,4-oxadiazol-5-yl, 5-tert-butyl-1,2,4-oxadiazol-3-yl or 5-methyl-1,2,4-oxadiazol-3-yl.

11. The compound according to claim 1, wherein the compound is selected from the group consisting of:

(R)—N-(1-amino-4-methyl-1-oxopentan-2-yl)-3-(cyclopropylmethoxy)-4-methylbenzamide;

3-(cyclopropylmethoxy)-4-methyl-N-[2-(5-methyl-1,2,4-oxadiazol-3-yl)propan-2-yl]benzamide;

4-cyclopropyl-3-(cyclopropylmethoxy)-N-[2-(5-methyl-1,2,4-oxadiazol-3-yl)propan-2-yl]benzamide;

$N^2$-[4-cyclopropyl-3-(cyclopropylmethoxy)benzoyl]-L-leucinamide;

4-cyclopropyl-3-(cyclopropylmethoxy)-N-(1-hydroxy-2-methylpropan-2-yl)benzamide;

4-cyclopropyl-3-(cyclopropylmethoxy)-N-[2-(1,3-thiazol-2-yl)propan-2-yl]benzamide;

ethyl 2-[4-cyclopropyl-3-(cyclopropylmethoxy)benzamido]-2-ethylbutanoate;

2-[4-cyclopropyl-3-(cyclopropylmethoxy)benzamido]-2-ethylbutanoic acid;

4-cyclopropyl-3-(cyclopropylmethoxy)-N-[3-(3,3-difluoroazetidine-1-carbonyl)pentan-3-yl]benzamide;

3-(cyclopropylmethoxy)-4-(3,3-difluoroazetidin-1-yl)-N-[2-(5-methyl-1,2,4-oxadiazol-3-yl)propan-2-yl]benzamide;

N-[2-(5-amino-1,2,4-oxadiazol-3-yl)propan-2-yl]-3-(cyclopropylmethoxy)-4-(3,3-difluoroazetidin-1-yl)benzamide;

$N^2$-[3-(cyclopropylmethoxy)-4-(3,3-difluoroazetidin-1-yl)benzoyl]-N-methyl-L-leucinamide;

3-(cyclopropylmethoxy)-4-(3,3-difluoroazetidin-1-yl)-N-[(2S)-1-hydroxy-4-methylpentan-2-yl]benzamide;

3-tert-butyl-5-[4-cyclopropyl-3-(cyclopropylmethoxy)phenyl]-1,2,4-oxadiazole;

N-[3-(2-amino-2-oxoethyl)oxetan-3-yl]-4-cyclopropyl-3-(cyclopropylmethoxy)benzamide;

N-[3-(2-amino-2-oxoethyl)-1,1-dioxothietan-3-yl]-4-cyclopropyl-3-(cyclopropylmethoxy)benzamide;

1-[4-cyclopropyl-3-(cyclopropylmethoxy)benzoyl]-4,4-difluoro-L-prolinamide;

N-(3-carbamoylpentan-3-yl)-4-cyclopropyl-3-(cyclopropylmethoxy)benzamide;

$N^2$-[4-cyclopropyl-3-(cyclopropylmethoxy)benzoyl]-N-methyl-L-leucinamide;

4-cyclopropyl-3-(cyclopropylmethoxy)-N-[(2S)-1-(methanesulfonyl)-2-(5-methyl-1,2,4-oxadiazol-3-yl)propan-2-yl]benzamide;

4-cyclopropyl-3-(cyclopropylmethoxy)-N-[(2R)-1-(methanesulfonyl)-2-(5-methyl-1,2,4-oxadiazol-3-yl)propan-2-yl]benzamide;

5-[4-cyclopropyl-3-(cyclopropylmethoxy)benzoyl]-5-azaspiro[2.4]heptane-6-carboxamide;

5-tert-butyl-3-[4-cyclopropyl-3-(2,2,2-trifluoroethoxy)phenyl]-1,2,4-oxadiazole;

5-tert-butyl-3-[4-cyclopropyl-3-(2,2-difluoroethoxy)phenyl]-1,2,4-oxadiazole;

4-cyclopropyl-N-[(2R)-1-cyclopropyl-2-(5-methyl-1,2,4-oxadiazol-3-yl)propan-2-yl]-3-(2,2,2-trifluoroethoxy)benzamide;

4-cyclopropyl-N-[(2S)-1-cyclopropyl-2-(5-methyl-1,2,4-oxadiazol-3-yl)propan-2-yl]-3-(2,2,2-trifluoroethoxy)benzamide;

N-[3-(2-amino-2-oxoethyl)-1,1-dioxo-thietan-3-yl]-4-cyclopropyl-3-(2,2,2-trifluoroethoxy)benzamide;

4-cyclopropyl-N-[(2R)-1-(methanesulfonyl)-2-(5-methyl-1,2,4-oxadiazol-3-yl)propan-2-yl]-3-(2,2,2-trifluoroethoxy)benzamide;

4-cyclopropyl-N-[(2 S)-1-(methanesulfonyl)-2-(5-methyl-1,2,4-oxadiazol-3-yl)propan-2-yl]-3-(2,2,2-trifluoroethoxy)benzamide;

5-tert-butyl-3-[4-cyclopropyl-3-(2-fluoroethoxy)phenyl]-1,2,4-oxadiazole;

4-cyclopropyl-N-[(2R)-1-cyclopropyl-2-(5-methyl-1,2,4-oxadiazol-3-yl)propan-2-yl]-3-(2,2-difluoroethoxy)benzamide;

4-cyclopropyl-N-[(2S)-1-cyclopropyl-2-(5-methyl-1,2,4-oxadiazol-3-yl)propan-2-yl]-3-(2,2-difluoroethoxy)benzamide;

4-cyclopropyl-N-[(2R)-1-cyclopropyl-2-(5-methyl-1,2,4-oxadiazol-3-yl)propan-2-yl]-3-(2-fluoroethoxy)benzamide;

4-cyclopropyl-N-[(2S)-1-cyclopropyl-2-(5-methyl-1,2,4-oxadiazol-3-yl)propan-2-yl]-3-(2-fluoroethoxy)benzamide;

N-[(2S)-4-amino-2-cyclopropyl-4-oxobutan-2-yl]-4-cyclopropyl-3-(2,2,2-trifluoroethoxy)benzamide;

N-[(2R)-4-amino-2-cyclopropyl-4-oxobutan-2-yl]-4-cyclopropyl-3-(2,2,2-trifluoroethoxy)benzamide;

4-cyclopropyl-N-[(2S)-3,3-dimethyl-1-(methylamino)-1-oxobutan-2-yl]-3-[(propan-2-yl)oxy]benzamide;

4-cyclopropyl-N-[(2S)-1-cyclopropyl-2-(5-methyl-1,2,4-oxadiazol-3-yl)propan-2-yl]-3-[(propan-2-yl)oxy]benzamide;

4-cyclopropyl-N-[(2S)-3,3-dimethyl-1-(methylamino)-1-oxobutan-2-yl]-3-(2-fluoroethoxy)benzamide;

1-[4-cyclopropyl-3-(2-fluoroethoxy)benzoyl]-4,4-difluoro-L-prolinamide;

4-cyclopropyl-N-[(2S)-3,3-dimethyl-1-(methylamino)-1-oxobutan-2-yl]-3-(2,2,2-trifluoroethoxy)benzamide;

1-[4-cyclopropyl-3-(2,2,2-trifluoroethoxy)benzoyl]-4,4-difluoro-L-prolinamide;

N-[(2S)-4-amino-2-cyclopropyl-4-oxobutan-2-yl]-4-cyclopropyl-3-[(propan-2-yl)oxy]benzamide;

N-[(2R)-4-amino-2-cyclopropyl-4-oxobutan-2-yl]-4-cyclopropyl-3-[(propan-2-yl)oxy]benzamide;

N-[(2R)-4-amino-2-cyclopropyl-4-oxobutan-2-yl]-4-cyclopropyl-3-(2-fluoroethoxy)benzamide;

3-tert-butyl-5-{4-cyclopropyl-3-[(propan-2-yl)oxy]phenyl}-1,2,4-oxadiazol e;

3-tert-butyl-5-[4-cyclopropyl-3-(3,3-difluoropyrrolidin-1-yl)phenyl]-1,2,4-oxadiazole;

1-{4-cyclopropyl-3-[(propan-2-yl)oxy]benzoyl}-4,4-difluoro-L-prolinamide;

4-cyclopropyl-N-[(2R)-1-cyclopropyl-2-(5-methyl-1,2,4-oxadiazol-3-yl)propan-2-yl]-3-[(propan-2-yl)oxy]benzamide;

4-cyclopropyl-N-[(2R)-1-cyclopropyl-2-(5-methyl-1,2,4-oxadiazol-3-yl)propan-2-yl]-3-(6-fluoropyridin-3-yl)benzamide;

N-[(2R)-4-amino-2-cyclopropyl-4-oxobutan-2-yl]-4-cyclopropyl-3-(6-fluoropyridin-3-yl)benzamide;

N-[(2S)-4-amino-2-cyclopropyl-4-oxobutan-2-yl]-4-cyclopropyl-3-(6-fluoropyridin-3-yl)benzamide;

N-[(2S)-4-amino-2-cyclopropyl-4-oxobutan-2-yl]-4-cyclopropyl-3-(2-fluoroethoxy)benzamide;

1-[4-cyclopropyl-3-(1-methyl-1H-pyrazol-5-yl)benzoyl]-4,4-difluoro-L-prolinamide;
4-cyclopropyl-N-[(2S)-3,3-dimethyl-1-(methylamino)-1-oxobutan-2-yl]-3-(1-methyl-1H-pyrazol-5-yl)benzamide;
1-[4-cyclopropyl-3-(6-fluoropyridin-3-yl)benzoyl]-4,4-difluoro-L-prolinamide;
4-cyclopropyl-N-[(2S)-3,3-dimethyl-1-(methylamino)-1-oxobutan-2-yl]-3-(6-fluoropyridin-3-yl)benzamide;
4-cyclopropyl-N-[(2 S)-1-cyclopropyl-2-(5-methyl-1,2,4-oxadiazol-3-yl)propan-2-yl]-3-(1-methyl-1H-pyrazol-5-yl)benzamide;
4-cyclopropyl-N-[(2 S)-1-cyclopropyl-2-(5-methyl-1,2,4-oxadiazol-3-yl)propan-2-yl]-3-(6-fluoropyridin-3-yl)benzamide;
N-[(2R)-4-amino-2-cyclopropyl-4-oxobutan-2-yl]-4-cyclopropyl-3-(3,3-difluoropyrrolidin-1-yl)benzamide;
N-[(2S)-4-amino-2-cyclopropyl-4-oxobutan-2-yl]-4-cyclopropyl-3-(3,3-difluoropyrrolidin-1-yl)benzamide;
4-cyclopropyl-N-[(2R)-1-cyclopropyl-2-(5-methyl-1,2,4-oxadiazol-3-yl)propan-2-yl]-3-(3,3-difluoropyrrolidin-1-yl)benzamide;
4-cyclopropyl-N-[(2 S)-1-cyclopropyl-2-(5-methyl-1,2,4-oxadiazol-3-yl)propan-2-yl]-3-(3,3-difluoropyrrolidin-1-yl)benzamide;
1-[4-cyclopropyl-3-(3,3-difluoropyrrolidin-1-yl)benzoyl]-4,4-difluoro-L-prolinamide;
4-cyclopropyl-3-(3,3-difluoropyrrolidin-1-yl)-N-(2S)-3,3-dimethyl-1-(methylamino)-1-oxobutan-2-yl]benzamide;
4-cyclopropyl-N-[(5-methyl-1,2,4-oxadiazol-3-yl)(3-methyloxetan-3-yl)methyl]-3-(2,2,2-trifluoroethoxy)benzamide;
4-cyclopropyl-N-[(5-methyl-1,2,4-oxadiazol-3-yl)(3-methyloxetan-3-yl)methyl]-3-[(propan-2-yl)oxy]benzamide;
N-[3-amino-1-(3-methyloxetan-3-yl)-3-oxopropyl]-4-cyclopropyl-3-(2,2,2-trifluoroethoxy)benzamide; and
4-cyclopropyl-3-(2-fluoroethoxy)-N-[(5-methyl-1,2,4-oxadiazol-3-yl)(3-methyloxetan-3-yl)methyl]benzamide;
or a pharmaceutically acceptable salt thereof.

12. The compound according to claim 1, wherein the compound is selected from the group consisting of:
N²[4-cyclopropyl-3-(cyclopropylmethoxy)benzoyl]-L-leucinamide,
4-cyclopropyl-3-(cyclopropylmethoxy)-N-(1-hydroxy-2-methylpropan-2-yl)benzamide;
3-tert-butyl-5-[4-cyclopropyl-3-(cyclopropylmethoxy)phenyl]-1,2,4-oxadiazole;
N-[3-(2-amino-2-oxoethyl)oxetan-3-yl]-4-cyclopropyl-3-(cyclopropylmethoxy)benzamide;
N-[3-(2-amino-2-oxoethyl)-1,1-dioxothietan-3-yl]-4-cyclopropyl-3-(cyclopropylmethoxy)benzamide;
1-[4-cyclopropyl-3-(cyclopropylmethoxy)benzoyl]-4,4-difluoro-L-prolinamide;
5-tert-butyl-3-[4-cyclopropyl-3-(2-fluoroethoxy)phenyl]-1,2,4-oxadiazole;
N-[(2S)-4-amino-2-cyclopropyl-4-oxobutan-2-yl]-4-cyclopropyl-3-(2,2,2-trifluoroethoxy)benzamide;
4-cyclopropyl-N-[(2S)-3,3-dimethyl-1-(methylamino)-1-oxobutan-2-yl]-3-[(propan-2-yl)oxy]benzamide;
4-cyclopropyl-N-[(2S)-1-cyclopropyl-2-(5-methyl-1,2,4-oxadiazol-3-yl)propan-2-yl]-3-[(propan-2-yl)oxy]benzamide; and
N-[(2R)-4-amino-2-cyclopropyl-4-oxobutan-2-yl]-4-cyclopropyl-3-[(propan-2-yl)oxy]benzamide;
or a pharmaceutically acceptable salt thereof.

13. A process for the preparation of a compound according to claim 1, comprising one of the following steps:
(a) reacting a compound of formula (A)

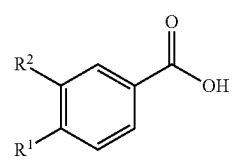

(A)

in the presence of $H_2N-C(R^4R^5)-R^6$, a coupling agent and a base, wherein $R^2$ is cyclopropylmethoxy, alkoxy or haloalkoxy;
(b) reacting a compound of formula (A) as defined above in the presence of $H-R^7$, a coupling agent and a base, wherein $R^2$ is cyclopropylmethoxy, alkoxy or haloalkoxy;
(c) reacting a compound of formula (A) as defined above in the presence of a compound of formula (B)

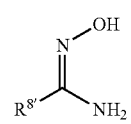

(B)

and carbonydiimidazole, wherein $R^{8'}$ is methyl or tert-butyl; or
(d) reacting a compound of formula (C)

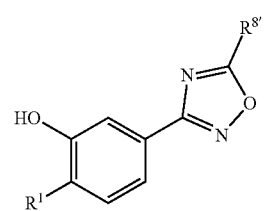

(C)

in the presence of $R^{2'}-X$, wherein $R^{2'}$ is cyclopropylmethyl, alkyl or haloalkyl, $R^{8'}$ is methyl or tert-butyl and X is a leaving group.

14. A pharmaceutical composition comprising a compound in accordance with claim 1, or a pharmaceutically acceptable salt or ester thereof, and a therapeutically inert carrier.

15. A method for the treatment or prophylaxis of pain, atherosclerosis, age-related macular degeneration, diabetic retinopathy, glaucoma, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, neurodegeneration, stroke, transient ischemic attack or uveitis, which method comprises administering to a patient in need thereof an effective amount of a compound of claim 1, or a pharmaceutically acceptable salt or ester thereof.

16. The compound according to claim 11, wherein the compound is selected from the group consisting of:
- N-[(2S)-4-amino-2-cyclopropyl-4-oxobutan-2-yl]-4-cyclopropyl-3-(2,2,2-trifluoroethoxy)benzamide;
- N-[(2R)-4-amino-2-cyclopropyl-4-oxobutan-2-yl]-4-cyclopropyl-3-[(propan-2-yl)oxy]benzamide; and
- N-[(2R)-4-amino-2-cyclopropyl-4-oxobutan-2-yl]-4-cyclopropyl-3-(2-fluoroethoxy)benzamide;

or a pharmaceutically acceptable salt thereof.

17. The compound according to claim 11, wherein the compound is 1-[4-cyclopropyl-3-(3,3-difluoropyrrolidin-1-yl)benzoyl]-4,4-difluoro-L-prolinamide, or a pharmaceutically acceptable salt thereof.

18. The compound according to claim 11, wherein the compound N-[(2R)-4-amino-2-cyclopropyl-4-oxobutan-2-yl]-4-cyclopropyl-3-(3,3-difluoropyrrolidin-1-yl)benzamide, or a pharmaceutically acceptable salt thereof.

19. The compound according to claim 11, wherein the compound is 4-cyclopropyl-3-(3,3-difluoropyrrolidin-1-yl)-N-[(2 S)-3,3-dimethyl-1-(methylamino)-1-oxobutan-2-yl]benzamide, or a pharmaceutically acceptable salt thereof.

20. A pharmaceutical composition comprising a compound of claim 11, or a pharmaceutically acceptable salt thereof, and a therapeutically inert carrier.

\* \* \* \* \*